US012692289B2

(12) United States Patent
Zhao et al.

(10) Patent No.: US 12,692,289 B2
(45) Date of Patent: Jul. 28, 2026

(54) TUMOR-SPECIFIC PEPTIDE ANTIGENS FOR OVARIAN CANCER AND USES THEREOF

(71) Applicant: UNIVERSITE DE MONTREAL, Montreal (CA)

(72) Inventors: Qingchuan Zhao, Saint-Laurent (CA); Pierre Thibault, Montreal (CA); Claude Perrault, Montreal (CA); Sebastien Lemieux, Lasalle (CA)

(73) Assignee: UNIVERSITE DE MONTREAL, Montreal (CA)

( * ) Notice: Subject to any disclaimer, the term of this patent is extended or adjusted under 35 U.S.C. 154(b) by 1029 days.

(21) Appl. No.: 17/622,552

(22) PCT Filed: Jun. 22, 2020

(86) PCT No.: PCT/CA2020/050869
§ 371 (c)(1),
(2) Date: Dec. 23, 2021

(87) PCT Pub. No.: WO2020/257922
PCT Pub. Date: Dec. 30, 2020

(65) Prior Publication Data
US 2022/0354937 A1 Nov. 10, 2022

Related U.S. Application Data

(60) Provisional application No. 62/866,089, filed on Jun. 25, 2019.

(51) Int. Cl.
| | |
|---|---|
| *C07K 7/08* | (2006.01) |
| *A61K 35/17* | (2025.01) |
| *A61K 39/00* | (2006.01) |
| *A61P 15/00* | (2006.01) |
| *A61P 35/00* | (2006.01) |
| *C07K 14/705* | (2006.01) |
| *C12N 15/113* | (2010.01) |

(52) U.S. Cl.
CPC .............. *C07K 7/08* (2013.01); *A61K 35/17* (2013.01); *A61K 39/0011* (2013.01); *A61P 15/00* (2018.01); *A61P 35/00* (2018.01); *C07K 14/70517* (2013.01); *C12N 15/1135* (2013.01); *C12N 2310/11* (2013.01)

(58) Field of Classification Search
CPC C07K 7/08; C07K 14/4748; C07K 14/70539; C12N 5/0636; A61K 2239/59
See application file for complete search history.

(56) References Cited

U.S. PATENT DOCUMENTS

| | | |
|---|---|---|
| 2012/0077696 A1 | 3/2012 | Admon et al. |
| 2017/0022251 A1 | 1/2017 | Rammensee et al. |
| 2017/0035807 A1 | 2/2017 | Schuster et al. |
| 2017/0096461 A1 | 4/2017 | Mahr et al. |
| 2017/0266271 A1 | 9/2017 | Weinschenk et al. |

FOREIGN PATENT DOCUMENTS

| | | |
|---|---|---|
| CN | 107889489 A | 4/2018 |
| CN | 107922469 A | 4/2018 |
| EP | 3027203 B1 | 7/2020 |
| JP | 2003111595 A | 4/2003 |
| WO | 2017009400 A1 | 1/2017 |
| WO | 2018138257 A1 | 8/2018 |
| WO | 2020041876 A1 | 3/2020 |
| WO | 2020260898 A2 | 12/2020 |

OTHER PUBLICATIONS

Ali, M , et al., "Induction of neoantigen-reactive T cells from healthy donors", Nature Protocols 14, 1926-1943 (2019).
Andreatta, M , et al., "Gapped sequence alignment using artificial neural networks: application to the MHC class I system", Bioinformatics 32, 511-517 (2016).
Bassani-Sternberg, M , et al., "Direct identification of clinically relevant neoepitopes presented on native human melanoma tissue by mass spectrometry", Nature Communications 7, 13404, doi:10.1038/ncomms13404, 16 pages (2016).
Bassani-Sternberg, M , et al., "Mass Spectrometry of Human Leukocyte Antigen Class I Peptidomes Reveals Strong Effects of Protein Abundance and Turnover on Antigen Presentation", Molecular & Cellular Proteomics 14, 10.1074/mcp.M114.042812, 658-673 (2015).
Bilich, T , et al., "The HLA ligandome landscape of chronic myeloid leukemia delineates novel T-cell epitopes for immunotherapy", Blood 133(6), 550-565 (2019).
Bobisse, S , et al., "Sensitive and frequent identification of high avidity neo-epitope specific CD8™ T cells in immunotherapy-naive ovarian cancer", Nature Communications 9, 1092, 10 pages (2018).
Bolger, A , et al., "Trimmomatic: a flexible trimmer for Illumina sequence data", Bioinformatics 30 (15), 2114-2120 (2014).

(Continued)

*Primary Examiner* — Elly-Gerald Stoica
(74) *Attorney, Agent, or Firm* — Viksnins Harris Padys Malen LLP

(57) ABSTRACT

Ovarian cancer, notably high-grade serous ovarian cancer (HGSC), the principal cause of death from gynecological malignancies in the world, has not significantly benefited from recent progress in cancer immunotherapy. While HGSC infiltration by lymphocytes correlates with superior survival, the nature of antigens that can elicit anti-HGSC immune responses is unknown. Novel tumor-specific antigens (TSAs) shared by a large proportion of ovarian tumors are described herein. Most of the TSAs (>80%) described herein derives from aberrantly expressed unmutated genomic sequences, such as intronic and intergenic sequences, which are not expressed in normal tissues. Nucleic acids, compositions, cells and vaccines derived from these TSAs are described. The use of the TSAs, nucleic acids, compositions, cells and vaccines for the treatment of ovarian cancer is also described.

19 Claims, 13 Drawing Sheets

Specification includes a Sequence Listing.

(56)　　　　　　References Cited

OTHER PUBLICATIONS

Bowtell, D , et al., "Rethinking ovarian cancer II: reducing mortality from high-grade serous ovarian cancer", Nat Rev Cancer 15(11), 668-679 (2015).

Capietto, A , et al., "Characterizing neoantigens for personalized cancer immunotherapy", Current Opinion in Immunology 46, 58-65 (2017).

Caron, E , et al., "Analysis of Major Histocompatibility Complex (MHC) Immunopeptidomes Using Mass Spectrometry*'", Molecular & Cellular Proteomics 14, 3105-3117 (2015).

Colaprico, A , et al., "TCGADbiolinks: an R/Bioconductor package for integrative analysis of TCGA data", Nucleic Acids Research 44 (8), e71, doi:10.1093/nar/gkv1507 (2016).

Croft, N , et al., "Most viral peptides displayed by class I MHC on infected cells are immunogenic", PNAS 116 (8), 3112-3117 (2019).

Danaher, P , et al., "Gene expression markers of Tumor Infiltrating Leukocytes", Journal for Immuno Therapy of Cancer 5(18), 15 pages (2017).

Daouda, T , et al., "pyGeno: A Python package for precision medicine and proteogenomics [version 2; referees: 1 approved, 2 approved with reservations]", F1000Research 5 (381) doi: 10.12688/f1000research.8251.2, 8 pages (2016).

Delaney, J , et al., "Haploinsufficiency networks identify targetable patterns of allelic deficiency in low mutation ovarian cancer", Nature Communications 8, 14423, DOI:10.1038/ncomms14423, 11 pages (2016).

Deniger, D , et al., "T-cell Responses to TP53 "Hotspot" Mutations Clinical (f=) [ol=14 Research and Unique Neoantigens Expressed by Human Ovarian Cancers", Clin Cancer Res 24 (22), 5562-5573 (2018).

Ehx, G , et al., "Discovery and characterization of actionable tumor antigens", Genome Medicine 11(29), 3 pages (2019).

Gaidatzis, D , et al., "QuasR: quantification and annotation of short reads in R", Bioinformatics 31 (7), 1130-1132 (2015).

Garrison, E , et al., "Haplotype-based variant detection from short-read sequencing", arXiv:1207.3907v2[q-bio.GN], 9 pages (2012).

Gfeller, D , et al., "Predicting Antigen Presentation—what Could we Learn From a Million Peptides?", Frontiers in Immunology 9, 1716, 17 pages (2018).

Gloger, A , et al., "Mass spectrometric analysis of the HLA class I peptidome of melanoma cell lines as a promising tool for the identification of putative tumor-associated HLA epitopes", Cancer Immunol Immunother 65(11), 1377-1393 (2016).

Gotter, J , et al., "Medullary Epithelial Cells of the Human Thymus Express a Highly Diverse Selection of Tissue-specific Genes Colocalized in Chromosomal Clusters", J Exp Med 199 (2), 155-166 (2004).

Granados, D , et al., "Impact of genomic polymorphisms on the repertoire of human MHC class I-associated peptides", Nature Communications 5, 3600, 14 pages (2014).

Haen, S , et al., "The repertoire of human tumor-associated epitopes—identi!cation and selection of antigens and their application in clinical trials", Current Opinion in Immunology 25, 277-283 (2013).

Hamanishi, J , et al., "Immune checkpoint inhibition in ovarian cancer", International Immunology 28(7), 339-348 (2016).

Hamanishi, J , et al., "Safety and Antitumor Activity of Anti-PD-1 Antibody, Nivolumab, in Patients with Platinum-Resistant Ovarian Cancer", Journal of Clinical Oncology 33(34), 13 pages (2015).

Jayson, G , et al., "Ovarian cancer", Lancet 384, 1376-1388 (2014).

Jongsma, M , et al., "The regulatory network behind MHC class I expression", Molecular Immunology 113, 16-21 (2019).

Kahles, A , et al., "Comprehensive Analysis of Alternative Splicing Across Tumors from 8,705 Patients", Cancer Cell 34, 211-224 (2018).

Lamoliatte, F , et al., "Uncovering the SUMOylation and ubiquitylation crosstalk in human cells using sequential peptide immunopurification", Nature Communications 8, 14109, 11 pages (2017).

Lanoix, J , et al., "Comparison of the Mhc I Immunopeptidome Repertoire of B-Cell Lymphoblasts Using Two Isolation Methods", Proteomics 18, 1700251, 13 pages (2018).

Laumont, C , et al., "Global proteogenomic analysis of human MHC class I-associated peptides derived from non-canonical reading frames", Nature Communications 7, 10238, 12 pages (2016).

Laumont, C , et al., "Noncoding regions are the main source of targetable tumor-specific antigens", Sci Transl Med 10, eaau5516, 11 pages (2018).

Liu, S , et al., "Efficient identification of neoantigen-® specific T-cell responses in advanced human ovarian cancer", Journal for Immuno Therapy of Cancer 7, 156, 17 pages (2019).

Loffler, M , et al., "Multi-omics discovery of exome-derived® neoantigens in hepatocellular carcinoma", Genome Medicine 11 (28), 16 pages (2019).

Maiers, M , et al., "High-resolution HLA alleles and haplotypes in the United States population", Human Immunology 68, 779-788 (2007).

Marty, R , et al., "MHC-I Genotype Restricts the Oncogenic Mutational Landscape", Cell 171, 1272-1283 (2017).

Millar, D , et al., "Central tolerance: what you see is what you don't get!", Nature Immunology 17 (2), 115-116 (2016).

Patent Cooperation Treaty , International Search Report and Written Opinion for PCT/CA2020/050869, 22 pages, dated Sep. 24, 2020.

Pearson, H , et al., "MHC class I-associated peptides derive from selective regions of the human genome", J Clin Invest 126(12), 4690-4701 (2016).

Peper, J , et al., "HLA ligandomics identifies histone deacetylase 1 as target for ovarian cancer immunotherapy", Oncoimmunology 5(5), pp. e1065369, doi: 10.1080/2162402X.2015.1065369 (2015).

Perez-Riverol, Y , et al., "The Pride database and related tools and resources in 2019: improving support for quantification data", Nucleic Acids Research 47, D442-D450 (2018).

Popovic, J , et al., "The only proposed T-cell epitope derived from the TEL-AML1 translocation is not naturally processed", Blood 118 (4), 945-954 (2011).

Rao, X , et al., "HLA class I allele promiscuity revisited", Immunogentics 63, 691-701 (2011).

Riley, R , et al., "Delivery technologies for cancer immunotherapy", Nat Rev Drug Discov 18 (3), 175-196 (2019).

Rizvi, N , et al., "Mutational landscape determines sensitivity to PD-1 blockade in non-small cell lung cancer", Science 348 (6230), 124-128 (2015).

Rodriguez-Garcia, A , et al., "T-cell target antigens across major gynecologic cancers", Gynecologic Oncology 145, 426-435 (2017).

Sansom, S , et al., "Population and single-cell genomics reveal the Aire dependency, relief from Polycomb silencing, and distribution of self-antigen expression in thymic epithelia", Genome Research 24, 1918-1931 (2014).

Schuster, H , et al., "The immunopeptidomic landscape of ovarian carcinomas", Proc Natl Acad Sci 114 (46), E9942-E9951 (2017).

Shao, W , et al., "The SysteMHC Atlas project", Nucleic Acids Research 46, D1237-D1247 (2018).

Simoni, Y , et al., "Bystander CD8⁺ T cells are abundant and phenotypically distinct in human tumour infiltrates, Nature 557, 575, 21 pages (2018).

Szolek, A , et al., "OptiType: precision HLA typing from next-generation sequencing data", Bioinformatics 30 (23), 3310-3316 (2014).

The Cancer Genome Atlas Research , "Integrated genomic analyses of ovarian carcinoma", Nature 474, 609-615 (2011).

The Uniprot Consortium , "UniProt: a worldwide hub of protein knowledge", Nucleic Acids Research 47, D506-D515 (2018).

Villani, A , et al., "Systems immunology: Learning the Rules of the Immune System", Annual Review Immunology 36, 813-842 (2018).

Want, M , et al., "Nature of tumour rejection antigens in ovarian cancer", Immunology 155, 202-210 (2018).

Yang, S , et al., "Landscape of genomic alterations in high-grade serous ovarian cancer from exceptional long- and shorty-term survivors", Genome Medicine 10 (81), 17 pages (2018).

Zhang, A , et al., "Interfaces of Malignant and Immunologic Clonal Dynamics in Ovarian Cancer", Cell 173, 1755-1769 (2018).

Zhao, Q , et al., "Proteogenomics Uncovers a Vast Repertoire of Shared Tumor-Specific Antigens in Ovarian Cancer", Cancer Immunol Res 8 (4), 544-555 (2020).

(56) References Cited

OTHER PUBLICATIONS

Hesnard, et al., "Immunogenicity of Non-Mutated Ovarian Cancer-Specific Antigens", Curr Oncol 31, 3099-3121 (2024).

Klein, et al., "Positive and negative selection of the T cell repertoire: what thymocytes see and don't see", Nat Rev Immunol 14 (6), 377-391 (2014).

Lu, et al., "Tumor Neoantigenicity Assessment with CSIN Score Incorporates Clonality and Immunogenicity to Predict Immunotherapy Outcomes", Sci Immunol 5 (44), 24 pages (2020).

Niemi, et al., "Neoantigen Vaccines; Clinical Trials, Classes, Indications, Adjuvants and Combinatorial Treatments", Cancers 14 (5163), 14 pages (2022).

Ruiz Cuevas, et al., "BamQuery: a proteogenomic tool to explore the immunopeptidome and prioritize actionable tumor antigens", Genome Biology 24 (188), 1-33 (2023).

Sette, et al., "The Relationship Between Class I Binding Affinity and Immunogenicity of Potential Cytotoxic T Cell Epitopes", The Journal of Immunology 153, 5586-5592, 9 pages (1994).

Zhao, et al., "Engineered T Cell Therapy for Cancer in the Clinic", Frontiers in Immunology 10 (2250), 1-20 (2019).

Mirabile-Brightman, et al., "Advances in the development of personalized neoantigen therapies", J Exp Med 223(2), e20241234, 1-14 (2026).

Nguyen, et al., "Neoantigen-based mRNA vaccine exhibits superior anti-tumor activity compared to synthetic long peptides in an in vivo lung carcinoma model", Cancer Immunology, Immunotherapy 74, 145, 17 pages (2025).

SEQUENCE LISTING

```
<160> NUMBER OF SEQ ID NOS: 111

<210> SEQ ID NO 1
<211> LENGTH: 9
<212> TYPE: PRT
<213> ORGANISM: Homo sapiens

<400> SEQUENCE: 1

Leu Ala Ser Thr Pro Val Val Glu Lys
1               5

<210> SEQ ID NO 2
<211> LENGTH: 10
<212> TYPE: PRT
<213> ORGANISM: Homo sapiens

<400> SEQUENCE: 2

Ile Leu Asn Pro Glu Glu Leu Glu Lys Tyr
1               5                   10

<210> SEQ ID NO 3
<211> LENGTH: 10
<212> TYPE: PRT
<213> ORGANISM: Homo sapiens

<400> SEQUENCE: 3

Leu Leu Asn Pro Glu Glu Ile Glu Lys Tyr
1               5                   10

<210> SEQ ID NO 4
<211> LENGTH: 9
<212> TYPE: PRT
<213> ORGANISM: Homo sapiens

<400> SEQUENCE: 4

Arg Pro Arg Pro Pro Pro Pro Pro Pro
1               5

<210> SEQ ID NO 5
<211> LENGTH: 10
```

```
<212> TYPE: PRT
<213> ORGANISM: Homo sapiens

<400> SEQUENCE: 5

Lys Gln Leu Gln Glu Gln Ala Met Gln Phe
1               5                   10

<210> SEQ ID NO 6
<211> LENGTH: 9
<212> TYPE: PRT
<213> ORGANISM: Homo sapiens

<400> SEQUENCE: 6

Arg Pro Arg Thr Ala Gly Pro Pro Arg
1               5

<210> SEQ ID NO 7
<211> LENGTH: 9
<212> TYPE: PRT
<213> ORGANISM: Homo sapiens

<400> SEQUENCE: 7

Arg Ala Pro Pro Pro Pro Lys Pro Met
1               5

<210> SEQ ID NO 8
<211> LENGTH: 8
<212> TYPE: PRT
<213> ORGANISM: Homo sapiens

<400> SEQUENCE: 8

Arg Pro Ala Ser Ser Arg Pro Leu
1               5

<210> SEQ ID NO 9
<211> LENGTH: 8
<212> TYPE: PRT
<213> ORGANISM: Homo sapiens

<400> SEQUENCE: 9

Arg Pro Gly Val Lys Leu Ile Leu
1               5

<210> SEQ ID NO 10
<211> LENGTH: 9
<212> TYPE: PRT
<213> ORGANISM: Homo sapiens

<400> SEQUENCE: 10

Trp Gly Thr Pro Pro Ser Pro Pro Pro
1               5

<210> SEQ ID NO 11
<211> LENGTH: 9
<212> TYPE: PRT
<213> ORGANISM: Homo sapiens

<400> SEQUENCE: 11

Ala Glu Leu Arg Gly Thr Ala Ser Leu
1               5

<210> SEQ ID NO 12
<211> LENGTH: 8
<212> TYPE: PRT
<213> ORGANISM: Homo sapiens
```

-continued

<400> SEQUENCE: 12

Ser Glu Ala Lys Leu Thr Gly Leu
1               5

<210> SEQ ID NO 13
<211> LENGTH: 8
<212> TYPE: PRT
<213> ORGANISM: Homo sapiens

<400> SEQUENCE: 13

Ser Glu Ile Pro Thr Lys Lys Leu
1               5

<210> SEQ ID NO 14
<211> LENGTH: 9
<212> TYPE: PRT
<213> ORGANISM: Homo sapiens

<400> SEQUENCE: 14

Val Leu Asp Asn Lys Asp Tyr Phe Leu
1               5

<210> SEQ ID NO 15
<211> LENGTH: 9
<212> TYPE: PRT
<213> ORGANISM: Homo sapiens

<400> SEQUENCE: 15

Arg Pro Phe Ser Pro Pro Pro Ser Phe
1               5

<210> SEQ ID NO 16
<211> LENGTH: 9
<212> TYPE: PRT
<213> ORGANISM: Homo sapiens

<400> SEQUENCE: 16

Arg Asn Leu Pro Leu Val Leu Ile Phe
1               5

<210> SEQ ID NO 17
<211> LENGTH: 9
<212> TYPE: PRT
<213> ORGANISM: Homo sapiens

<400> SEQUENCE: 17

Thr Leu Leu Pro Arg Leu Val Phe Ile
1               5

<210> SEQ ID NO 18
<211> LENGTH: 9
<212> TYPE: PRT
<213> ORGANISM: Homo sapiens

<400> SEQUENCE: 18

Arg Ala Val Ile Val Val Arg Leu Val
1               5

<210> SEQ ID NO 19
<211> LENGTH: 10
<212> TYPE: PRT
<213> ORGANISM: Homo sapiens

<400> SEQUENCE: 19

Arg Leu Val Thr Glu Pro Ser Gly Pro Lys
1               5                   10

<210> SEQ ID NO 20
<211> LENGTH: 9
<212> TYPE: PRT
<213> ORGANISM: Homo sapiens

<400> SEQUENCE: 20

Arg Met Lys Thr Phe Met Met Ser His
1               5

<210> SEQ ID NO 21
<211> LENGTH: 9
<212> TYPE: PRT
<213> ORGANISM: Homo sapiens

<400> SEQUENCE: 21

Thr Ser Asp Arg Leu Phe Leu Gly Tyr
1               5

<210> SEQ ID NO 22
<211> LENGTH: 9
<212> TYPE: PRT
<213> ORGANISM: Homo sapiens

<400> SEQUENCE: 22

Val Val Ser Pro Ala Ser Ser Gly Lys
1               5

<210> SEQ ID NO 23
<211> LENGTH: 9
<212> TYPE: PRT
<213> ORGANISM: Homo sapiens

<400> SEQUENCE: 23

Tyr Gly Leu Pro Arg Val Val Ala Val
1               5

<210> SEQ ID NO 24
<211> LENGTH: 9
<212> TYPE: PRT
<213> ORGANISM: Homo sapiens

<400> SEQUENCE: 24

Glu Val Thr Lys Leu Asn Gln Lys Phe
1               5

<210> SEQ ID NO 25
<211> LENGTH: 9
<212> TYPE: PRT
<213> ORGANISM: Homo sapiens

<400> SEQUENCE: 25

Leu Thr Val Glu Ile Ala Lys Ala Leu
1               5

<210> SEQ ID NO 26
<211> LENGTH: 10
<212> TYPE: PRT
<213> ORGANISM: Homo sapiens

<400> SEQUENCE: 26

Asn Pro Ser Glu Gly Ser Gly Ile Arg Leu

```
1              5                   10
```

<210> SEQ ID NO 27
<211> LENGTH: 9
<212> TYPE: PRT
<213> ORGANISM: Homo sapiens

<400> SEQUENCE: 27

Thr Ala Ser Asp Leu Asn Leu Lys Val
1               5

<210> SEQ ID NO 28
<211> LENGTH: 8
<212> TYPE: PRT
<213> ORGANISM: Homo sapiens

<400> SEQUENCE: 28

Leu Ser Gly Cys Cys Ser Leu Tyr
1               5

<210> SEQ ID NO 29
<211> LENGTH: 9
<212> TYPE: PRT
<213> ORGANISM: Homo sapiens

<400> SEQUENCE: 29

Pro Ala Pro Ile Pro Cys Pro Ala Ile
1               5

<210> SEQ ID NO 30
<211> LENGTH: 9
<212> TYPE: PRT
<213> ORGANISM: Homo sapiens

<400> SEQUENCE: 30

Arg Leu Leu Leu Pro Leu Gln Ser Arg
1               5

<210> SEQ ID NO 31
<211> LENGTH: 9
<212> TYPE: PRT
<213> ORGANISM: Homo sapiens

<400> SEQUENCE: 31

Ser Val Tyr Met Ala Thr Thr Leu Lys
1               5

<210> SEQ ID NO 32
<211> LENGTH: 9
<212> TYPE: PRT
<213> ORGANISM: Homo sapiens

<400> SEQUENCE: 32

Thr Thr Leu Lys Tyr Leu Trp Lys Lys
1               5

<210> SEQ ID NO 33
<211> LENGTH: 9
<212> TYPE: PRT
<213> ORGANISM: Homo sapiens

<400> SEQUENCE: 33

Val Tyr Leu Lys Trp Ala Gln Ile Leu
1               5

<210> SEQ ID NO 34
<211> LENGTH: 9
<212> TYPE: PRT
<213> ORGANISM: Homo sapiens

<400> SEQUENCE: 34

Val Tyr Met Ala Thr Thr Leu Lys Tyr
1               5

<210> SEQ ID NO 35
<211> LENGTH: 8
<212> TYPE: PRT
<213> ORGANISM: Homo sapiens

<400> SEQUENCE: 35

Tyr Leu Lys Trp Ala Gln Ile Leu
1               5

<210> SEQ ID NO 36
<211> LENGTH: 9
<212> TYPE: PRT
<213> ORGANISM: Homo sapiens

<400> SEQUENCE: 36

Ala Thr Trp Gln Ser Val Leu Ala Arg
1               5

<210> SEQ ID NO 37
<211> LENGTH: 9
<212> TYPE: PRT
<213> ORGANISM: Homo sapiens

<400> SEQUENCE: 37

Ala Glu Thr Gly Val Lys Lys Pro Gln
1               5

<210> SEQ ID NO 38
<211> LENGTH: 9
<212> TYPE: PRT
<213> ORGANISM: Homo sapiens

<400> SEQUENCE: 38

Ala Thr Ala Val Arg Thr Val Thr Leu
1               5

<210> SEQ ID NO 39
<211> LENGTH: 9
<212> TYPE: PRT
<213> ORGANISM: Homo sapiens

<400> SEQUENCE: 39

Cys Leu Leu Gly Ile Ser Leu Lys Val
1               5

<210> SEQ ID NO 40
<211> LENGTH: 9
<212> TYPE: PRT
<213> ORGANISM: Homo sapiens

<400> SEQUENCE: 40

Glu Ser Asp Glu Gln Thr Leu Asn Tyr
1               5

<210> SEQ ID NO 41

```
<211> LENGTH: 9
<212> TYPE: PRT
<213> ORGANISM: Homo sapiens

<400> SEQUENCE: 41

Ile Ile Leu Asp Val Gly Cys Leu Tyr
1               5

<210> SEQ ID NO 42
<211> LENGTH: 8
<212> TYPE: PRT
<213> ORGANISM: Homo sapiens

<400> SEQUENCE: 42

Ile Arg Gln Lys Val Glu Val Leu
1               5

<210> SEQ ID NO 43
<211> LENGTH: 9
<212> TYPE: PRT
<213> ORGANISM: Homo sapiens

<400> SEQUENCE: 43

Ile Tyr Val Leu Gln Val Pro Glu Leu
1               5

<210> SEQ ID NO 44
<211> LENGTH: 8
<212> TYPE: PRT
<213> ORGANISM: Homo sapiens

<400> SEQUENCE: 44

Leu Phe Phe Ile Lys Leu Thr Leu
1               5

<210> SEQ ID NO 45
<211> LENGTH: 10
<212> TYPE: PRT
<213> ORGANISM: Homo sapiens

<400> SEQUENCE: 45

Leu Leu Glu Glu Leu Ile Ser Asn Ile Val
1               5                   10

<210> SEQ ID NO 46
<211> LENGTH: 9
<212> TYPE: PRT
<213> ORGANISM: Homo sapiens

<400> SEQUENCE: 46

Leu Leu Gln Gln Leu Ser Arg Ser Leu
1               5

<210> SEQ ID NO 47
<211> LENGTH: 9
<212> TYPE: PRT
<213> ORGANISM: Homo sapiens

<400> SEQUENCE: 47

Leu Val Gly Ala Ser Pro His Val Leu
1               5

<210> SEQ ID NO 48
<211> LENGTH: 9
<212> TYPE: PRT
```

<213> ORGANISM: Homo sapiens

<400> SEQUENCE: 48

Asn Ala Phe Leu Val Leu Phe Ser Val
1               5

<210> SEQ ID NO 49
<211> LENGTH: 8
<212> TYPE: PRT
<213> ORGANISM: Homo sapiens

<400> SEQUENCE: 49

Arg Pro Ala Ser Leu Arg Lys Leu
1               5

<210> SEQ ID NO 50
<211> LENGTH: 8
<212> TYPE: PRT
<213> ORGANISM: Homo sapiens

<400> SEQUENCE: 50

Arg Val Tyr Asn Leu Thr Thr Lys
1               5

<210> SEQ ID NO 51
<211> LENGTH: 9
<212> TYPE: PRT
<213> ORGANISM: Homo sapiens

<400> SEQUENCE: 51

Ser Leu Ile Pro Thr Ala Leu Ser Leu
1               5

<210> SEQ ID NO 52
<211> LENGTH: 9
<212> TYPE: PRT
<213> ORGANISM: Homo sapiens

<400> SEQUENCE: 52

Ser Leu Asn Ser Arg Ser Gln Leu Lys
1               5

<210> SEQ ID NO 53
<211> LENGTH: 8
<212> TYPE: PRT
<213> ORGANISM: Homo sapiens

<400> SEQUENCE: 53

Ser Arg Lys Ala His His Ala Leu
1               5

<210> SEQ ID NO 54
<211> LENGTH: 10
<212> TYPE: PRT
<213> ORGANISM: Homo sapiens

<400> SEQUENCE: 54

Ser Ser Ala Leu Leu Ala Val Ala Leu Lys
1               5                   10

<210> SEQ ID NO 55
<211> LENGTH: 11
<212> TYPE: PRT
<213> ORGANISM: Homo sapiens

```
<400> SEQUENCE: 55

Ser Ser Ser Ala Leu Leu Ala Val Ala Leu Lys
1               5                   10

<210> SEQ ID NO 56
<211> LENGTH: 9
<212> TYPE: PRT
<213> ORGANISM: Homo sapiens

<400> SEQUENCE: 56

Thr Leu Ile Pro Arg Ile Leu Thr Leu
1               5

<210> SEQ ID NO 57
<211> LENGTH: 9
<212> TYPE: PRT
<213> ORGANISM: Homo sapiens

<400> SEQUENCE: 57

Thr Leu Leu Pro Asp Leu Gln Thr Leu
1               5

<210> SEQ ID NO 58
<211> LENGTH: 9
<212> TYPE: PRT
<213> ORGANISM: Homo sapiens

<400> SEQUENCE: 58

Thr Leu Val Val Ser Ile Ile Ile Tyr
1               5

<210> SEQ ID NO 59
<211> LENGTH: 8
<212> TYPE: PRT
<213> ORGANISM: Homo sapiens

<400> SEQUENCE: 59

Thr Asn Ile Ile Lys His Leu Leu
1               5

<210> SEQ ID NO 60
<211> LENGTH: 9
<212> TYPE: PRT
<213> ORGANISM: Homo sapiens

<400> SEQUENCE: 60

Thr Val Gln Asn Ser Arg Ser Leu Lys
1               5

<210> SEQ ID NO 61
<211> LENGTH: 9
<212> TYPE: PRT
<213> ORGANISM: Homo sapiens

<400> SEQUENCE: 61

Val Leu Phe Leu Lys Leu Glu Leu Leu
1               5

<210> SEQ ID NO 62
<211> LENGTH: 9
<212> TYPE: PRT
<213> ORGANISM: Homo sapiens

<400> SEQUENCE: 62
```

-continued

```
Val Leu Ser Pro Pro Leu Ser Pro Lys
1               5

<210> SEQ ID NO 63
<211> LENGTH: 9
<212> TYPE: PRT
<213> ORGANISM: Homo sapiens

<400> SEQUENCE: 63

Tyr Leu Ala Thr Lys Phe Met Pro Ile
1               5

<210> SEQ ID NO 64
<211> LENGTH: 9
<212> TYPE: PRT
<213> ORGANISM: Homo sapiens

<400> SEQUENCE: 64

Ser His Asn Leu Pro Ala Asn Ile Leu
1               5

<210> SEQ ID NO 65
<211> LENGTH: 9
<212> TYPE: PRT
<213> ORGANISM: Homo sapiens

<400> SEQUENCE: 65

Thr Glu Ile Ser Asn Ser Gln Ala Ala
1               5

<210> SEQ ID NO 66
<211> LENGTH: 11
<212> TYPE: PRT
<213> ORGANISM: Homo sapiens

<400> SEQUENCE: 66

Thr Pro Ser Ser His Leu Gly Leu Leu Ser Tyr
1               5                   10

<210> SEQ ID NO 67
<211> LENGTH: 9
<212> TYPE: PRT
<213> ORGANISM: Homo sapiens

<400> SEQUENCE: 67

Val Thr Ile Asp Thr Thr Gln Thr Lys
1               5

<210> SEQ ID NO 68
<211> LENGTH: 9
<212> TYPE: PRT
<213> ORGANISM: Homo sapiens

<400> SEQUENCE: 68

Ala Pro Ala Ser Phe Ala Ala Thr Arg
1               5

<210> SEQ ID NO 69
<211> LENGTH: 11
<212> TYPE: PRT
<213> ORGANISM: Homo sapiens

<400> SEQUENCE: 69

Ala Thr Leu Gln Ala Ala Ile Leu Tyr Glu Lys
1               5                   10
```

US 12,692,289 B2

67

68

-continued

```
<210> SEQ ID NO 70
<211> LENGTH: 8
<212> TYPE: PRT
<213> ORGANISM: Homo sapiens

<400> SEQUENCE: 70

Asp Leu Leu Lys Lys Thr Val Leu
1               5

<210> SEQ ID NO 71
<211> LENGTH: 9
<212> TYPE: PRT
<213> ORGANISM: Homo sapiens

<400> SEQUENCE: 71

Asp Ser Ile Lys Ala Ser Thr Thr Leu
1               5

<210> SEQ ID NO 72
<211> LENGTH: 9
<212> TYPE: PRT
<213> ORGANISM: Homo sapiens

<400> SEQUENCE: 72

Phe Ile Leu Asp Ile Ala Lys Leu Leu
1               5

<210> SEQ ID NO 73
<211> LENGTH: 9
<212> TYPE: PRT
<213> ORGANISM: Homo sapiens

<400> SEQUENCE: 73

Ile Val Ser Ala Gln Asn Leu Ile Lys
1               5

<210> SEQ ID NO 74
<211> LENGTH: 8
<212> TYPE: PRT
<213> ORGANISM: Homo sapiens

<400> SEQUENCE: 74

Leu Cys Ile Lys Arg Phe Leu Ile
1               5

<210> SEQ ID NO 75
<211> LENGTH: 9
<212> TYPE: PRT
<213> ORGANISM: Homo sapiens

<400> SEQUENCE: 75

Leu Leu Leu Asp Lys Leu Tyr Phe Leu
1               5

<210> SEQ ID NO 76
<211> LENGTH: 8
<212> TYPE: PRT
<213> ORGANISM: Homo sapiens

<400> SEQUENCE: 76

Leu Leu Gln Lys Arg Val Pro Glu
1               5
```

-continued

```
<210> SEQ ID NO 77
<211> LENGTH: 9
<212> TYPE: PRT
<213> ORGANISM: Homo sapiens

<400> SEQUENCE: 77

Leu Leu Ser Ser Lys Leu Leu Leu Met
1               5

<210> SEQ ID NO 78
<211> LENGTH: 8
<212> TYPE: PRT
<213> ORGANISM: Homo sapiens

<400> SEQUENCE: 78

Leu Pro Gly Val Thr Arg Ser Leu
1               5

<210> SEQ ID NO 79
<211> LENGTH: 9
<212> TYPE: PRT
<213> ORGANISM: Homo sapiens

<400> SEQUENCE: 79

Leu Thr His Leu Val Ser Gln Glu Leu
1               5

<210> SEQ ID NO 80
<211> LENGTH: 9
<212> TYPE: PRT
<213> ORGANISM: Homo sapiens

<400> SEQUENCE: 80

Leu Thr Thr Thr Arg Val Ala Thr Ile
1               5

<210> SEQ ID NO 81
<211> LENGTH: 9
<212> TYPE: PRT
<213> ORGANISM: Homo sapiens

<400> SEQUENCE: 81

Leu Val Phe Asn Ile Ile Leu His Arg
1               5

<210> SEQ ID NO 82
<211> LENGTH: 9
<212> TYPE: PRT
<213> ORGANISM: Homo sapiens

<400> SEQUENCE: 82

Met Val Ala Arg Leu Thr Pro Leu Leu
1               5

<210> SEQ ID NO 83
<211> LENGTH: 9
<212> TYPE: PRT
<213> ORGANISM: Homo sapiens

<400> SEQUENCE: 83

Asn Ile Leu Gly Lys Ser Leu Thr Leu
1               5

<210> SEQ ID NO 84
<211> LENGTH: 9
```

```
<212> TYPE: PRT
<213> ORGANISM: Homo sapiens

<400> SEQUENCE: 84

Arg Leu Ala Thr Ala Pro Ser Glu Lys
1               5

<210> SEQ ID NO 85
<211> LENGTH: 9
<212> TYPE: PRT
<213> ORGANISM: Homo sapiens

<400> SEQUENCE: 85

Arg Thr Ala Thr Pro Leu Thr Met Lys
1               5

<210> SEQ ID NO 86
<211> LENGTH: 10
<212> TYPE: PRT
<213> ORGANISM: Homo sapiens

<400> SEQUENCE: 86

Arg Thr Ala Thr Pro Leu Thr Met Lys Lys
1               5                   10

<210> SEQ ID NO 87
<211> LENGTH: 10
<212> TYPE: PRT
<213> ORGANISM: Homo sapiens

<400> SEQUENCE: 87

Arg Thr His Gln Met Asn Thr Phe Gln Arg
1               5                   10

<210> SEQ ID NO 88
<211> LENGTH: 10
<212> TYPE: PRT
<213> ORGANISM: Homo sapiens

<400> SEQUENCE: 88

Tyr Leu Asp Thr Ala Gln Lys Asn Leu Tyr
1               5                   10

<210> SEQ ID NO 89
<211> LENGTH: 8
<212> TYPE: PRT
<213> ORGANISM: Homo sapiens

<400> SEQUENCE: 89

Glu Asn Val Leu Ser Lys Leu Tyr
1               5

<210> SEQ ID NO 90
<211> LENGTH: 9
<212> TYPE: PRT
<213> ORGANISM: Homo sapiens

<400> SEQUENCE: 90

Gly Thr Ala Gln Val Gly Ile Thr Lys
1               5

<210> SEQ ID NO 91
<211> LENGTH: 9
<212> TYPE: PRT
<213> ORGANISM: Homo sapiens
```

<400> SEQUENCE: 91

Val Leu Ala Gly Thr Val Leu Phe Lys
1               5

<210> SEQ ID NO 92
<211> LENGTH: 10
<212> TYPE: PRT
<213> ORGANISM: Homo sapiens

<400> SEQUENCE: 92

Arg Pro Gly Ala Gly Pro Pro Gly Ile Leu
1               5                   10

<210> SEQ ID NO 93
<211> LENGTH: 9
<212> TYPE: PRT
<213> ORGANISM: Homo sapiens

<400> SEQUENCE: 93

Ile Ile His Ser Ser Ser Leu Leu Leu
1               5

<210> SEQ ID NO 94
<211> LENGTH: 10
<212> TYPE: PRT
<213> ORGANISM: Homo sapiens

<400> SEQUENCE: 94

Ala Glu His Gln Glu Gly Thr Gly Thr Trp
1               5                   10

<210> SEQ ID NO 95
<211> LENGTH: 9
<212> TYPE: PRT
<213> ORGANISM: Homo sapiens

<400> SEQUENCE: 95

Glu Ala Leu Pro Asp Leu Glu Gln Leu
1               5

<210> SEQ ID NO 96
<211> LENGTH: 9
<212> TYPE: PRT
<213> ORGANISM: Homo sapiens

<400> SEQUENCE: 96

Gly Lys Asp Pro Asn Pro Val Val Leu
1               5

<210> SEQ ID NO 97
<211> LENGTH: 8
<212> TYPE: PRT
<213> ORGANISM: Homo sapiens

<400> SEQUENCE: 97

Pro Ser Pro Leu Arg Pro Ser Leu
1               5

<210> SEQ ID NO 98
<211> LENGTH: 10
<212> TYPE: PRT
<213> ORGANISM: Homo sapiens

<400> SEQUENCE: 98

```
Ser Leu Leu Asn Val Ile Gly Leu Ser Val
1               5                   10

<210> SEQ ID NO 99
<211> LENGTH: 9
<212> TYPE: PRT
<213> ORGANISM: Homo sapiens

<400> SEQUENCE: 99

Tyr Arg Ala Leu Ser Leu Ala Gly Leu
1               5

<210> SEQ ID NO 100
<211> LENGTH: 10
<212> TYPE: PRT
<213> ORGANISM: Homo sapiens

<400> SEQUENCE: 100

Ser Leu Gly Ala Gly Leu Ser Pro Cys Leu
1               5                   10

<210> SEQ ID NO 101
<211> LENGTH: 9
<212> TYPE: PRT
<213> ORGANISM: Homo sapiens

<400> SEQUENCE: 101

Ser Pro Gln Thr Gln Thr His Thr Leu
1               5

<210> SEQ ID NO 102
<211> LENGTH: 10
<212> TYPE: PRT
<213> ORGANISM: Homo sapiens

<400> SEQUENCE: 102

Ser Thr Gln Met Thr Ile Thr Thr Gln Lys
1               5                   10

<210> SEQ ID NO 103
<211> LENGTH: 9
<212> TYPE: PRT
<213> ORGANISM: Homo sapiens

<400> SEQUENCE: 103

Thr Pro Lys Leu Arg Glu Thr Ser Val
1               5

<210> SEQ ID NO 104
<211> LENGTH: 9
<212> TYPE: PRT
<213> ORGANISM: Homo sapiens

<400> SEQUENCE: 104

Ala Ser Asn Pro Val Ile Lys Lys Lys
1               5

<210> SEQ ID NO 105
<211> LENGTH: 9
<212> TYPE: PRT
<213> ORGANISM: Homo sapiens

<400> SEQUENCE: 105

Ala Glu Glu Glu Ile Met Lys Lys Ile
```

-continued 1               5

<210> SEQ ID NO 106
<211> LENGTH: 9
<212> TYPE: PRT
<213> ORGANISM: Homo sapiens

<400> SEQUENCE: 106

Phe Ala Phe Gly Glu Pro Arg Glu Leu
1               5

<210> SEQ ID NO 107
<211> LENGTH: 9
<212> TYPE: PRT
<213> ORGANISM: Homo sapiens

<400> SEQUENCE: 107

Gly Thr Ser Pro Pro Ser Val Glu Lys
1               5

<210> SEQ ID NO 108
<211> LENGTH: 9
<212> TYPE: PRT
<213> ORGANISM: Homo sapiens

<400> SEQUENCE: 108

Ile Met Lys Lys Ile Arg Glu Ser Tyr
1               5

<210> SEQ ID NO 109
<211> LENGTH: 10
<212> TYPE: PRT
<213> ORGANISM: Homo sapiens

<400> SEQUENCE: 109

Lys Glu Val Asp Pro Ala Ser Asn Thr Tyr
1               5               10

<210> SEQ ID NO 110
<211> LENGTH: 9
<212> TYPE: PRT
<213> ORGANISM: Homo sapiens

<400> SEQUENCE: 110

Arg Val Lys Ser Thr Ile Ser Ser Leu
1               5

<210> SEQ ID NO 111
<211> LENGTH: 9
<212> TYPE: PRT
<213> ORGANISM: Homo sapiens

<400> SEQUENCE: 111

Ser Gln Gly Phe Ser His Ser Gln Met
1               5

TUMOR-SPECIFIC PEPTIDE ANTIGENS FOR OVARIAN CANCER AND USES THEREOF

CROSS REFERENCE TO RELATED APPLICATIONS

The present application claims the benefit of U.S. provisional patent application Ser. No. 62/866,089 filed Jun. 25, 2019, which is incorporated herein by reference.

SEQUENCE LISTING

The instant application contains a Sequence Listing that has been submitted electronically in ASCII format and is hereby incorporated by reference in its entirety.

TECHNICAL FIELD

The present disclosure generally relates to cancer, and more specifically to tumor antigens specific for ovarian cancer useful for T-cell-based cancer immunotherapy.

BACKGROUND ART

Ovarian cancer is the principal cause of death from gynecological malignancies in the world and is responsible for over 14,000 deaths per year in the United States (1). High-grade serous ovarian cancer (HGSC) accounts for 70-80% of these deaths, and overall survival has not changed significantly for several decades (2). The positive correlation between the abundance of tumor-infiltrating lymphocytes (TILs) and increased overall survival hints that T cells can recognize biologically relevant tumor antigens in HGSC (3,4). Furthermore, strong evidence suggests that HGSC TILs adjacent to tumor epithelial cells are actively engaged in local immune editing. Indeed, in a multi-modality study of 212 HGSC samples from 38 patients, CD8$^+$ TILs negatively associated with malignant cell diversity (5). In line with this, and given the therapeutic efficacy of immune checkpoint inhibitors in several tumor types, clinical trials with one or more checkpoint inhibitors are currently underway in HGSC. However, initial trials with anti-PD1 have shown limited activity in HGSC (6,7).

In view of this, there is a pressing need to identify the antigens that can elicit therapeutic immune responses again ovarian tumors such as HGSC (3,8). Such antigens could be used as vaccines (±immune checkpoint inhibitors) or as targets for T-cell receptor-based approaches (cell therapy, bispecific biologics) (9).

The present description refers to a number of documents, the content of which is herein incorporated by reference in their entirety.

SUMMARY

The present disclosure provides the following items 1 to 61:

1. A tumor antigen peptide comprising one of the amino acid sequences set forth in SEQ ID NOs: 1-103.
2. The tumor antigen peptide of item 1, comprising one of the amino acid sequences set forth in SEQ ID NOs: 19-103.
3. The tumor antigen peptide of item 1 or 2, wherein said tumor antigen peptide binds to an HLA-A*01:01 molecule and comprises the amino acid sequence set forth in SEQ ID NO: 21, 28, 40, 41, 66 or 88.

4. The tumor antigen peptide of item 1 or 2, wherein said tumor antigen peptide binds to an HLA-A*02:01 molecule and comprises the amino acid sequence set forth in SEQ ID NO: 1, 19, 20, 22, 30, 31, 36, 50, 52, 60, 62, 73, 84, 85, 86 or 91.
5. The tumor antigen peptide of item 1 or 2, wherein said tumor antigen peptide binds to an HLA-A*11:01 molecule and comprises the amino acid sequence set forth in SEQ ID NO: 32, 54, 55, 67, 69, 81, 87, 90 or 102.
6. The tumor antigen peptide of item 1 or 2, wherein said tumor antigen peptide binds to an HLA-A*24:02 molecule and comprises the amino acid sequence set forth in SEQ ID NO: 33 or 43.
7. The tumor antigen peptide of item 1 or 2, wherein said tumor antigen peptide binds to an HLA-A*25:01 molecule and comprises one of the amino acid sequences set forth in SEQ ID NO: 24.
8. The tumor antigen peptide of item 1 or 2, wherein said tumor antigen peptide binds to an HLA-A*29:02 molecule and comprises one of the amino acid sequences set forth in SEQ ID NO: 34 or 58.
9. The tumor antigen peptide of item 1 or 2, wherein said tumor antigen peptide binds to an HLA-A*32:01 molecule and comprises the amino acid sequence set forth in SEQ ID NO: 16.
10. The tumor antigen peptide of item 1 or 2, wherein said tumor antigen peptide binds to an HLA-B*07:02 molecule and comprises the amino acid sequence set forth in SEQ ID NO: 4, 6, 8, 9, 26, 49, 78, 92, 97 or 101.
11. The tumor antigen peptide of item 1 or 2, wherein said tumor antigen peptide binds to an HLA-B*08:01 molecule and comprises one of the amino acid sequences set forth in SEQ ID NO: 23, 35, 42, 44, 46, 59, 63, 70, 74, 76, 83 or 103.
12. The tumor antigen peptide of item 1 or 2, wherein said tumor antigen peptide binds to an HLA-B*14:01 molecule and comprises the amino acid sequence set forth in SEQ ID NO: 53.
13. The tumor antigen peptide of item 1 or 2, wherein said tumor antigen peptide binds to an HLA-B*15:01 molecule and comprises the amino acid sequence set forth in SEQ ID NO: 2, 3 or 5.
14. The tumor antigen peptide of item 1 or 2, wherein said tumor antigen peptide binds to an HLA-B*18:01 molecule and comprises the amino acid sequence set forth in SEQ ID NO: 89.
15. The tumor antigen peptide of item 1 or 2, wherein said tumor antigen peptide binds to an HLA-B*39:01 molecule and comprises the amino acid sequence set forth in SEQ ID NO: 47, 64, 96 or 99.
16. The tumor antigen peptide of item 1 or 2, wherein said tumor antigen peptide binds to an HLA-B*40:01 molecule and comprises the amino acid sequence set forth in SEQ ID NO: 11, 12 or 13.
17. The tumor antigen peptide of item 1 or 2, wherein said tumor antigen peptide binds to an HLA-B*44:02 molecule and comprises the amino acid sequence set forth in SEQ ID NO: 65.
18. The tumor antigen peptide of item 1 or 2, wherein said tumor antigen peptide binds to an HLA-B*44:03 molecule and comprises the amino acid sequence set forth in SEQ ID NO: 37 or 94.
19. The tumor antigen peptide of item 1 or 2, wherein said tumor antigen peptide binds to an HLA-C*03:03 molecule and comprises the amino acid sequence set forth in SEQ ID NO: 10, 29, 71 or 95.

20. The tumor antigen peptide of item 1 or 2, wherein said tumor antigen peptide binds to an HLA-C*04:01 molecule and comprises the amino acid sequence set forth in SEQ ID NO: 6 or 15.

21. The tumor antigen peptide of item 1 or 2, wherein said tumor antigen peptide binds to an HLA-C*05:01 molecule and comprises the amino acid sequence set forth in SEQ ID NO: 27.

22. The tumor antigen peptide of item 1 or 2, wherein said tumor antigen peptide binds to an HLA-C*06:02 molecule and comprises the amino acid sequence set forth in SEQ ID NO: 18 or 72.

23. The tumor antigen peptide of item 1 or 2, wherein said tumor antigen peptide binds to an HLA-C*07:01 molecule and comprises the amino acid sequence set forth in SEQ ID NO: 38, 61 or 93.

24. The tumor antigen peptide of item 1 or 2, wherein said tumor antigen peptide binds to an HLA-C*07:02 molecule and comprises the amino acid sequence set forth in SEQ ID NO: 7.

25. The tumor antigen peptide of item 1 or 2, wherein said tumor antigen peptide binds to an HLA-C*12:03 molecule and comprises the amino acid sequence set forth in SEQ ID NO: 80.

26. The tumor antigen peptide of item 1 or 2, wherein said tumor antigen peptide binds to an HLA-C*14:02 molecule and comprises the amino acid sequence set forth in SEQ ID NO: 25, 57 or 79.

27. The tumor antigen peptide of any one of items 1-26, which is encoded by a sequence located a non-protein coding region of the genome and comprises the amino acid sequence set forth in any one of SEQ ID NOs: 1, 4, 6-8, 10, 13, 15-27 and 36-99, preferably SEQ ID NOs: 19-27 and 36-99.

28. The tumor antigen peptide of item 27, wherein said non-protein coding region of the genome is an untranslated transcribed region (UTR) and said tumor antigen peptide comprises the amino acid sequence set forth in any one of SEQ ID NOs: 1, 8, 10, 13, 15 and 19-27, preferably SEQ ID NOs: 19-27.

29. The tumor antigen peptide of item 27, wherein said non-protein coding region of the genome is an intron and said tumor antigen peptide comprises the amino acid sequence set forth in any one of SEQ ID NOs: 16, 17 and 36-64, preferably SEQ ID NOs: 36-64.

30. The tumor antigen peptide of item 27, wherein said non-protein coding region of the genome is an intergenic region and said tumor antigen peptide comprises the amino acid sequence set forth in any one of SEQ ID NOs: 65-84.

31. The tumor antigen peptide of item 27, wherein said non-protein coding region of the genome is an exon of a noncoding RNA transcript (ncRNA), and said tumor antigen peptide comprises the amino acid sequence set forth in any one of SEQ ID NOs: 4 and 85-92, preferably SEQ ID NOs: 85-92.

32. The tumor antigen peptide of item 27, wherein said non-protein coding region of the genome is an antisense strand of a gene, and said tumor antigen peptide comprises the amino acid sequence set forth in any one of SEQ ID NOs: 93-99.

33. A nucleic acid encoding the tumor antigen peptide of any one of items 1-32.

34. The nucleic acid of item 33, which is an mRNA or a viral vector.

35. A liposome comprising the tumor antigen peptide of any one of items 1-32 or the nucleic acid of item 33 or 34.

36. A composition comprising the tumor antigen peptide of any one of items 1-32, the nucleic acid of item 31 or 32, or the liposomes of item 33, and a pharmaceutically acceptable carrier.

37. A vaccine comprising the tumor antigen peptide of any one of items 1-32, the nucleic acid of item 33 or 34, the liposome of item 35, or the composition of item 36, and an adjuvant.

38. An isolated major histocompatibility complex (MHC) class I molecule comprising the tumor antigen peptide of any one of items 1-32 in its peptide binding groove.

39. The isolated MHC class I molecule of item 38, which is in the form of a multimer.

40. The isolated MHC class I molecule of item 39, wherein said multimer is a tetramer.

41. An isolated cell comprising (i) the tumor antigen peptide of any one of items 1-32 or (ii) a vector comprising a nucleotide sequence encoding tumor antigen peptide of any one of items 1-32.

42. An isolated cell expressing at its surface major histocompatibility complex (MHC) class I molecules comprising the tumor antigen peptide of any one of items 1-32 in their peptide binding groove.

43. The cell of item 42, which is an antigen-presenting cell (APC).

44. The cell of item 43, wherein said APC is a dendritic cell.

45. A T-cell receptor (TCR) that specifically recognizes the isolated MHC class I molecule of any one of items 38-40 and/or MHC class I molecules expressed at the surface of the cell of any one of items 42-44.

46. An isolated CD8$^+$ T lymphocyte expressing at its cell surface the TCR of item 45.

47. A cell population comprising at least 0.5% of CD8$^+$ T lymphocytes as defined in item 46.

48. A method of treating ovarian cancer in a subject comprising administering to the subject an effective amount of: (i) the tumor antigen peptide of any one of items 1-32; (ii) the nucleic acid of item 33 or 34; (iii) the liposome of item 35; (iv) the composition of item 36; (v) the vaccine of item 37; (vi) the cell of any one of items 41-45; (vii) the CD8$^+$ T lymphocytes of item 46; or (viii) the cell population of item 47.

49. The method of item 48, wherein said ovarian cancer is a serous carcinoma.

50. The method of item 49, wherein said serous carcinoma is high-grade serous carcinoma (HGSC).

51. The method of any one of items 48-50, further comprising administering at least one additional antitumor agent or therapy to the subject.

52. The method of item 51, wherein said at least one additional antitumor agent or therapy is a chemotherapeutic agent, immunotherapy, an immune checkpoint inhibitor, radiotherapy or surgery.

53. Use of: (i) the tumor antigen peptide of any one of items 1-32; (ii) the nucleic acid of item 33 or 34; (iii) the liposome of item 35; (iv) the composition of item 36; (v) the vaccine of item 37; (vi) the cell of any one of items 41-45; (vii) the CD8$^+$ T lymphocytes of item 46; or (viii) the cell population of item 47, for treating ovarian cancer in a subject.

54. Use of: (i) the tumor antigen peptide of any one of items 1-32; (ii) the nucleic acid of item 33 or 34; (iii) the liposome of item 35; (iv) the composition of item 36; (v) the vaccine of item 37; (vi) the cell of any one of items 41-45; (vii) the CD8$^+$ T lymphocytes of item 46; or (viii) the cell population of item 47, for the manufacture of a medicament for treating ovarian cancer in a subject.

55. The use of item 53 or 54, wherein said ovarian cancer is a serous carcinoma.

56. The use of item 55, wherein said serous carcinoma is high-grade serous carcinoma (HGSC).

57. The use of any one of items 53-56, further comprising the use of at least one additional antitumor agent or therapy.

58. The use of item 57, wherein said at least one additional antitumor agent or therapy is a chemotherapeutic agent, immunotherapy, an immune checkpoint inhibitor, radiotherapy or surgery.

59. The (i) the tumor antigen peptide of any one of items 1-32; (ii) the nucleic acid of item 33 or 34; (iii) the liposome of item 35; (iv) the composition of item 36; (v) the vaccine of item 37; (vi) the cell of any one of items 41-45; (vii) the CD8$^+$ T lymphocytes of item 46; or (viii) the cell population of item 47, for use in treating ovarian cancer in a subject.

60. The tumor antigen peptide, nucleic acid, liposome, composition, vaccine, cell, CD8$^+$ T lymphocytes, or cell population for use according to item 59, wherein said ovarian cancer is a serous carcinoma.

61. The tumor antigen peptide, nucleic acid, liposome, composition, vaccine, cell, CD8$^+$ T lymphocytes, or cell population for use according to item 60, wherein said serous carcinoma is high-grade serous carcinoma (HGSC).

62. The tumor antigen peptide, nucleic acid, liposome, composition, vaccine, cell, CD8$^+$ T lymphocytes, or cell population for use according to any one of items 59-61, wherein the tumor antigen peptide, nucleic acid, liposome, composition, vaccine, cell, CD8$^+$ T lymphocytes, or cell population is used in combination with at least one additional antitumor agent or therapy.

63. The tumor antigen peptide, nucleic acid, liposome, composition, vaccine, cell, CD8$^+$ T lymphocytes, or cell population for use according to item 62, wherein said at least one additional antitumor agent or therapy is a chemotherapeutic agent, immunotherapy, an immune checkpoint inhibitor, radiotherapy or surgery.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 3A: Number of MAPs (left) and TSAs (right) identified in each sample. FIG. 3B: Scatter plots show the Pearson correlation between the number of MAPs and TSAs identified per sample. FIG. 3C: Bar graph showing the origin of TSAs identified in the cohort studied herein and the dataset of Schuster et al. Shades of blue depict the number of TSAs resulting from in-frame exonic translation (Coding-in), out-of-frame exonic translation (Coding-out) or non exonic translation (Noncoding). FIG. 3D: Pie chart showing the translational reading frame (inner pie), detailed genomic origin (middle pie) of aeTSAs and their report status (outer circle).

FIG. 5A: Heatmap shows the Spearman correlation between aeTSA RNA expression level and DNA copy number, promoter methylation or gene expression for aeTSAs located in genes (left) or out-of-gene (right). Not available data are showed as light gray. FIG. 5B: The number of aeTSAs identified from each chromosome arm (top) with arm-level amplification score (bottom). Asterisks indicate the amplification considered to be significant (Q value<0.25).

FIGS. 6A-E show that the presentation of three aeTSAs may elicit spontaneous anti-tumor immune responses. FIGS. 6A-C: Kaplan-Meier curves depict survival of four group of patients in the TCGA-OV cohort, For the three individual aeTSAs, one group could present the aeTSA (EP) and three groups could not (ED, ND and NP). ED: expression of aeTSA-coding RNA, relevant HLA allotype absent; ND: no expression of aeTSA-coding RNA, relevant HLA allotype absent; EP: expression of aeTSA-coding RNA, relevant HLA allotype present; NP: no expression of aeTSA-coding RNA, relevant HLA allotype present. Color shades represent the 95% confidence interval. Log-rank P values are indicated. FIG. 60, E: the abundance of T and cytotoxic cells in tumors from the four groups presented in FIG. 6C.

FIG. 8A: Example of an excluded TSA candidate matching common polymorphism reported in dbSNP. The variant nucleotide was also seen paired normal sample. FIG. 8B: Example of mTSA with variant absent from dbSNP. The variant nucleotide is only detected in paired normal with one read which likely to be a sequencing error.

Figure 10:
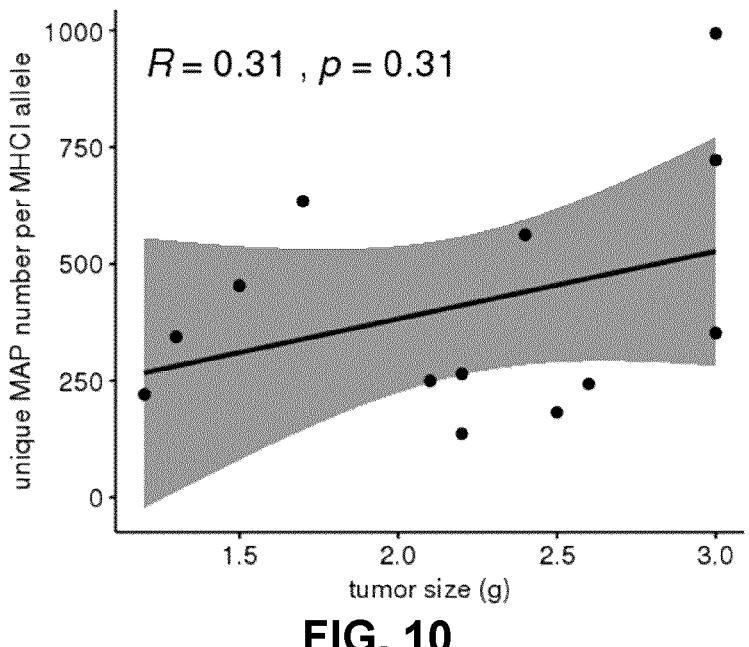

FIG. 10 is a graph showing the correlation between the number of MAPs and tumor size. Scatter plot shows the Pearson correlation between tumor size (x axis) and MAP number identified per HLA allele (y axis) for each sample. Only samples from Schuster et al. (the largest subgroup) were used in this plot to avoid batch effect.

Figure 11A:
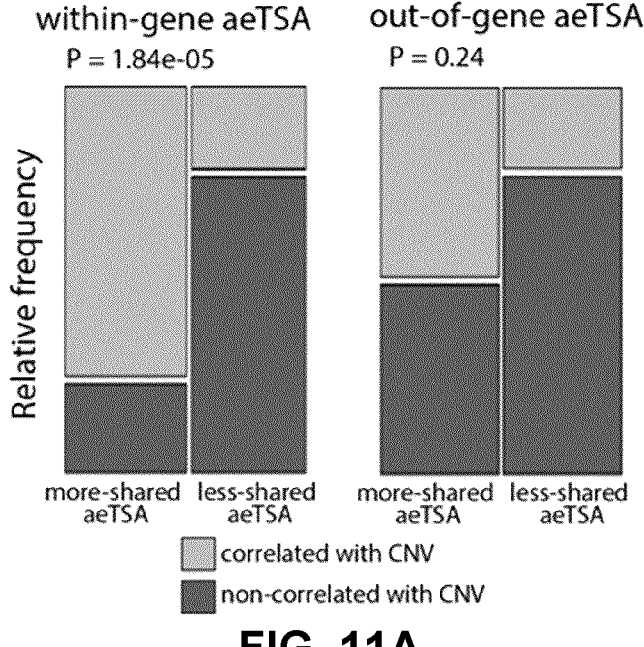
Figure 11B:
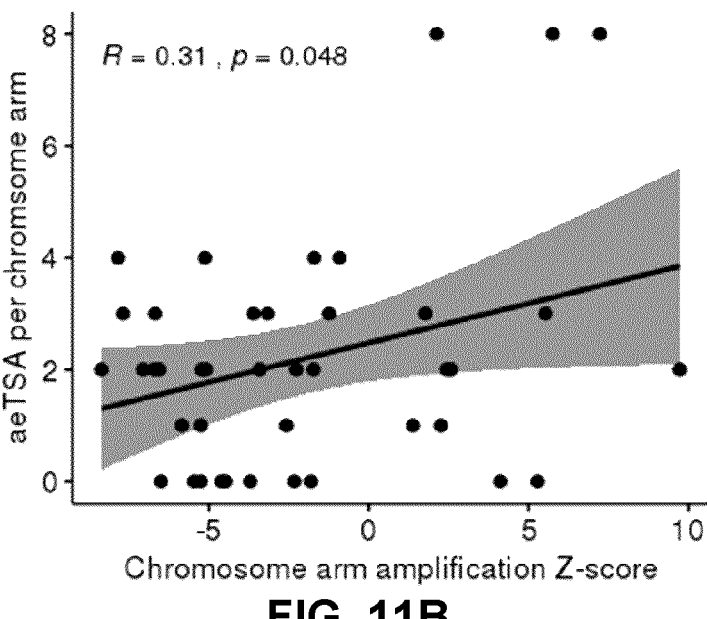

FIGS. 11A-B are graphs showing the relationship between aeTSA expression and DNA copy number variation (CNV). FIG. 11A: The enrichment analysis for significant correlations between within-gene aeTSA RNA expression and CNV, calculated with Fisher's exact test. aeTSAs are grouped base on the proportion of tumors expressing the TSA (upper half and lower half). FIG. 11B: Correlation between aeTSA number and chromosome arm amplification. Scatter plot shows the Pearson correlation between chromosome arm amplification (x axis) and aeTSA number identified from the arm (y axis) for each sample.

DETAILED DISCLOSURE

Terms and symbols of genetics, molecular biology, biochemistry and nucleic acid used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

In the studies described herein, the present inventors have identified 111 TSA candidates (103 novel and 8 previously reported) from 23 HGSC tumors using a proteogenomic-based approach. A large fraction of these TSAs (93) derived from aberrantly expressed unmutated genomic sequences which are not expressed in normal tissues. These aberrantly expressed TSAs (referred to herein as aeTSAs) were shown to be derived primarily from non-exonic sequences, in particular intronic (31%) and intergenic (22%), and their expression was regulated at the transcriptional level by variations in gene copy number and DNA methylation.

These aeTSAs were shared by a large proportion of HGSCs, and taking into account the frequency of aeTSA expression and HLA allele frequencies, it was estimated that, in Caucasians, the median number of aeTSAs per tumor would be five. The novel TSA candidates identified herein may be useful for ovarian cancer T-cell based immunotherapy.

Accordingly, in an aspect, the present disclosure relates to a tumor antigen peptide (or tumor-specific peptide) comprising, or consisting of, one of the amino acid sequences of SEQ ID NOs: 1-103, preferably SEQ ID NOs: 19-103 (Tables 3A, 3B).

In an embodiment, the present disclosure relates to a tumor antigen peptide encoded by a sequence located in an untranslated transcribed region (UTR), i.e. a 3'-UTR or 5'-UTR region, comprising, or consisting of, one of the amino acid sequences of SEQ ID NOs: 1, 8, 10, 13, 15, and 19-27, preferably SEQ ID NOs: 19-27. In an embodiment, the tumor antigen peptide is encoded by a sequence located in a 5'-UTR and comprises or consists of one of the amino acid sequences of SEQ ID NOs: 1, 10, 13, 15, and 19-23, preferably SEQ ID NOs: 19-23. In an embodiment, the tumor antigen peptide is encoded by a sequence located in a 3'-UTR and comprises or consists of one of the amino acid sequences of SEQ ID NOs: 8, and 24-27, preferably SEQ ID NOs: 24-27.

In an embodiment, the present disclosure relates to a tumor antigen peptide encoded by a sequence located in an intron comprising, or consisting of, one of the amino acid sequences of SEQ ID NOs: 16, 17 and 36-64, preferably SEQ ID NOs: 36-64.

In an embodiment, the present disclosure relates to a tumor antigen peptide encoded by a sequence located in an intergenic region comprising, or consisting of, one of the amino acid sequences of SEQ ID NOs: 65-84.

In another embodiment, the present disclosure relates to a tumor antigen peptide encoded by a sequence located in an exon and originates from a frameshift comprising, or consisting of, one of the amino acid sequences of SEQ ID NOs: 6, 7, 18 and 28-35, preferably SEQ ID NOs: 28-35.

In another embodiment, the present disclosure relates to a tumor antigen peptide encoded by a non-coding RNA sequence (ncRNA) (is located in the exons of a noncoding transcript) comprising, or consisting of, one of the amino acid sequences of SEQ ID NOs: 4 and 85-92, preferably SEQ ID NOs: 85-92.

In another embodiment, the present disclosure relates to a tumor antigen peptide encoded by a sequence that is antisense of a gene comprising, or consisting of, one of the amino acid sequences of SEQ ID NOs: 93-99.

In another embodiment, the present disclosure relates to a tumor antigen peptide encoded by a sequence from a mucin gene comprising, or consisting of, one of the amino acid sequences of SEQ ID NOs: 100-103.

In general, peptides such as tumor antigen peptides presented in the context of HLA class I vary in length from about 7 or 8 to about 15, or preferably 8 to 14 amino acid residues. In some embodiments of the methods of the disclosure, longer peptides comprising the tumor antigen peptide sequences defined herein are artificially loaded into cells such as antigen presenting cells (APCs), processed by the cells and the tumor antigen peptide is presented by MHC class I molecules at the surface of the APC. In this method, peptides/polypeptides longer than 15 amino acid residues (i.e. a tumor antigen precursor peptide) can be loaded into APCs, are processed by proteases in the APC cytosol providing the corresponding tumor antigen peptide as defined herein for presentation. In some embodiments, the precursor peptide/polypeptide that is used to generate the tumor antigen peptide defined herein is for example 1000, 500, 400, 300, 200, 150, 100, 75, 50, 45, 40, 35, 30, 25, 20 or 15 amino acids or less. Thus, all the methods and processes using the tumor antigen peptides described herein include the use of longer peptides or polypeptides (including the native protein), i.e. tumor antigen precursor peptides/polypeptides, to induce the presentation of the "final" 8-14 tumor antigen peptide following processing by the cell (APCs). In some embodiments, the herein-mentioned tumor antigen peptide is about 8 to 14, 8 to 13, or 8 to 12 amino acids long (e.g., 8, 9, 10, 11, 12 or 13 amino acids long), small enough for a direct fit in an HLA class I molecule. In an embodiment, the tumor antigen peptide comprises 20 amino acids or less, preferably 15 amino acids or less, more preferably 14 amino acids or less. In an embodiment, the tumor antigen peptide comprises at least 7 amino acids, preferably at least 8 amino acids, more preferably at least 9 amino acids.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of tumor antigen peptides. Examples of naturally occurring amino acids are glycine, alanine, valine, leucine, isoleucine, serine, threonine, etc. Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-di-aminopropionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienyl-alanine, methionine sulfoxide, L-homoarginine (Hoarg), N-acetyl lysine, 2-amino butyric acid, 2-amino butyric acid, 2,4,-diaminobutyric acid (D- or L-), p-aminophenylalanine, N-methylvaline, homocysteine, homoserine (HoSer), cystic acid, epsilon-amino hexanoic acid, delta-amino valeric acid, or 2,3-diaminobutyric acid (D- or L-), etc. These amino acids are well known in the art of biochemistry/peptide chemistry. In an embodiment, the tumor antigen peptide comprises only naturally-occurring amino acids.

In embodiments, the tumor antigen peptides described herein include peptides with altered sequences containing substitutions of functionally equivalent amino acid residues, relative to the herein-mentioned sequences. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. The herein-mentioned tumor antigen peptide may comprise all L-amino acids, all D-amino acids or a mixture of L- and D-amino acids. In an embodiment, the herein-mentioned tumor antigen peptide comprises all L-amino acids.

In an embodiment, in the sequences of the tumor antigen peptides comprising or consisting of one of sequences disclosed in Tables 3A-3B, the amino acid residues that do not substantially contribute to interactions with the T-cell receptor may be modified by replacement with other amino acid whose incorporation does not substantially affect T-cell reactivity and does not eliminate binding to the relevant MHC.

The tumor antigen peptide may also be N- and/or C-terminally capped or modified to prevent degradation, increase stability, affinity and/or uptake. Thus, in another aspect, the present disclosure provides a modified tumor antigen peptide of the formula $Z^1$—X—$Z^2$, wherein X is a tumor antigen peptide comprising, or consisting of, one of the amino acid sequences of SEQ ID NOs: 1-103, preferably SEQ ID NOs: 19-103 (Tables 3A, 3B).

In an embodiment, the amino terminal residue (i.e., the free amino group at the N-terminal end) of the tumor antigen peptide is modified (e.g., for protection against degradation), for example by covalent attachment of a moiety/chemical group ($Z^1$). $Z^1$ may be a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In an embodiment, $Z^1$ is absent. The carboxy terminal residue (i.e., the free carboxy group at the C-terminal end of the tumor antigen peptide) of the tumor antigen peptide may be modified (e.g., for protection against degradation), for example by amidation (replacement of the OH group by a $NH_2$ group), thus in such a case $Z^2$ is a $NH_2$ group. In an embodiment, $Z^2$ may be an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In an embodiment, $Z^2$ is absent. In an embodiment, the tumor antigen peptide comprises one of the amino acid sequences of SEQ ID NOs: 1-103, preferably SEQ ID NOs: 19-103 (Tables 3A, 3B). In an embodiment, the tumor antigen peptide consists of one of the amino acid sequences of SEQ ID NOs: 1-103, preferably SEQ ID NOs: 19-103 (Tables 3A, 3B), i.e. wherein $Z^1$ and $Z^2$ are absent.

In another aspect, the present disclosure provides a tumor antigen peptide (or tumor-specific peptide), preferably an ovarian tumor antigen peptide, binding to an HLA-A*01:01 molecule, comprising or consisting of the sequence of SEQ ID NO: 21, 28, 40, 41, 66 or 88.

In another aspect, the present disclosure provides a tumor antigen peptide (or tumor-specific peptide), preferably an ovarian tumor antigen peptide, binding to an HLA-A*02:01 molecule, comprising or consisting of the sequence of SEQ ID NO: 14, 17, 45, 48, 51, 56, 75, 77, 82, 98 or 100, preferably SEQ ID NOs: 45, 48, 51, 56, 75, 77, 82, 98 or 100.

In another aspect, the present disclosure provides a tumor antigen peptide (or tumor-specific peptide), preferably an ovarian tumor antigen peptide, binding to an HLA-A*03:01 molecule, comprising or consisting of the sequence of SEQ ID NOs: 1, 19, 20, 22, 30, 31, 36, 50, 52, 60, 62, 73, 84, 85, 86 or 91, preferably SEQ ID NOs: 19, 20, 22, 30, 31, 36, 50, 52, 60, 62, 73, 84, 85, 86 or 91.

In another aspect, the present disclosure provides a tumor antigen peptide (or tumor-specific peptide), preferably an ovarian tumor antigen peptide, binding to an HLA-A*11:01 molecule, comprising or consisting of the sequence of SEQ ID NO: 32, 54, 55, 67, 69, 81, 87, 90 or 102.

In another aspect, the present disclosure provides a tumor antigen peptide (or tumor-specific peptide), preferably an ovarian tumor antigen peptide, binding to an HLA-A*24:02 molecule, comprising or consisting of the sequence of SEQ ID NO: 33 or 43.

In another aspect, the present disclosure provides a tumor antigen peptide (or tumor-specific peptide), preferably an ovarian tumor antigen peptide, binding to an HLA-A*25:01 molecule, comprising or consisting of the sequence of SEQ ID NO: 24.

In another aspect, the present disclosure provides a tumor antigen peptide (or tumor-specific peptide), preferably an ovarian tumor antigen peptide, binding to an HLA-A*29:02 molecule, comprising or consisting of the sequence of SEQ ID NO: 34 or 58.

In another aspect, the present disclosure provides a tumor antigen peptide (or tumor-specific peptide), preferably an ovarian tumor antigen peptide, binding to an HLA-A*32:01 molecule, comprising or consisting of the sequence of SEQ ID NO: 16.

In another aspect, the present disclosure provides a tumor antigen peptide (or tumor-specific peptide), preferably an ovarian tumor antigen peptide, binding to an HLA-B*07:02 molecule, comprising or consisting of the sequence of SEQ ID NO: 4, 6, 8, 9, 26, 49, 78, 92, 97 or 101, preferably SEQ ID NOs: 26, 49, 78, 92, 97 or 101.

In another aspect, the present disclosure provides a tumor antigen peptide (or tumor-specific peptide), preferably an ovarian tumor antigen peptide, binding to an HLA-B*08:01 molecule, comprising or consisting of the sequence of SEQ ID NO: 23, 35, 42, 44, 46, 59, 63, 70, 74, 76, 83 or 103.

In another aspect, the present disclosure provides a tumor antigen peptide (or tumor-specific peptide), preferably an ovarian tumor antigen peptide, binding to an HLA-B*14:01 molecule, comprising or consisting of the sequence of SEQ ID NO: 53.

In another aspect, the present disclosure provides a tumor antigen peptide (or tumor-specific peptide), preferably an ovarian tumor antigen peptide, binding to an HLA-B*15:01 molecule, comprising or consisting of the sequence of SEQ ID NO: 2, 3 or 5.

In another aspect, the present disclosure provides a tumor antigen peptide (or tumor-specific peptide), preferably an ovarian tumor antigen peptide, binding to an HLA-B*18:01 molecule, comprising or consisting of the sequence of SEQ ID NO: 89.

In another aspect, the present disclosure provides a tumor antigen peptide (or tumor-specific peptide), preferably an ovarian tumor antigen peptide, binding to an HLA-B*39:01 molecule, comprising or consisting of the sequence of SEQ ID NO: 47, 64, 96 or 99.

In another aspect, the present disclosure provides a tumor antigen peptide (or tumor-specific peptide), preferably an ovarian tumor antigen peptide, binding to an HLA-B*40:01 molecule, comprising or consisting of the sequence of SEQ ID NO: 11, 12 or 13.

In another aspect, the present disclosure provides a tumor antigen peptide (or tumor-specific peptide), preferably an ovarian tumor antigen peptide, binding to an HLA-B*44:02 molecule, comprising or consisting of the sequence of SEQ ID NO: 65.

In another aspect, the present disclosure provides a tumor antigen peptide (or tumor-specific peptide), preferably an ovarian tumor antigen peptide, binding to an HLA-B*44:03 molecule, comprising or consisting of the sequence of SEQ ID NO: 37 or 94.

In another aspect, the present disclosure provides a tumor antigen peptide (or tumor-specific peptide), preferably an ovarian tumor antigen peptide, binding to an HLA-C*03:03 molecule, comprising or consisting of the sequence of SEQ ID NO: 10, 29, 71 or 95, preferably SEQ ID NOs: 29, 71 or 95.

In another aspect, the present disclosure provides a tumor antigen peptide (or tumor-specific peptide), preferably an ovarian tumor antigen peptide, binding to an HLA-C*04:01 molecule, comprising or consisting of the sequence of SEQ ID NO: 6 or 15.

In another aspect, the present disclosure provides a tumor antigen peptide (or tumor-specific peptide), preferably an ovarian tumor antigen peptide, binding to an HLA-C*05:01 molecule, comprising or consisting of the sequence of SEQ ID NO: 27.

In another aspect, the present disclosure provides a tumor antigen peptide (or tumor-specific peptide), preferably an ovarian tumor antigen peptide, binding to an HLA-C*06:02 molecule, comprising or consisting of the sequence of SEQ ID NO: 18 or 72, preferably SEQ ID NO: 72.

In another aspect, the present disclosure provides a tumor antigen peptide (or tumor-specific peptide), preferably an ovarian tumor antigen peptide, binding to an HLA-C*07:01 molecule, comprising or consisting of the sequence of SEQ ID NO: 38, 61 or 93.

In another aspect, the present disclosure provides a tumor antigen peptide (or tumor-specific peptide), preferably an ovarian tumor antigen peptide, binding to an HLA-C*07:02 molecule, comprising or consisting of the sequence of SEQ ID NO: 7.

In another aspect, the present disclosure provides a tumor antigen peptide (or tumor-specific peptide), preferably an ovarian tumor antigen peptide, binding to an HLA-C*12:03 molecule, comprising or consisting of the sequence of SEQ ID NO: 80.

In another aspect, the present disclosure provides a tumor antigen peptide (or tumor-specific peptide), preferably an ovarian tumor antigen peptide, binding to an HLA-C*14:02 molecule, comprising or consisting of the sequence of SEQ ID NO: 25, 57 or 79.

In an embodiment, the tumor antigen peptide is encoded by a sequence located in an untranslated transcribed region (UTR), i.e. a 3'-UTR or 5'-UTR region. In another embodiment, the tumor antigen peptide is encoded by a sequence located in an intron. In another embodiment, the tumor antigen peptide is encoded by a sequence located in an intergenic region. In another embodiment, the tumor antigen peptide is encoded by a sequence located in an exon and originates from a frameshift.

The tumor antigen peptides of the disclosure may be produced by expression in a host cell comprising a nucleic acid encoding the tumor antigen peptides (recombinant expression) or by chemical synthesis (e.g., solid-phase peptide synthesis). Peptides can be readily synthesized by manual and/or automated solid phase procedures well known in the art. Suitable syntheses can be performed for example by utilizing "T-boc" or "Fmoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the tumor antigen peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the tumor antigen peptides are described in Nakagawa et al., *J. Am. Chem. Soc.* 107: 7087-7092, 1985. In an embodiment, the tumor antigen peptide is chemically synthesized (synthetic peptide). Another embodiment of the present disclosure relates to a non-naturally occurring peptide wherein said peptide consists or consists essentially of an amino acid sequences defined herein and has been synthetically produced (e.g. synthesized) as a pharmaceutically acceptable salt. The salts of the tumor antigen peptides according to the present disclosure differ substantially from the peptides in their state(s) in vivo, as the peptides as generated in vivo are no salts. The non-natural salt form of the peptide may modulate the solubility of the peptide, in particular in the context of pharmaceutical compositions comprising the peptides, e.g. the peptide vaccines as disclosed herein. Preferably, the salts are pharmaceutically acceptable salts of the peptides.

In an embodiment, the herein-mentioned tumor antigen peptide is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components, e.g.

components of its source macromolecule. A nucleic acid molecule is substantially pure when it is not immediately contiguous with (i.e., covalently linked to) the coding sequences with which it is normally contiguous in the naturally occurring genome of the organism from which the nucleic acid is derived. A substantially pure compound can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc. In an embodiment, the tumor antigen peptide is in solution. In another embodiment, the tumor antigen peptide is in solid form, e.g., lyophilized.

In another aspect, the disclosure further provides a nucleic acid (isolated) encoding the herein-mentioned tumor antigen peptides or a tumor antigen precursor-peptide. In an embodiment, the nucleic acid comprises from about 21 nucleotides to about 45 nucleotides, from about 24 to about 45 nucleotides, for example 24, 27, 30, 33, 36, 39, 42 or 45 nucleotides. "Isolated", as used herein, refers to a peptide or nucleic molecule separated from other components that are present in the natural environment of the molecule or a naturally occurring source macromolecule (e.g., including other nucleic acids, proteins, lipids, sugars, etc.). "Synthetic", as used herein, refers to a peptide or nucleic molecule that is not isolated from its natural sources, e.g., which is produced through recombinant technology or using chemical synthesis. A nucleic acid of the disclosure may be used for recombinant expression of the tumor antigen peptide of the disclosure, and may be included in a vector or plasmid, such as a cloning vector or an expression vector, which may be transfected into a host cell. In an embodiment, the disclosure provides a cloning, expression or viral vector or plasmid comprising a nucleic acid sequence encoding the tumor antigen peptide of the disclosure. Alternatively, a nucleic acid encoding a tumor antigen peptide of the disclosure may be incorporated into the genome of the host cell. In either case, the host cell expresses the tumor antigen peptide or protein encoded by the nucleic acid. The term "host cell" as used herein refers not only to the particular subject cell, but to the progeny or potential progeny of such a cell. A host cell can be any prokaryotic (e.g., *E. coli*) or eukaryotic cell (e.g., insect cells, yeast or mammalian cells) capable of expressing the tumor antigen peptides described herein. The vector or plasmid contains the necessary elements for the transcription and translation of the inserted coding sequence, and may contain other components such as resistance genes, cloning sites, etc. Methods that are well known to those skilled in the art may be used to construct expression vectors containing sequences encoding peptides or polypeptides and appropriate transcriptional and translational control/regulatory elements operably linked thereto. These methods include in vitro recombinant DNA techniques, synthetic techniques, and in vivo genetic recombination. Such techniques are described in Sambrook. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y. "Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences. "Regulatory/control region" or "regulatory/control sequence", as used herein, refers to the non-coding nucleotide sequences that are involved in the regulation of the expression of a coding nucleic acid. Thus, the term regulatory region includes promoter sequences, regulatory protein binding sites, upstream activator sequences, and the like. In an embodiment, the nucleic acid (DNA, RNA) encoding the tumor antigen peptide of the disclosure is comprised within or attached to a liposome or any other suitable vehicle.

In another aspect, the present disclosure provides an MHC class I molecule comprising (i.e. presenting or bound to) a tumor antigen peptide. In an embodiment, the MHC class I molecule is an HLA-A1 molecule, in a further embodiment an HLA-A*01:01 molecule. In another embodiment, the MHC class I molecule is an HLA-A2 molecule, in a further embodiment an HLA-A*02:01 molecule. In another embodiment, the MHC class I molecule is an HLA-A3 molecule, in a further embodiment an HLA-A*03:01 molecule. In another embodiment, the MHC class I molecule is an HLA-A11 molecule, in a further embodiment an HLA-A*11:01 molecule. In another embodiment, the MHC class I molecule is an HLA-A24 molecule, in a further embodiment an HLA-A*24:02 molecule. In another embodiment, the MHC class I molecule is an HLA-A25 molecule, in a further embodiment an HLA-A*25:01 molecule. In another embodiment, the MHC class I molecule is an HLA-A29 molecule, in a further embodiment an HLA-A*29:02 molecule. In another embodiment, the MHC class I molecule is an HLA-A32 molecule, in a further embodiment an HLA-A*32:02 molecule. In another embodiment, the MHC class I molecule is an HLA-B07 molecule, in a further embodiment an HLA-B*07:02 molecule. In another embodiment, the MHC class I molecule is an HLA-B08 molecule, in a further embodiment an HLA-B*08:01 molecule. In another embodiment, the MHC class I molecule is an HLA-B14 molecule, in a further embodiment an HLA-B*14:01 molecule. In another embodiment, the MHC class I molecule is an HLA-B15 molecule, in a further embodiment an HLA-B*15:01 molecule. In another embodiment, the MHC class I molecule is an HLA-B18 molecule, in a further embodiment an HLA-B*18:01 molecule. In another embodiment, the MHC class I molecule is an HLA-B39 molecule, in a further embodiment an HLA-B*39:01 molecule. In another embodiment, the MHC class I molecule is an HLA-B40 molecule, in a further embodiment an HLA-B*40:01 molecule. In another embodiment, the MHC class I molecule is an HLA-B44 molecule, in a further embodiment an HLA-B*44:02 or HLA-B*44:03 molecule. In another embodiment, the MHC class I molecule is an HLA-C03 molecule, in a further embodiment an HLA-C*03:03 molecule. In another embodiment, the MHC class I molecule is an HLA-C04 molecule, in a further embodiment an HLA-C*04:01 molecule. In another embodiment, the MHC class I molecule is an HLA-C05 molecule, in a further embodiment an HLA-C*05:01 molecule. In another embodiment, the MHC class I molecule is an HLA-C06 molecule, in a further embodiment an HLA-C*06:02 molecule. In another embodiment, the MHC class I molecule is an HLA-C07 molecule, in a further embodiment an HLA-C*07:01 or HLA-C*07:02 molecule. In another embodiment, the MHC class I molecule is an HLA-C12 molecule, in a further embodiment an HLA-C*12:03 molecule. In another embodiment, the MHC class I molecule is an HLA-C14 molecule, in a further embodiment an HLA-C*14:02 molecule.

In an embodiment, the tumor antigen peptide is non-covalently bound to the MHC class I molecule (i.e., the tumor antigen peptide is loaded into, or non-covalently bound to the peptide binding groove/pocket of the MHC class I molecule). In another embodiment, the tumor antigen peptide is covalently attached/bound to the MHC class I molecule (alpha chain). In such a construct, the tumor antigen peptide and the MHC class I molecule (alpha chain) are produced as a synthetic fusion protein, typically with a short (e.g., 5 to 20 residues, preferably about 8-12, e.g., 10) flexible linker or spacer (e.g., a polyglycine linker). In another aspect, the disclosure provides a nucleic acid encoding a fusion protein comprising a tumor antigen peptide defined herein fused to a MHC class I molecule (alpha chain). In an embodiment, the MHC class I molecule (alpha chain)—peptide complex is multimerized. Accordingly, in another aspect, the present disclosure provides a multimer of MHC class I molecule loaded (covalently or not) with the herein-mentioned tumor antigen peptide. Such multimers may be attached to a tag, for example a fluorescent tag, which allows the detection of the multimers. A great number of strategies have been developed for the production of MHC multimers, including MHC dimers, tetramers, pentamers, octamers, etc. (reviewed in Bakker and Schumacher, *Current Opinion in Immunology* 2005, 17:428-433). MHC multimers are useful, for example, for the detection and purification of antigen-specific T cells. Thus, in another aspect, the present disclosure provides a method for detecting or purifying (isolating, enriching) CD8$^+$ T lymphocytes specific for a tumor antigen peptide defined herein, the method comprising contacting a cell population with a multimer of MHC class I molecule loaded (covalently or not) with the tumor antigen peptide; and detecting or isolating the CD8$^+$ T lymphocytes bound by the MHC class I multimers. CD8$^+$ T lymphocytes bound by the MHC class I multimers may be isolated using known methods, for example fluorescence activated cell sorting (FACS) or magnetic activated cell sorting (MACS).

In yet another aspect, the present disclosure provides a cell (e.g., a host cell), in an embodiment an isolated cell, comprising the herein-mentioned nucleic acid, vector or plasmid of the disclosure, i.e. a nucleic acid or vector encoding one or more tumor antigen peptides. In another aspect, the present disclosure provides a cell expressing at its surface an MHC class I molecule (e.g., an MHC class I molecule of one of the alleles disclosed above) bound to or presenting a tumor antigen peptide according to the disclosure. In one embodiment, the host cell is a eukaryotic cell, such as a mammalian cell, preferably a human cell. a cell line or an immortalized cell. In another embodiment, the cell is an antigen-presenting cell (APC). In one embodiment, the host cell is a primary cell, a cell line or an immortalized cell. In another embodiment, the cell is an antigen-presenting cell (APC). Nucleic acids and vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing nucleic acids into mammalian cells in vivo are also known, and may be used to deliver the vector or plasmid of the disclosure to a subject for gene therapy.

Cells such as APCs can be loaded with one or more tumor antigen peptides using a variety of methods known in the art. As used herein "loading a cell" with a tumor antigen peptide means that RNA or DNA encoding the tumor antigen peptide, or the tumor antigen peptide, is transfected into the cells or alternatively that the APC is transformed with a nucleic acid encoding the tumor antigen peptide. The cell can also be loaded by contacting the cell with exogenous tumor antigen peptides that can bind directly to MHC class I molecule present at the cell surface (e.g., peptide-pulsed cells). The tumor antigen peptides may also be fused to a domain or motif that facilitates its presentation by MHC class I molecules, for example to an endoplasmic reticulum (ER) retrieval signal, a C-terminal Lys-Asp-Glu-Leu sequence (see Wang et al., *Eur J Immunol.* 2004 December; 34(12):3582-94).

In another aspect, the present disclosure provides a composition or peptide combination/pool comprising any one of, or any combination of, the tumor antigen peptides defined herein (or a nucleic acid encoding said peptide(s)). In an embodiment, the composition comprises any combination of the tumor antigen peptides defined herein (any combination of 2, 3, 4, 5, 6, 7, 8, 9, 10 or more tumor antigen peptides), or a combination of nucleic acids encoding said tumor antigen peptides). Compositions comprising any combination/sub-combination of the tumor antigen peptides defined herein are encompassed by the present disclosure. In another embodiment, the combination or pool may comprise one or more known tumor antigens.

Thus, in another aspect, the present disclosure provides a composition comprising any one of, or any combination of, the tumor antigen peptides defined herein and a cell expressing a MHC class I molecule (e.g., a MHC class I molecule of one of the alleles disclosed above). APC for use in the present disclosure are not limited to a particular type of cell and include professional APCs such as dendritic cells (DCs), Langerhans cells, macrophages and B cells, which are known to present proteinaceous antigens on their cell surface so as to be recognized by CD8+ T lymphocytes. For example, an APC can be obtained by inducing DCs from peripheral blood monocytes and then contacting (stimulating) the tumor antigen peptides, either in vitro, ex vivo or in vivo. APC can also be activated to present a tumor antigen peptide in vivo where one or more of the tumor antigen peptides of the disclosure are administered to a subject and APCs that present a tumor antigen peptide are induced in the body of the subject. The phrase "inducing an APC" or "stimulating an APC" includes contacting or loading a cell with one or more tumor antigen peptides, or nucleic acids encoding the tumor antigen peptides such that the tumor antigen peptides are presented at its surface by MHC class I molecules. As noted herein, according to the present disclosure, the tumor antigen peptides may be loaded indirectly for example using longer peptides/polypeptides comprising the sequence of the tumor antigen peptides (including the native protein), which is then processed (e.g., by proteases) inside the APCs to generate the tumor antigen peptide/MHC class I complexes at the surface of the cells. After loading APCs with tumor antigen peptides and allowing the APCs to present the tumor antigen peptides, the APCs can be administered to a subject as a vaccine. For example, the ex vivo administration can include the steps of: (a) collecting APCs from a first subject, (b) contacting/loading the APCs of step (a) with a tumor antigen peptide to form MHC class I/tumor antigen peptide complexes at the surface of the APCs; and (c) administering the peptide-loaded APCs to a second subject in need for treatment.

The first subject and the second subject may be the same subject (e.g., autologous vaccine), or may be different subjects (e.g., allogeneic vaccine). Alternatively, according to the present disclosure, use of a tumor antigen peptide described herein (or a combination thereof) for manufacturing a composition (e.g., a pharmaceutical composition) for inducing antigen-presenting cells is provided. In addition, the present disclosure provides a method or process for manufacturing a pharmaceutical composition for inducing antigen-presenting cells, wherein the method or the process includes the step of admixing or formulating the tumor antigen peptide, or a combination thereof, with a pharmaceutically acceptable carrier. Cells such as APCs expressing a MHC class I molecule (e.g., HLA-A1, HLA-A2, HLA-A3, HLA-A11, HLA-A24, HLA-A25, HLA-A29, HLA-A32, HLA-B07, HLA-B08, HLA-B14, HLA-B15, HLA-B18, HLA-B39, HLA-B40, HLA-B44, HLA-C03, HLA-C04, HLA-C05, HLA-C06, HLA-C07, HLA-C12, or HLA-C14 molecule) loaded with any one of, or any combination of, the tumor antigen peptides defined herein, may be used for stimulating/amplifying CD8+ T lymphocytes, for example autologous CD8+ T lymphocytes. Accordingly, in another aspect, the present disclosure provides a composition comprising any one of, or any combination of, the tumor antigen peptides defined herein (or a nucleic acid or vector encoding same); a cell expressing an MHC class I molecule and a T lymphocyte, more specifically a CD8+ T lymphocyte (e.g., a population of cells comprising CD8+ T lymphocytes).

In an embodiment, the composition further comprises a buffer, an excipient, a carrier, a diluent and/or a medium (e.g., a culture medium). In a further embodiment, the buffer, excipient, carrier, diluent and/or medium is/are pharmaceutically acceptable buffer(s), excipient(s), carrier(s), diluent(s) and/or medium (media). As used herein "pharmaceutically acceptable buffer, excipient, carrier, diluent and/or medium" includes any and all solvents, buffers, binders, lubricants, fillers, thickening agents, disintegrants, plasticizers, coatings, barrier layer formulations, lubricants, stabilizing agent, release-delaying agents, dispersion media, coatings, antibacterial and antifungal agents, isotonic agents, and the like that are physiologically compatible, do not interfere with effectiveness of the biological activity of the active ingredient(s) and that are not toxic to the subject. The use of such media and agents for pharmaceutically active substances is well known in the art (Rowe et al., Handbook of pharmaceutical excipients, 2003, 4th edition, Pharmaceutical Press, London UK). Except insofar as any conventional media or agent is incompatible with the active compound (peptides, cells), use thereof in the compositions of the disclosure is contemplated. In an embodiment, the buffer, excipient, carrier and/or medium is a non-naturally occurring buffer, excipient, carrier and/or medium. In an embodiment, one or more of the tumor antigen peptides defined herein, or the nucleic acids (e.g., mRNAs) encoding said one or more tumor antigen peptides, are comprised within or complexed to a liposome, e.g., a cationic liposome (see, e.g., Vitor M T et al., Recent Pat Drug Deliv Formul. 2013 August; 7(2):99-110).

In another aspect, the present disclosure provides a composition comprising one of more of the any one of, or any combination of, the tumor antigen peptides defined herein (or a nucleic acid encoding said peptide(s)), and a buffer, an excipient, a carrier, a diluent and/or a medium. For compositions comprising cells (e.g., APCs, T lymphocytes), the composition comprises a suitable medium that allows the maintenance of viable cells. Representative examples of such media include saline solution, Earl's Balanced Salt Solution (Life Technologies®) or PlasmaLyte® (Baxter International®). In an embodiment, the composition (e.g., pharmaceutical composition) is an "immunogenic composition", "vaccine composition" or "vaccine". The term "Immunogenic composition", "vaccine composition" or "vaccine" as used herein refers to a composition or formulation comprising one or more tumor antigen peptides or vaccine vector and which is capable of inducing an immune response against the one or more tumor antigen peptides present therein when administered to a subject. Vaccination methods for inducing an immune response in a mammal comprise use of a vaccine or vaccine vector to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch). In an embodiment, the tumor antigen peptide (or a combination thereof) is conjugated to a carrier protein (conjugate vaccine) to increase the immunogenicity of the tumor antigen peptide(s). The present disclosure thus provides a composition (conjugate) comprising a tumor antigen peptide (or a combination thereof), or a nucleic acid encoding the tumor antigen peptide or combination thereof, and a carrier protein. For example, the tumor antigen peptide(s) or nucleic acid(s) may be conjugated or complexed to a Toll-like receptor (TLR) ligand (see, e.g., Zom et al., *Adv Immunol.* 2012, 114: 177-201) or polymers/dendrimers (see, e.g., Liu et al., *Biomacromolecules.* 2013 Aug. 12; 14(8): 2798-806). In an embodiment, the immunogenic composition or vaccine further comprises an adjuvant. "Adjuvant" refers to a substance which, when added to an immunogenic agent such as an antigen (tumor antigen peptides, nucleic acids and/or cells according to the present disclosure), nonspecifically enhances or potentiates an immune response to the agent in the host upon exposure to the mixture. Examples of adjuvants currently used in the field of vaccines include (1) mineral salts (aluminum salts such as aluminum phosphate and aluminum hydroxide, calcium phosphate gels), squalene, (2) oil-based adjuvants such as oil emulsions and surfactant based formulations, e.g., MF59 (microfluidised detergent stabilised oil-in-water emulsion), QS21 (purified saponin), ASO2 [SBAS2] (oil-in-water emulsion+MPL+QS-21), (3) particulate adjuvants, e.g., virosomes (unilamellar liposomal vehicles incorporating influenza haemagglutinin), ASO4 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+M. *Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles, and the like.

In an embodiment, the tumor antigen peptide(s) or composition comprising same is/are in lyophilized form. In another embodiment, the tumor antigen peptide(s) or composition comprising same is/are in a liquid composition. In a further embodiment, the tumor antigen peptide(s) is/are at a concentration of about 0.01 μg/mL to about 100 μg/mL in the composition. In further embodiments, the tumor antigen peptide(s) is/are at a concentration of about 0.2 μg/mL to about 50 μg/mL, about 0.5 μg/mL to about 10, 20, 30, 40 or 50 μg/mL, about 1 μg/mL to about 10 μg/mL, or about 2 μg/mL, in the composition.

As noted herein, cells such as APCs that express an MHC class I molecule loaded with or bound to any one of, or any combination of, the tumor antigen peptides defined herein, may be used for stimulating/amplifying CD8$^+$ T lymphocytes in vivo or ex vivo. Accordingly, in another aspect, the present disclosure provides T cell receptor (TCR) molecules capable of interacting with or binding the herein-mentioned MHC class I molecule/tumor antigen peptide complex, and nucleic acid molecules encoding such TCR molecules, and vectors comprising such nucleic acid molecules. A TCR according to the present disclosure is capable of specifically interacting with or binding a tumor antigen peptide loaded on, or presented by, an MHC class I molecule, preferably at the surface of a living cell in vitro or in vivo. A TCR and in particular nucleic acids encoding a TCR of the disclosure may for instance be applied to genetically transform/modify T lymphocytes (e.g., CD8$^+$ T lymphocytes) or other types of lymphocytes generating new T lymphocyte clones that specifically recognize an MHC class I/tumor antigen peptide complex. In a particular embodiment, T lymphocytes (e.g., CD8$^+$ T lymphocytes) obtained from a patient are transformed to express one or more TCRs that recognize a tumor antigen peptide and the transformed cells are administered to the patient (autologous cell transfusion). In a particular embodiment, T lymphocytes (e.g., CD8$^+$ T lymphocytes) obtained from a donor are transformed to express one or more TCRs that recognize a tumor antigen peptide and the transformed cells are administered to a recipient (allogenic cell transfusion). In another embodiment, the disclosure provides a T lymphocyte e.g., a CD8$^+$ T lymphocyte transformed/transfected by a vector or plasmid encoding a tumor antigen peptide-specific TCR. In a further embodiment the disclosure provides a method of treating a patient with autologous or allogenic cells transformed with a tumor antigen peptide-specific TCR. In yet a further embodiment the use of a tumor antigen-specific TCR in the manufacture of autologous or allogenic cells for the treating of cancer is provided.

In some embodiments, patients treated with the compositions (e.g., pharmaceutical compositions) of the disclosure are treated prior to or following treatment with allogenic stem cell transplant (ASCL), allogenic lymphocyte infusion or autologous lymphocyte infusion. Compositions of the disclosure include: allogenic T lymphocytes (e.g., CD8$^+$ T lymphocyte) activated ex vivo against a tumor antigen peptide; allogenic or autologous APC vaccines loaded with a tumor antigen peptide; tumor antigen peptide vaccines and allogenic or autologous T lymphocytes (e.g., CD8$^+$ T lymphocyte) or lymphocytes transformed with a tumor antigen-specific TCR. The method to provide T lymphocyte clones capable of recognizing a tumor antigen peptide according to the disclosure may be generated for and can be specifically targeted to tumor cells expressing the tumor antigen peptide in a subject (e.g., graft recipient), for example an ASCT and/or donor lymphocyte infusion (DLI) recipient. Hence the disclosure provides a CD8$^+$ T lymphocyte encoding and expressing a T cell receptor capable of specifically recognizing or binding a tumor antigen peptide/MHC class I molecule complex. Said T lymphocyte (e.g., CD8$^+$ T lymphocyte) may be a recombinant (engineered) or a naturally selected T lymphocyte. This specification thus provides at least two methods for producing CD8$^+$ T lymphocytes of the disclosure, comprising the step of bringing undifferentiated lymphocytes into contact with a tumor antigen peptide/MHC class I molecule complex (typically expressed at the surface of cells, such as APCs) under conditions conducive of triggering T cell activation and expansion, which may be done in vitro or in vivo (i.e. in a patient administered with a APC vaccine wherein the APC is loaded with a tumor antigen peptide or in a patient treated with a tumor antigen peptide vaccine). Using a combination or pool of tumor antigen peptides bound to MHC class I molecules, it is possible to generate a population CD8$^+$ T lymphocytes capable of recognizing a plurality of tumor antigen peptides. Alternatively, tumor antigen-specific or targeted T lymphocytes may be produced/generated in vitro or ex vivo by cloning one or more nucleic acids (genes) encoding a TCR (more specifically the alpha and beta chains) that specifically binds to a MHC class I molecule/tumor antigen peptide complex (i.e. engineered or recombinant CD8$^+$ T lymphocytes). Nucleic acids encoding a tumor antigen peptide-specific TCR of the disclosure, may be obtained using methods known in the art from a T lymphocyte activated against a tumor antigen peptide ex vivo (e.g., with an APC loaded with a tumor antigen peptide); or from an individual exhibiting an immune response against peptide/MHC molecule complex. tumor antigen peptide-specific TCRs of the disclosure may be recombinantly expressed in a host cell and/or a host lymphocyte obtained from a graft recipient or graft donor, and optionally differentiated in vitro to provide cytotoxic T lymphocytes (CTLs). The nucleic acid(s) (transgene(s)) encoding the TCR alpha and beta chains may be introduced into a T cells (e.g., from a subject to be treated or another individual) using any suitable methods such as transfection (e.g., electroporation) or transduction (e.g., using viral vector). The engineered CD8$^+$ T lymphocytes expressing a TCR specific for a tumor antigen peptide may be expanded in vitro using well known culturing methods.

The present disclosure provides isolated CD8$^+$ T lymphocytes that are specifically induced, activated and/or amplified (expanded) by a tumor antigen peptide (i.e., a tumor antigen peptide bound to MHC class I molecules expressed at the surface of cell), or a combination of tumor antigen peptides. The present disclosure also provides a composition comprising CD8$^+$ T lymphocytes capable of recognizing a tumor antigen peptide, or a combination thereof, according to the disclosure (i.e., one or more tumor antigen peptides bound to MHC class I molecules) and said tumor antigen peptide(s). In another aspect, the present disclosure provides a cell population or cell culture (e.g., a CD8$^+$ T lymphocyte population) enriched in CD8$^+$ T lymphocytes that specifically recognize one or more MHC class I molecule/tumor antigen peptide complex(es) as described herein. Such enriched population may be obtained by performing an ex vivo expansion of specific T lymphocytes using cells such as APCs that express MHC class I molecules loaded with (e.g. presenting) one or more of the tumor antigen peptides disclosed herein. "Enriched" as used herein means that the proportion of tumor antigen-specific CD8$^+$ T lymphocytes in the population is significantly higher relative to a native population of cells, i.e. which has not been subjected to a step of ex vivo-expansion of specific T lymphocytes. In a further embodiment, the proportion of tumor antigen peptide-specific CD8$^+$ T lymphocytes in the cell population is at least about 0.5%, for example at least about 0.6%, 0.7%, 0.8%, 0.9%, 1%, 1.5%, 2% or 3%. In some embodiments, the proportion of tumor antigen peptide-specific CD8$^+$ T lymphocytes in the cell population is about 0.5 to about 10%, about 0.5 to about 8%, about 0.5 to about 5%, about 0.5 to about 4%, about 0.5 to about 3%, about 1% to about 5%, about 1% to about 4%, about 1% to about 3%, about 2% to about 5%, about 2% to about 4%, about 2% to about 3%, about 3% to about 5% or about 3% to about 4%. Such cell population or culture (e.g., a CD8$^+$ T lymphocyte population) enriched in CD8$^+$ T lymphocytes that specifically recognizes one or more MHC class I molecule/peptide (tumor antigen peptide) complex(es) of interest may be used in tumor antigen-based cancer immunotherapy, as detailed below. In some embodiments, the population of tumor antigen peptide-specific CD8$^+$ T lymphocytes is further enriched, for example using affinity-based systems such as multimers of MHC class I molecule loaded (covalently or not) with the tumor antigen peptide(s) defined herein. Thus, the present disclosure provides a purified or isolated population of tumor antigen peptide-specific CD8$^+$ T lymphocytes, e.g., in which the proportion of tumor antigen peptide-specific CD8$^+$ T lymphocytes is at least about 30%, 40%, 50%, 60%, 70%, 80%, 85%, 90%, 95%, 96%, 97%, 98%, 99% or 100%.

The present disclosure further relates to the use of any tumor antigen peptide, nucleic acid, expression vector, T cell receptor, cell (e.g., T lymphocyte, APC), and/or composition according to the present disclosure, or any combination thereof, as a medicament or in the manufacture of a medicament. In an embodiment, the medicament is for the treatment of cancer, e.g., cancer vaccine. The present disclosure relates to any tumor antigen peptide, nucleic acid, expression vector, T cell receptor, cell (e.g., T lymphocyte, APC), and/or composition (e.g., vaccine composition) according to the present disclosure, or any combination thereof, for use in the treatment of cancer e.g., as a cancer vaccine. The tumor antigen peptide sequences identified herein may be used for the production of synthetic peptides to be used i) for in vitro priming and expansion of tumor antigen-specific T cells to be injected into tumor patients and/or ii) as vaccines to induce or boost the anti-tumor T cell response in cancer patients.

In another aspect, the present disclosure provides the use of a tumor antigen peptide described herein, or a combination thereof (e.g. a peptide pool), as a vaccine for treating cancer in a subject. The present disclosure also provides the tumor antigen peptide described herein, or a combination thereof (e.g. a peptide pool), for use as a vaccine for treating cancer in a subject. In an embodiment, the subject is a recipient of tumor antigen peptide-specific CD8$^+$ T lymphocytes. Accordingly, in another aspect, the present disclosure provides a method of treating cancer (e.g., of reducing the number of tumor cells, killing tumor cells), said method comprising administering (infusing) to a subject in need thereof an effective amount of CD8$^+$ T lymphocytes recognizing (i.e. expressing a TCR that binds) one or more MHC class I molecule/tumor antigen peptide complexes (expressed at the surface of a cell such as an APC). In an embodiment, the method further comprises administering an effective amount of the tumor antigen peptide, or a combination thereof, and/or a cell (e.g., an APC such as a dendritic cell) expressing MHC class I molecule(s) loaded with the tumor antigen peptide(s), to said subject after administration/infusion of said CD8$^+$ T lymphocytes. In yet a further embodiment, the method comprises administering to a subject in need thereof a therapeutically effective amount of a dendritic cell loaded with one or more tumor antigen peptides. In yet a further embodiment the method comprises administering to a patient in need thereof a therapeutically effective amount of an allogenic or autologous cell that expresses a recombinant TCR that binds to a tumor antigen peptide presented by a MHC class I molecule.

In another aspect, the present disclosure provides the use of CD8$^+$ T lymphocytes that recognize one or more MHC class I molecules loaded with (presenting) a tumor antigen peptide, or a combination thereof, for treating cancer (e.g., of reducing the number of tumor cells, killing tumor cells) in a subject. In another aspect, the present disclosure provides the use of CD8$^+$ T lymphocytes that recognize one or more MHC class I molecules loaded with (presenting) a tumor antigen peptide, or a combination thereof, for the preparation/manufacture of a medicament for treating cancer (e.g., for reducing the number of tumor cells, killing tumor cells) in a subject. In another aspect, the present disclosure provides CD8$^+$ T lymphocytes (cytotoxic T lymphocytes) that recognize one or more MHC class I molecule (s) loaded with (presenting) a tumor antigen peptide, or a combination thereof, for use in the treatment of cancer (e.g., for reducing the number of tumor cells, killing tumor cells) in a subject. In a further embodiment, the use further comprises the use of an effective amount of a tumor antigen peptide (or a combination thereof), and/or of a cell (e.g., an APC) that expresses one or more MHC class I molecule(s) loaded with (presenting) a tumor antigen peptide, after the use of said tumor antigen peptide-specific CD8$^+$ T lymphocytes.

The present disclosure also provides a method of generating an immune response against tumor cells expressing human class I MHC molecules loaded with any of the tumor antigen peptide disclosed herein or combination thereof in a subject, the method comprising administering cytotoxic T lymphocytes that specifically recognizes the class I MHC molecules loaded with the tumor antigen peptide or combination of tumor antigen peptides. The present disclosure also provides the use of cytotoxic T lymphocytes that specifically recognizes class I MHC molecules loaded with any of the tumor antigen peptide or combination of tumor antigen peptides disclosed herein for generating an immune response against tumor cells expressing the human class I MHC molecules loaded with the tumor antigen peptide or combination thereof.

In an embodiment, the methods or uses described herein further comprise determining the HLA class I alleles expressed by the patient prior to the treatment/use, and administering or using tumor antigen peptides that bind to one or more of the HLA class I alleles expressed by the patient. For example, if it is determined that the patient expresses HLA-A2*01, HLA-B14*01 and HLA-C05*01, any combinations of the tumor antigen peptides of (i) SEQ ID NOs: 14, 17, 45, 48, 51, 56, 75, 77, 82, 98 and/or 100 (that bind to HLA-A2*01), (ii) SEQ ID NO: 53 (that binds to HLA-B14*01), and/or (iii) SEQ ID NO: 27 (that binds to HLA-C05*01) may be administered or used in the patient.

In an embodiment, the cancer is a solid cancer, preferably an ovarian cancer. In an embodiment, the ovarian cancer is an ovarian carcinoma. In an embodiment, the ovarian cancer is an epithelial carcinoma, a serous carcinoma, a small-cell carcinoma, a primary peritoneal carcinoma, a clear-cell carcinoma or adenocarcinoma, endometrioid adenocarcinoma, malignant mixed mullerian tumor, mucinous adenocarcinoma or cystadenocarcinoma, malignant Brenner tumor, a transitional cell carcinoma, a sex cord-stromal tumor, a granulosa cell tumor, a Sertoli-Leydig tumor, a germ cell tumor, a dysgerminoma, a choriocarcinoma, an immature (solid) or mature teratoma, a yolk sac tumor, squamous cell carcinoma, or a secondary ovarian cancer. In an embodiment, the ovarian cancer is a Type I ovarian cancer. In another embodiment, the ovarian cancer is a Type II ovarian cancer. In an embodiment, the ovarian cancer is a serous carcinoma. In a further embodiment, the serous carcinoma is high-grade serous carcinoma (HGSC). In an embodiment, the ovarian cancer is a stage 1, 11, 111 or IV ovarian cancer.

In an embodiment, the tumor antigen peptide, nucleic acid, expression vector, T cell receptor, cell (e.g., T lymphocyte, APC), and/or composition according to the present disclosure, or any combination thereof, may be used in combination with one or more additional active agents or therapies to treat cancer, such as chemotherapy (e.g., vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, anti-metabolites (such as nucleoside analogs), alkylating agents, platinum-based agents, anthracycline antibiotics, topoisomerase inhibitors, macrolides, retinoids (such as all-trans retinoic acids or a derivatives thereof), geldanamycin or a derivative thereof (such as 17-AAG), surgery, immune checkpoint inhibitors (immunotherapeutic agents (e.g., PD-1/PD-L1 inhibitors and CTLA-4 inhibitors, B7-1/B7-2 inhibitors), antibodies, cell-based therapies (e.g., CAR T cells). In an embodiment, the tumor antigen peptide, nucleic acid, expression vector, T cell receptor, cell (e.g., T lymphocyte, APC), and/or composition according to the present disclosure is administered/used in combination with an immune checkpoint inhibitor.

EXAMPLES

The present disclosure is illustrated in further details by the following non-limiting examples.

Example 1: Materials and Methods

Human HGSC samples. Tumor fragments of HGSC 1~6 and matched normal adjacent tissues of HGSC 1~3 were obtained from Tissue Solutions (Glasgow, GB). Tumortissue (OV606) or ascites (OV633 and OV642) were obtained from the Princess Margaret Cancer Registry (Toronto, ON, Canada). Snap frozen samples were used for RNA extraction and MHCI-associated peptide isolation. RNA sequencing data for OvCa48~114 were downloaded from the National Center for Biotechnology Information Sequence Read Archive under project PRJNA398141, converted to fastq file, and processed like the other samples. MS raw data of the samples in this cohort were downloaded from ProteomeXchange Consortium via the PRIDE partner with identifier PXD007635. HLA typing of each sample was obtained from RNA sequencing (RNA-Seq) data using Opti-Type™ v1.0 with default parameters (24). Sample information is presented in Table 1.

TABLE 1

| Sample name | Sample type | HLA alleles | RNA integrity number | MAPs identified |
|---|---|---|---|---|
| HGSC1 | tumor fragment | A*02:05, A*02:01, B*50:01, B*44:02 C*06:02, C*05:01 | 9.1 | 1610 |
| HGSC2 | tumor fragment | A*02:01, A*03:01 B*35:01, B*27:02 C*04:01, C*02:02 | 9.6 | 1959 |

TABLE 1-continued

| Sample name | Sample type | HLA alleles | RNA integrity number | MAPs identified |
|---|---|---|---|---|
| HGSC3 | tumor fragment | A*11:01, A*02:01 B*07:02, B*15:01 C*07:02, C*03:04 | 9.4 | 5191 |
| HGSC4 | tumor fragment | A*11:01, A*01:01 B*40:01, B*27:05 C*03:04, C*02:02 | 8 | 2752 |
| HGSC5 | tumor fragment | A*02:01, A*03:01 B*15:01, B*56:01 C*03:03, C*01:02 | 7.6 | 2387 |
| HGSC6 | tumor fragment | A*02:01, A*02:01 B*07:02, B*27:05 C*07:02, C*01:02 | 8.9 | 1163 |
| OV606 | tumor fragment | A*01:01, A*03:01 B*08:01, B*51:01 C*07:01, C*12:03 | 6 | 2042 |
| OV633 | CD45- negative HGS Ascites fluid cells | A*02:01 A*24:02 B*44:03 B*57:01 C*04:01 C*07:01 | 7.7 | 3001 |
| OV642 | CD45- negative HGS Ascites fluid cells | A*24:02, A*11:01, B*18:01, B*52:01, C*07:01, C*12:02 | 9.6 | 1492 |

RNA extraction and sequencing. For HGSC 1~6, total RNA was isolated using the AllPrep® DNA/RNA/miRNA Universal kit (Qiagen) as recommended by the manufacturer. For OV606, OV633, and OV642, total RNA was isolated using TRIzol® (Invitrogen). RNA from each sample was assessed on a 2100 Bioanalyzer® (Agilent Genomics) to ensure a RIN>6 and was used to perform one replicate of RNA-Seq per sample. cDNA libraries were prepared from polyA-enriched mRNA using the KAPA Stranded mRNA-Seq Kit. Libraries were further amplified and used for paired-end RNA-Seq on HiSeq® 2000 or Illumina Next-Seq® 500, which yielded 150-300 million reads per sample.

Generation of customized reference databases for MS analyses. For each sample, a customized "global cancer database" was generated by concatenating of two modules, the "canonical cancer proteome" and the "cancer-specific proteome" as previously described (15 and U.S. provisional application No. 62/724,760). Briefly, RNA-Seq reads were trimmed for adapters and low quality 3' bases using Trimmomatic v0.35 (25). To generate canonical cancer proteomes, trimmed reads were aligned to the reference human genome version GRCh38.88 using STAR v2.5.1b. Transcript expression was quantified in transcripts per million (tpm) with kallisto v0.43.0 using default parameters. Nucleotide variants were identified using FreeBayes (26) and converted to an agnostic single-nucleotide polymorphism file format as input for pyGeno (27). A sample-specific proteome for each sample was then built with pyGeno by inserting single-base variants (FreeBayes quality>20) in the reference genome. Sample-specific sequences of expressed proteins (tpm>0) were added into the canonical cancer proteome in a fasta format.

To generate cancer-specific proteomes, trimmed R1 reads were reverse complemented using FASTX-Toolkit version 0.0.14 and were used for 33- and 24-nucleotide-long k-mer databases generation together with trimmed R2 reads. In order to exclude sequencing errors and to limit database size, sample-specific thresholds of minimal k-mer occurrence were applied for 33-nucleotide: 7 for HGSC1~3, 8 for OV642, 10 for OV633, 4 for HGSC4 and OV606, 6 for HGSC5, 5 for HGSC6 and 3 for OvCa48-114. Cancer-specific k-mers were obtained by subtraction of k-mers expressed in human thymic epithelial cells (TECs), then assembled into longer sequences (contigs) by the kmer_assembly tool from NEKTAR (in-house developed software, https://github.com/iric-soft/nektar). Contigs>34 nucleotides long were 3-frame translated into amino acid sequences and split at internal stop codons. The resulting subsequences of at least eight amino acids long were included in the relevant cancer-specific proteome.

Isolation of MAPs. Tumor and tissue samples were cut into small pieces (cubes, ~3 mm in size) and 5 ml of ice-cold PBS containing protein inhibitor cocktail (Sigma, cat #P8340-5 ml) was added. Tissues were first homogenized twice for 20 seconds using an Ultra Turrax™ T25 homogenizer (IKA-Labortechnik) set at speed 20000 rpm and then 20 seconds using an Ultra Turrax™ T8 homogenizer (IKA-Labortechnik) set at speed 25,000 rpm. Then, 550 μl of ice-cold 10× lysis buffer (5% w/v CHAPS) was added to each sample. After 60-minute incubation with tumbling at 4° C., samples were spun at 10000 g for 30 minutes at 4° C. Supernatants were transferred into new tubes containing 1 mg of W6/32 antibody covalently-cross-linked protein A magnetic beads and MAPs were immunoprecipitated as previously described (28). MAP extracts were then dried using a Speed-Vac and kept frozen before MS analyses.

MS analyses. Dried peptide extracts were resuspended in 0.2% formic acid. Peptide extracts were loaded on a home-made C18 analytical column (15 cm×150 μm i.d. packed with C18 Jupiter Phenomenex™) with a 56-min gradient from 0-30% acetonitrile (0.2% formic acid) and a 600 nl·min$^{-1}$ flow rate on an Easy-nLC II system. Samples were analyzed with a Q-Exactive™ HF mass spectrometer (Thermo Fisher Scientific). Each full MS spectrum, acquired with a 60,000 resolution, was followed by 20 MS/MS spectra, where the most abundant multiply charged ions were selected for MS/MS sequencing with a resolution of 30,000, an automatic gain control target of $5×10^4$, an injection time of 100 ms and collision energy of 25%. For HGSC4-6, each full MS spectrum, acquired with a 60,000 resolution, was followed by 20 MS/MS spectra, where the most abundant multiply charged ions were selected for MS/MS sequencing with a resolution of 30,000, an automatic gain control target of $2×10^4$, an injection time of 800 ms and collision energy of 25%.

Identification of MAPs. Peptides were identified using PEAKS 8.5 or Peaks X (Bioinformatics Solution Inc.), and peptide sequences were searched against the global cancer database. For peptide identification, tolerance was set at 10 ppm and 0.01 Da for precursor and fragment ions, respectively. For samples from Schuster et al. (13), tolerance was set at 5 ppm and 0.5 Da for precursor and fragment ions, respectively. The occurrences of oxidation (M) and deamidation (NQ) were considered as post-translational modifications. A sample-specific threshold was applied on the PEAKS score to guaranty that the list of MAPs only included 5% of decoy identifications. Peptides that passed this threshold were further filtered according to the following criteria: peptide length between 8-11 amino acids, and MHC allele affinity rank s 2% based on the prediction of NetMHC4.0 (29).

Identification and validation of TSA candidates. To identify TSA candidates, each MAP and its coding sequence were queried to relevant cancer and normal canonical proteomes or cancer and normal 24-nucleotide-long k-mer databases, respectively. The normal canonical proteome and normal 24-nucleotide-long k-mer database were constructed using RNA-Seq reads from purified TECs harvested from six human thyme (15 and U.S. provisional application No. 62/724,760). MAPs were labeled as TSA candidates in two cases: i) peptide sequences were neither detected in the normal canonical proteome of the sample nor in normal (i.e., TEC) k-mers, or ii) peptides were absent from both cancer and normal canonical proteomes and their RNA coding sequence was overexpressed by at least 10-fold in cancer cells compared to TECs. When a MAP corresponded to several RNA sequences, it was considered as TSA candidate only when all of the sequences were consistent with the TSA candidate status. MS/MS spectra of all TSA candidates were manually validated to remove any false identifications. For TSA candidates with I/L variants supported by RNA data which were distinguishable by MS, both variants were further inspected if the most expressed variant was a TSA candidate.

Finally, a genomic location was assigned to all MS-validated TSA candidates by mapping reads containing MAP-coding sequences on the reference genome (GRCh38) using BLAT (UCSC genome browser). TSA candidates for which reads matched to hypervariable regions (HLA, Ig or TCR genes) were excluded. TSA candidates were classified as mTSAs if they contained variants in their MAP-coding sequences that did not match with known germline polymorphism (reported in dbSNP v149). Non-mutated candidates were classified as aeTSA candidates and subjected to further assessment of their expression in normal tissues and organs.

Tissue expression of sequences coding for aeTSA candidates. RNA-Seq data for 27 different tissues were downloaded from the Genotype-Tissue Expression (GTEx) Portal (accessed on Apr. 16, 2018, phs000424.v7.p2) and were used to assess the expression of the coding sequence of aeTSA candidates, as described previously (15). RNA-Seq data were obtained from 50 donors, except for the cervix (n=6), fallopian tube (n=7), adipose tissue (n=49), bladder (n=12), and kidney (n=38). Accession numbers of the GTEx datasets used in this study are listed in Table 2. Briefly, the number of reads fully covering a MAP-coding sequence was estimated by the minimum occurrence of 24-mer sets of the MAP-coding-sequence in the 24-mer database transformed from RNA-Seq reads of each tissue. Read counts were normalized to reads per hundred million reads sequenced (rphm) and further log transformed ($\log_{10}$(rphm+1)) and averaged across all RNA-Seq experiments available for each tissue. aeTSA candidates exhibiting no peripheral expression at rphm>10 in tissues other than the MHC$^{low}$ tissues (brain cortex, nerve, and testis) were considered as genuine aeTSAs.

TABLE 2

| Tissue group | Accession numbers (SRA) of randomly selected donors |
|---|---|
| other | SRR599313 SRR608150 SRR608198 |
| | SRR612263 SRR612707 SRR612815 |
| | SRR612863 SRR612935 SRR613150 |
| | SRR613234 SRR613342 SRR613390 |
| | SRR613533 SRR613550 |
| other | SRR1069421 SRR1070913 SRR1072626 |
| | SRR1073365 SRR1073775 SRR1074474 |
| | SRR1075314 SRR1076632 SRR1076823 |
| | SRR1082035 SRR1082616 SRR1082733 |
| | SRR1083824 SRR1083892 SRR1085590 |
| | SRR1085951 SRR1086046 SRR1087297 |
| | SRR1087511 SRR1087606 SRR1088365 |
| | SRR1088461 SRR1089479 SRR1089950 |

TABLE 2-continued

| Tissue group | Accession numbers (SRA) of randomly selected donors |
|---|---|
| | SRR1091476 SRR1092160 SRR1092329 |
| | SRR1092686 SRR1093625 SRR1093721 |
| | SRR1093954 SRR1094144 SRR1099378 |
| | SRR1099427 SRR1099598 SRR1099694 |
| | SRR1100496 SRR1100728 SRR808862 |
| | SRR809873 SRR810129 SRR810713 |
| | SRR811237 SRR811631 SRR812246 |
| | SRR814407 SRR816495 SRR816865 |
| | SRR817649 SRR818694 |
| other | SRR1069376 SRR1070111 SRR1070641 |
| | SRR1071644 SRR1072078 SRR1072749 |
| | SRR1073705 SRR1074478 SRR1074622 |
| | SRR1075028 SRR1075579 SRR1076343 |
| | SRR1077090 SRR1078586 SRR1079023 |
| | SRR1079998 SRR1080148 SRR1081137 |
| | SRR1081519 SRR1081910 SRR1082283 |
| | SRR1083076 SRR1083286 SRR1083604 |
| | SRR1084276 SRR1084460 SRR1085159 |
| | SRR654850 SRR808044 SRR808152 |
| | SRR808351 SRR808836 SRR808914 |
| | SRR809320 SRR809470 SRR809785 |
| | SRR809831 SRR810201 SRR810367 |
| | SRR811333 SRR811471 SRR811819 |
| | SRR812673 SRR813632 SRR815092 |
| | SRR816565 SRR817744 SRR818232 |
| | SRR818999 SRR819293 |
| other | SRR1071717 SRR1079830 SRR1081765 |
| | SRR1085402 SRR1086236 SRR1092208 |
| | SRR1093930 SRR1097296 SRR1099957 |
| | SRR1120296 SRR2135324 SRR2135407 |
| MHC low | SRR1081741 SRR1082262 SRR1083632 |
| | SRR1085975 SRR1310008 SRR1310136 |
| | SRR1311400 SRR1311575 SRR1311794 |
| | SRR1312428 SRR1314958 SRR1315269 |
| | SRR1315866 SRR1316815 SRR1320280 |
| | SRR1323043 SRR1323746 SRR1324371 |
| | SRR1327593 SRR1328487 SRR598332 |
| | SRR601006 SRR601669 SRR602927 |
| | SRR603333 SRR604026 SRR608662 |
| | SRR612575 SRR614310 SRR615213 |
| | SRR615838 SRR627421 SRR627425 |
| | SRR627449 SRR627455 SRR654874 |
| | SRR656745 SRR659555 SRR660626 |
| | SRR660933 SRR663320 SRR663753 |
| | SRR664854 SRR808614 SRR810319 |
| | SRR810877 SRR812012 SRR812436 |
| | SRR816770 SRR820078 |
| Female organ | SRR1068977 SRR1068999 SRR1070208 |
| | SRR1070260 SRR1070738 SRR1071084 |
| | SRR1071905 SRR1074860 SRR1075484 |
| | SRR1076219 SRR1076441 SRR1077139 |
| | SRR1077920 SRR1078258 SRR1079948 |
| | SRR1081023 SRR1082859 SRR1083052 |
| | SRR1083959 SRR1084079 SRR1084674 |
| | SRR1086538 SRR1086772 SRR615910 |
| | SRR655447 SRR655852 SRR656911 |
| | SRR656970 SRR657018 SRR657528 |
| | SRR658105 SRR658319 SRR658409 |
| | SRR659223 SRR660248 SRR660283 |
| | SRR662306 SRR662378 SRR662811 |
| | SRR808428 SRR808942 SRR811073 |
| | SRR811285 SRR812198 SRR813868 |
| | SRR815208 SRR816336 SRR818873 |
| | SRR820571 SRR821498 |
| Female organ other | SRR1075223 SRR1088832 SRR1089562 |
| | SRR1096876 SRR1097035 SRR1097574 |
| | SRR1069943 SRR1074337 SRR1077380 |
| | SRR1081068 SRR1083504 SRR1083678 |
| | SRR1084505 SRR1086020 SRR1087271 |
| | SRR1090431 SRR1091524 SRR1092493 |
| | SRR1093366 SRR1102198 SRR1102224 |
| | SRR1102998 SRR1308269 SRR1312577 |
| | SRR1312666 SRR1312784 SRR1317110 |
| | SRR1317653 SRR1318624 SRR1319038 |
| | SRR1320445 SRR1320490 SRR1321377 |
| | SRR1322070 SRR1323002 SRR1323215 |
| | SRR1324473 SRR1327454 SRR1327505 |

TABLE 2-continued

| Tissue group | Accession numbers (SRA) of randomly selected donors |
|---|---|
| | SRR1327527 SRR1327570 SRR1328528 |
| | SRR1328980 SRR1329642 SRR1329663 |
| | SRR1330176 SRR1330770 SRR1330831 |
| | SRR1332467 SRR1333167 SRR1333287 |
| | SRR1334011 SRR1334055 SRR1334181 |
| | SRR1336617 SRR1336863 |
| other | SRR1069231 SRR1069255 SRR1069328 |
| | SRR1069666 SRR1069871 SRR1070036 |
| | SRR1070060 SRR1070620 SRR1070665 |
| | SRR1071207 SRR1071499 SRR1072055 |
| | SRR1072297 SRR1072388 SRR1072480 |
| | SRR1073631 SRR1074450 SRR1074502 |
| | SRR1074578 SRR1075458 SRR1075603 |
| | SRR1076195 SRR1076705 SRR1076801 |
| | SRR1077310 SRR1077356 SRR1077619 |
| | SRR1077850 SRR1078140 SRR1078538 |
| | SRR807679 SRR807703 SRR809406 |
| | SRR809919 SRR812294 SRR812318 |
| | SRR813283 SRR813505 SRR813536 |
| | SRR814467 SRR815116 SRR815568 |
| | SRR816403 SRR817306 SRR819124 |
| | SRR819559 SRR819637 SRR820280 |
| | SRR820689 SRR821282 |
| Female organ | SRR1071359 SRR1074140 SRR1076584 SRR1082520 |
| | SRR1083776 SRR1101693 SRR811938 |
| other | SRR598148 SRR598509 SRR598589 |
| | SRR599025 SRR599086 SRR599249 |
| | SRR599380 SRR600474 SRR600829 |
| | SRR600852 SRR600924 SRR601239 |
| | SRR601613 SRR601645 SRR601868 |
| | SRR601986 SRR602106 SRR602437 |
| | SRR602461 SRR603449 SRR603918 |
| | SRR603968 SRR604122 SRR604174 |
| | SRR604206 SRR604230 SRR606939 |
| | SRR607252 SRR607313 SRR607970 |
| | SRR608096 SRR608480 SRR612335 |
| | SRR612719 SRR612875 SRR613186 |
| | SRR613462 SRR613510 SRR613759 |
| | SRR614215 SRR614683 SRR614996 |
| | SRR615335 SRR615359 SRR615898 |
| | SRR615970 SRR655792 SRR657903 |
| | SRR658283 SRR658331 |
| other | SRR1071807 SRR1080366 SRR1085759 |
| | SRR1089504 SRR1105272 SRR1314940 |
| | SRR1317086 SRR1325483 SRR1328447 |
| | SRR1329154 SRR1340662 SRR1362263 |
| | SRR1377578 SRR1380931 SRR1396700 |
| | SRR1416516 SRR1420649 SRR1432650 |
| | SRR1433066 SRR1435730 SRR1437274 |
| | SRR1442708 SRR1443092 SRR1445835 |
| | SRR1447631 SRR1452888 SRR1456711 |
| | SRR1465871 SRR1468426 SRR1469746 |
| | SRR1486080 SRR1490658 SRR1500261 |
| | SRR2135353 SRR2135396 SRR809943 |
| | SRR810007 SRR821356 |
| other | SRR1069141 SRR1070689 SRR1071668 |
| | SRR1073435 SRR1075102 SRR1075804 |
| | SRR1076022 SRR1080117 SRR1080294 |
| | SRR1081184 SRR1082151 SRR1083983 |
| | SRR1086256 SRR1087007 SRR1087321 |
| | SRR1089446 SRR1090095 SRR1090556 |
| | SRR1091865 SRR1093861 SRR1095383 |
| | SRR1095913 SRR1098737 SRR1100991 |
| | SRR1101883 SRR1102152 SRR1102899 |
| | SRR1105248 SRR1120939 SRR1310433 |
| | SRR1312266 SRR1313807 SRR1316096 |
| | SRR1317532 SRR1317554 SRR1321877 |
| | SRR1322312 SRR1322477 SRR1323491 |
| | SRR1324295 SRR1324412 SRR1325290 |
| | SRR1328760 SRR1331488 SRR1334866 |
| | SRR1335236 SRR1336314 SRR815140 |
| | SRR815711 SRR821043 |
| other | SRR1070015 SRR1070358 SRR1071568 |
| | SRR1072150 SRR1073119 SRR1074769 |
| | SRR1081283 SRR1084602 SRR1084766 |
| | SRR1086728 SRR1087559 SRR1091670 |
| | SRR1095695 SRR1098074 SRR1098785 |

TABLE 2-continued

| Tissue group | Accession numbers (SRA) of randomly selected donors |
|---|---|
| | SRR1098998 SRR1099286 SRR1099546 |
| | SRR1102079 SRR1102804 SRR1307123 |
| | SRR1307615 SRR1308239 SRR1308504 |
| | SRR1308939 SRR1309452 SRR1309468 |
| | SRR1309490 SRR1310313 SRR1310520 |
| | SRR1310797 SRR1310959 SRR1310975 |
| | SRR1312209 SRR1312522 SRR1312558 |
| | SRR813043 SRR814244 SRR814703 |
| | SRR817004 SRR817070 SRR817166 |
| | SRR817488 SRR818499 SRR819186 |
| | SRR819318 SRR819658 SRR820596 |
| | SRR821302 SRR821525 |
| other | SRR1071105 SRR1078392 SRR1080790 |
| | SRR1081589 SRR1097245 SRR1100608 |
| | SRR1315412 SRR1318089 SRR1321897 |
| | SRR1325201 SRR1328715 SRR1330723 |
| | SRR1331771 SRR1338384 SRR1339987 |
| | SRR1340260 SRR1348929 SRR1353600 |
| | SRR1356057 SRR1358391 SRR1376380 |
| | SRR1376450 SRR1376741 SRR1381185 |
| | SRR1382978 SRR1385690 SRR1386927 |
| | SRR1388459 SRR1389955 SRR1397720 |
| | SRR1400931 SRR1404339 SRR1405147 |
| | SRR1406135 SRR1406348 SRR1407044 |
| | SRR1413307 SRR1416141 SRR1416188 |
| | SRR1416841 SRR1418225 SRR1418473 |
| | SRR1418747 SRR1419561 SRR1429429 |
| | SRR1429540 SRR1431823 SRR1432868 |
| | SRR1432958 SRR1433493 |
| other | SRR1068855 SRR1071231 SRR1071594 |
| | SRR1071955 SRR1074359 SRR1074670 |
| | SRR1074719 SRR1077288 SRR1077805 |
| | SRR1080766 SRR1084369 SRR1084417 |
| | SRR1085519 SRR1087245 SRR1087825 |
| | SRR1088581 SRR1089424 SRR1089901 |
| | SRR1090265 SRR1092349 SRR1092985 |
| | SRR1094051 SRR1095720 SRR1096174 |
| | SRR1096662 SRR1098474 SRR1098879 |
| | SRR1100588 SRR1102830 SRR1105057 |
| | SRR812773 SRR813656 SRR813802 |
| | SRR813983 SRR815020 SRR815044 |
| | SRR815470 SRR815783 SRR815825 |
| | SRR816015 SRR816226 SRR816382 |
| | SRR817282 SRR817421 SRR818600 |
| | SRR818773 SRR818901 SRR819054 |
| | SRR819261 SRR820907 |
| MHC low | SRR1070086 SRR1070159 SRR1070597 |
| | SRR1072724 SRR1073553 SRR1074550 |
| | SRR1075384 SRR1075825 SRR1076559 |
| | SRR1079636 SRR1079850 SRR1080093 |
| | SRR1082059 SRR1082809 SRR1086417 |
| | SRR1087079 SRR1088706 SRR1090070 |
| | SRR1091184 SRR1092062 SRR1095334 |
| | SRR1096007 SRR1096222 SRR1096478 |
| | SRR1096500 SRR1096806 SRR1097055 |
| | SRR1098385 SRR1310455 SRR1310645 |
| | SRR1311131 SRR1311308 SRR1312370 |
| | SRR1312464 SRR813704 SRR814052 |
| | SRR814996 SRR815422 SRR815685 |
| | SRR817026 SRR817397 SRR817539 |
| | SRR817609 SRR818939 SRR818961 |
| | SRR820350 SRR820402 SRR821096 |
| | SRR821124 SRR821255 |
| Female organ | SRR1071475 SRR1073389 SRR1073878 |
| | SRR1075360 SRR1078042 SRR1078636 |
| | SRR1078735 SRR1081987 SRR1082352 |
| | SRR1082471 SRR1085565 SRR1085736 |
| | SRR1086212 SRR1086656 SRR1088856 |
| | SRR1089134 SRR1090698 SRR1090928 |
| | SRR1091164 SRR1092038 SRR1093601 |
| | SRR1093747 SRR1096458 SRR1097124 |
| | SRR1097148 SRR1098807 SRR1099310 |
| | SRR1099669 SRR1101453 SRR1101859 |
| | SRR1102005 SRR1102780 SRR1120276 |
| | SRR1312446 SRR1315495 SRR1316513 |
| | SRR1319793 SRR1336244 SRR1339699 |
| | SRR1340598 SRR1341583 SRR1342849 |

TABLE 2-continued

| Tissue group | Accession numbers (SRA) of randomly selected donors |
|---|---|
| | SRR1347518 SRR1350891 SRR1351641 |
| | SRR1353537 SRR814293 SRR814892 |
| | SRR816629 SRR821072 |
| other | SRR1069352 SRR1070403 SRR1070764 |
| | SRR1071519 SRR1072007 SRR1072104 |
| | SRR1072972 SRR1073021 SRR1073167 |
| | SRR1073991 SRR1074090 SRR1074385 |
| | SRR1075174 SRR1075336 SRR1076244 |
| | SRR1076868 SRR1078066 SRR1079754 |
| | SRR1080624 SRR1082080 SRR1082544 |
| | SRR1084128 SRR1084323 SRR1085187 |
| | SRR1085310 SRR1086070 SRR1087728 |
| | SRR1088291 SRR1088413 SRR1088537 |
| | SRR1089537 SRR1089688 SRR1091032 |
| | SRR1091144 SRR1092937 SRR1093340 |
| | SRR1093434 SRR1093577 SRR1095407 |
| | SRR1095479 SRR1095651 SRR1097777 |
| | SRR1097883 SRR812745 SRR813208 |
| | SRR816541 SRR819771 SRR821050 |
| | SRR821231 SRR821666 |
| other | SRR1076393 SRR1077455 SRR1077708 |
| | SRR1077968 SRR1082664 SRR1082685 |
| | SRR1089785 SRR1096101 SRR1096339 |
| | SRR1101612 SRR1309119 SRR1309638 |
| | SRR1310817 SRR1311599 SRR1311709 |
| | SRR1311958 SRR1317963 SRR1318026 |
| | SRR1319946 SRR1321650 SRR1323977 |
| | SRR1324141 SRR1324184 SRR1325161 |
| | SRR1325944 SRR1326408 SRR1326797 |
| | SRR1328143 SRR1331962 SRR1332024 |
| | SRR1332904 SRR1336029 SRR1336529 |
| | SRR1337321 SRR1339007 SRR1340241 |
| | SRR1343012 SRR1343221 SRR1343720 |
| | SRR1343778 SRR1345329 SRR1347236 |
| | SRR1347278 SRR1347389 SRR813959 |
| | SRR815920 SRR816517 SRR816609 |
| | SRR816677 SRR821573 |
| other | SRR1069048 SRR1070232 SRR1070888 |
| | SRR1073605 SRR1074289 SRR1075247 |
| | SRR1076292 SRR1077263 SRR1077898 |
| | SRR1079434 SRR1083215 SRR1083579 |
| | SRR1084299 SRR1087801 SRR1091597 |
| | SRR1094216 SRR1095503 SRR1096408 |
| | SRR1098216 SRR1100703 SRR1309920 |
| | SRR1309985 SRR1310053 SRR1311153 |
| | SRR1311224 SRR1311916 SRR1312124 |
| | SRR1312244 SRR1312645 SRR1312934 |
| | SRR1313494 SRR1314036 SRR1314137 |
| | SRR1314728 SRR1314810 SRR1315912 |
| | SRR1316438 SRR1316747 SRR1316833 |
| | SRR1317022 SRR814491 SRR815164 |
| | SRR815350 SRR815759 SRR815805 |
| | SRR818372 SRR818440 SRR819844 |
| | SRR820427 SRR820810 |
| other | SRR1070133 SRR1071181 SRR1072602 |
| | SRR1074934 SRR1076046 SRR1076465 |
| | SRR1077728 SRR1079973 SRR1084154 |
| | SRR1085378 SRR1087680 SRR1310497 |
| | SRR1311731 SRR1313664 SRR1319059 |
| | SRR1319301 SRR1321483 SRR1326449 |
| | SRR1326845 SRR1329508 SRR1330371 |
| | SRR1337749 SRR1337930 SRR1338402 |
| | SRR1339086 SRR1340762 SRR1340782 |
| | SRR1343136 SRR1344079 SRR1344364 |
| | SRR1351907 SRR1354400 SRR1356327 |
| | SRR1358803 SRR1359027 SRR1359587 |
| | SRR1360321 SRR1361391 SRR1365655 |
| | SRR1365767 SRR1366102 SRR1366412 |
| | SRR1367520 SRR1375371 SRR1378199 |
| | SRR1379036 SRR1380358 SRR1380436 |
| | SRR1384312 SRR1387745 |
| other | SRR1068953 SRR1069166 SRR1069714 |
| | SRR1069778 SRR1070382 SRR1070549 |
| | SRR1070884 SRR1071761 SRR1072199 |
| | SRR1072700 SRR1072821 SRR1072920 |
| | SRR1073459 SRR1074066 SRR1075874 |
| | SRR1076268 SRR1076417 SRR1076990 |

TABLE 2-continued

| Tissue group | Accession numbers (SRA) of randomly selected donors |
|---|---|
| | SRR1078090 SRR1078759 SRR1079900 |
| | SRR1080672 SRR1081092 SRR1081235 |
| | SRR1081717 SRR1081935 SRR1082933 |
| | SRR1082957 SRR1083149 SRR1083191 |
| | SRR1083262 SRR1083360 SRR1083408 |
| | SRR1084252 SRR1085450 SRR1087101 |
| | SRR1088068 SRR1088117 SRR808542 |
| | SRR810689 SRR810829 SRR811193 |
| | SRR812152 SRR813234 SRR814195 |
| | SRR814268 SRR814820 SRR815326 |
| | SRR815970 SRR819719 |
| MHC low | SRR1068788 SRR1068905 SRR1069734 |
| | SRR1070479 SRR1071379 SRR1071429 |
| | SRR1072845 SRR1073531 SRR1075607 |
| | SRR1076490 SRR1077753 SRR1078299 |
| | SRR1078612 SRR1079455 SRR1079612 |
| | SRR1080022 SRR1080811 SRR1080859 |
| | SRR1081357 SRR1081401 SRR1081449 |
| | SRR1081614 SRR1081663 SRR1081688 |
| | SRR1082307 SRR1083554 SRR1084347 |
| | SRR1087055 SRR1087535 SRR1088241 |
| | SRR1308288 SRR1309425 SRR1311329 |
| | SRR1312288 SRR1314014 SRR807517 |
| | SRR808065 SRR809667 SRR810531 |
| | SRR810899 SRR811447 SRR812912 |
| | SRR813431 SRR814082 SRR814943 |
| | SRR815588 SRR817512 SRR818850 |
| | SRR820839 SRR821518 |
| other | SRR597952 SRR598068 SRR598100 |
| | SRR598364 SRR598565 SRR598645 |
| | SRR599122 SRR599346 SRR599412 |
| | SRR601157 SRR601359 SRR601525 |
| | SRR601549 SRR601843 SRR601962 |
| | SRR602338 SRR602389 SRR602951 |
| | SRR602978 SRR603036 SRR603268 |
| | SRR603726 SRR603834 SRR603942 |
| | SRR604148 SRR604294 SRR604342 |
| | SRR607502 SRR607679 SRR607705 |
| | SRR608064 SRR608120 SRR608512 |
| | SRR613018 SRR613258 SRR613402 |
| | SRR613711 SRR613795 SRR613975 |
| | SRR614023 SRR614107 SRR614275 |
| | SRR614743 SRR614912 SRR615285 |
| | SRR615347 SRR615491 SRR615886 |
| | SRR654969 SRR655696 |
| Female organ | SRR1069466 SRR1071737 SRR1073483 |
| | SRR1074430 SRR1075850 SRR1077159 |
| | SRR1077211 SRR1077996 SRR1078114 |
| | SRR1078188 SRR1078212 SRR1079213 |
| | SRR1079408 SRR1079874 SRR1080342 |
| | SRR1082128 SRR1084553 SRR1085358 |
| | SRR1086369 SRR1309745 SRR1313991 |
| | SRR1319242 SRR1319991 SRR1321720 |
| | SRR1323234 SRR1329423 SRR1330082 |
| | SRR1336682 SRR1338468 SRR1339258 |
| | SRR1343943 SRR1353686 SRR1358126 |
| | SRR1360280 SRR1361138 SRR1361838 |
| | SRR1363718 SRR1374543 SRR1381372 |
| | SRR1382780 SRR1383237 SRR1387132 |
| | SRR1388257 SRR808704 SRR810105 |
| | SRR815256 SRR817817 SRR818139 |
| | SRR818646 SRR820026 |
| Female organ | SRR1070286 SRR1070789 SRR1071832 |
| | SRR1072129 SRR1073045 SRR1073095 |
| | SRR1075150 SRR1076892 SRR1079143 |
| | SRR1079356 SRR1079686 SRR1079706 |
| | SRR1080534 SRR1080580 SRR1082423 |
| | SRR1083171 SRR1083337 SRR1084228 |
| | SRR1087463 SRR1089106 SRR1089761 |
| | SRR1093124 SRR1093410 SRR1093814 |
| | SRR1095599 SRR1097728 SRR1101061 |
| | SRR1101907 SRR1313747 SRR1318390 |

TABLE 2-continued

| Tissue group | Accession numbers (SRA) of randomly selected donors |
| --- | --- |
| | SRR1320650 SRR1322115 SRR1323957 |
| | SRR1328464 SRR1330018 SRR1330450 |
| | SRR1330474 SRR1332775 SRR1334791 |
| | SRR1335089 SRR1337840 SRR1340028 |
| | SRR1340989 SRR1344185 SRR1351605 |
| | SRR1354159 SRR1358238 SRR814137 |
| | SRR815944 SRR820859 |

Expression of TSA-coding regions. The RNA expression of TSA coding region was quantified from mapped bam files using the 'qCount' function of R package 'QuasR' (30) with parameter orientation="same", as counts of all reads that overlapped with TSA coding region on the TSA coding strand. The counts were normalized to reads per hundred million reads mapped. In aeTSA expression analyses, we specifically analyzed the unique region to which individual aeTSAs were mapped because the context of the surrounding sequence may influence aeTSA expression.

Clinical and genomic data from TCGA. Processed and normalized level 3 data with hg38 for HM27 methylation, DNA copy number variation, RNA-Seq gene expression as well as the clinical data were downloaded from the TCGA open-access database using the R package 'TCGAbiolinks' (31). Arm-level DNA copy number alterations were downloaded from Broad Institute TCGA Genome Data Analysis Center (doi:10.7908/C1P84B9Q).

Immune cell scores. Immune cell scores representing immune cell populations were estimated based on RNA-Seq data. For each tumor, scores were estimated as the average of log-transformed FPKM values of their marker genes as described by Danaher et al. (32).

Frequency of aeTSA presentation. A bioinformatic simulation was performed to estimate the number of aeTSAs presented by individual patients. This estimation was based on two parameters. First, the likelihood of aeTSA expression was based on the proportion of tumors expressing the corresponding RNA in the TCGA-OV cohort. For aeTSA containing a germline SNP, the expression likelihood was calculated as follows: (proportion of TCGA tumors expressing aeTSA)×(SNP frequency in the given population). The SNP frequencies were obtained from the Genome Aggregation Database. Second, the HLA allele frequencies were retrieved from USA National Marrow Donor Program (NMDP) for the European-American population (n=1242890), African American (n=416581) and Chinese (n=99672). Next, patient's HLA genotype was simulated with six HLA class I alleles based on the reported frequencies in the given population. Since it was assumed that the six HLA alleles were independent events, some HLA loci were homozygous in simulated patients. An aeTSA was considered to be presented in a simulated patient when both the aeTSA and the relevant HLA allele were expressed. Expression of each aeTSA was considered to be an independent event, except for the overlapping aeTSAs whose expression status was only simulated once for the same overlapping group. One million simulated patients and their aeTSA presentation status were generated for each the three populations and used for plotting the distribution.

Statistical analyses and data visualization. Analyses and figures were performed using the R v3.5.1 or Python v2.7.6. The 'gplots' package in R was used to generate heatmaps of TSA coding region expression in tumors. Correlation tests were done using R function 'cor.test' with the Spearman's method unless otherwise indicated. Tests involving comparisons of distributions were performed with ANOVA test, and pairwise comparisons between groups were performed by Wilcoxon rank sum test. Log-rank P values for survival analysis were calculated with the 'survival' package.

Example 2: Proteogenomic Analyses Identify 111 TSAs in 23 HGSCs

Figure 1:
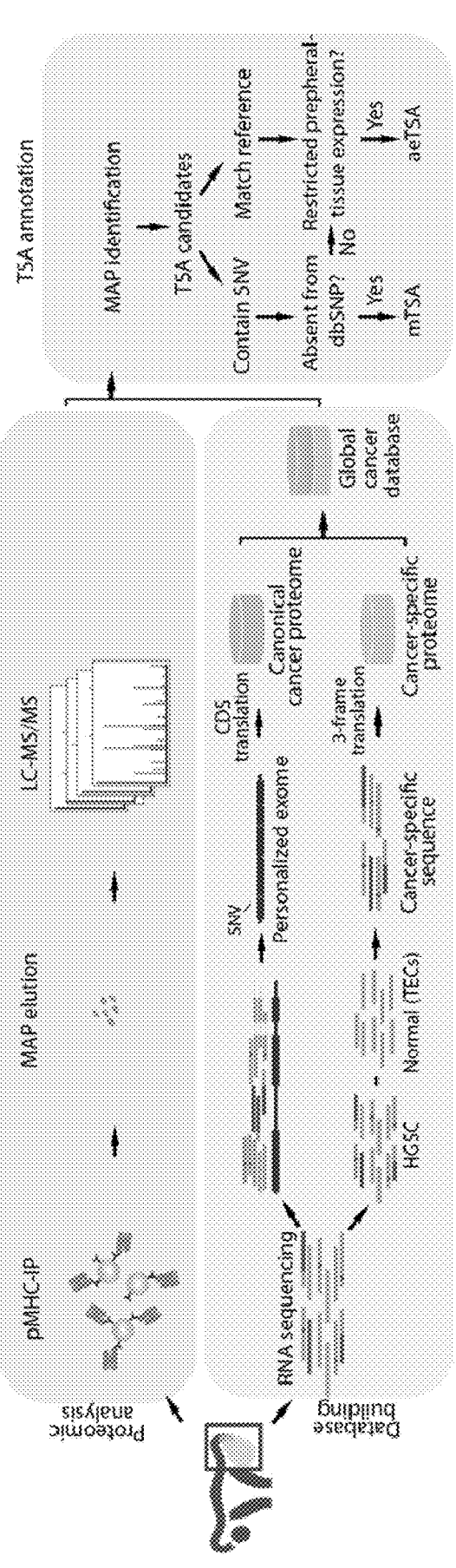
FIG. 1 show a schematic workflow of TSA identification pipeline used in this study. HGSC samples were processed for immunoprecipitation and RNA sequencing. Peptide sequences were identified using MS analyses that identified MAPs by searching for matches in customized individual global cancer databases built from RNA-Seq data. CDS: coding sequence.

To get a systems-level characterization of the TSA landscape, direct MAP identification with high-throughput tandem MS (MS/MS) analyses (34-36) was performed. Current search engines rely on user-defined protein databases to match each acquired MS/MS spectrum to a peptide sequence (37). Hence, a peptide in a test sample can only be identified by the search engine when its sequence is included in the reference database. Since generic reference protein databases such as UniProt do not contain sample-specific mutations, out-of-frame translation events and non-exonic sequences, the quest to capture TSAs coded by all genomic regions required construction of customized databases containing tumor-specific translation products for each tumor. Therefore, the recently described proteogenomic approach (15) was used to build a customized search database from RNA-Seq reads of each sample analyzed. Such customized databases contain two modules: the canonical proteome (in-frame translation of exons) and the cancer-specific proteome, which is a 3-frame translation of cancer-specific RNA sequences after subtraction of normal RNA sequences (from TECs) (FIG. 1). TECs were used as a normal control for two reasons: i) their key role in establishing immune tolerance during the development of immature T cells (i.e., central tolerance), and ii) their remarkable ability to promiscuously express more transcripts than other types of somatic cells (38). MAPs from nine primary HGSC samples were obtained by immunoprecipitation of MHC I molecules, then analyzed by liquid chromatography-MS/MS (15,28). Immunopeptidomic data of an additional cohort of 14 HGSCs reported by Schuster et al. (13) was also re-analyzed by applying the proteogenomic approach described herein to the samples for which matched RNA-Seq and MS data were available. Each of the TSA candidates was confirmed by manual validation of spectra and genomic location.

Figure 8A:
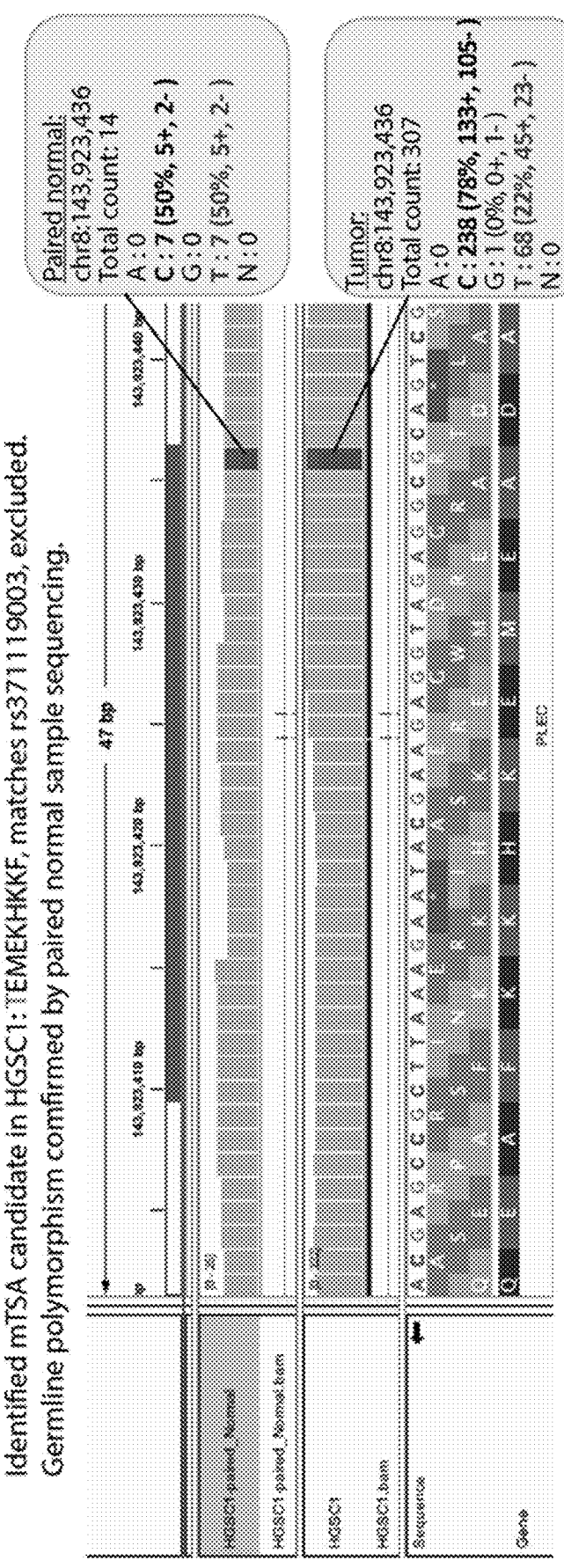
FIGS. 8A-B show that the mTSA validation based on dbSNP is also supported by sequencing data of paired normal samples.
Figure 8B:
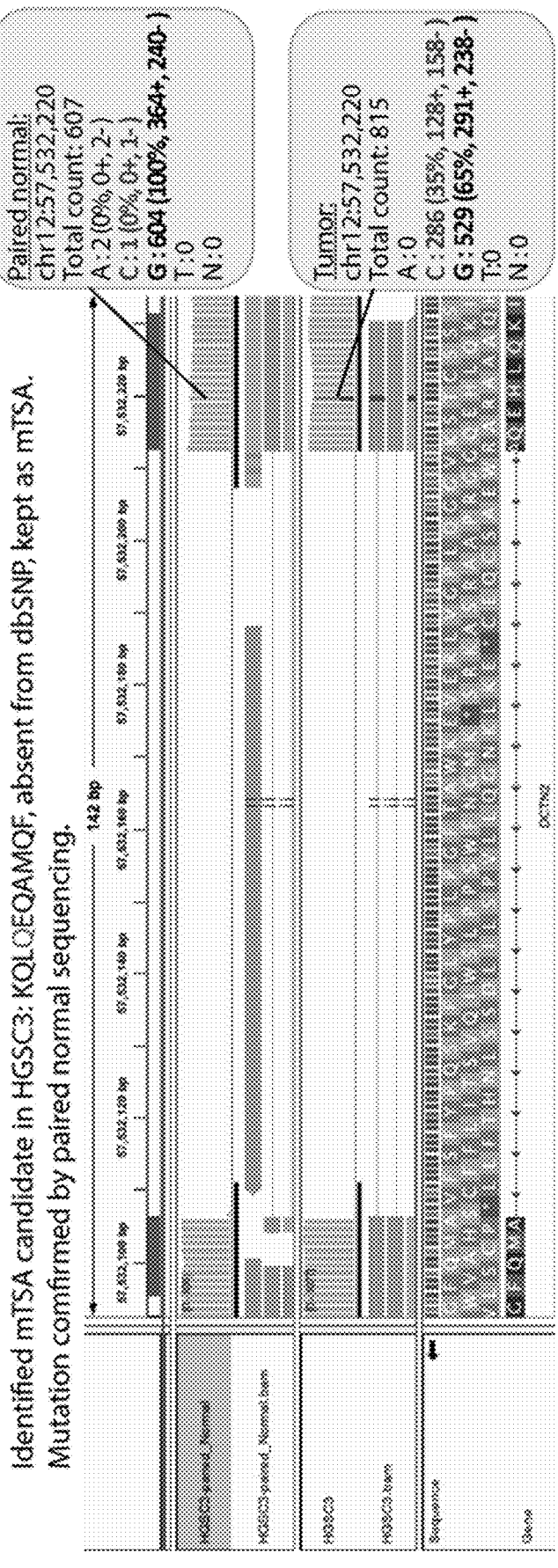

Candidates overlapping genomic variants absent in dbSNP were unlikely to represent germline polymorphisms and were therefore labeled as mTSAs. Such classification yielded 18 mTSAs from the 23 samples analyzed (Table 3A). None of these mTSAs has been previously reported. Of the 18 mTSAs, seven resulted from in-frame exonic translation, four from out-of-frame exonic translation and eight from noncoding sequences. For three tumors, matched normal tissue was available and RNA-Seq analyses confirmed that mTSA variants were not germline polymorphisms (FIGS. 8A-8B). For tumors without matched normal tissues, it cannot be formally excluded that some mTSAs might correspond to rare polymorphisms absent in dbSNP. The possibility that the number of mTSAs may be slightly overestimated would only reinforce the conclusion that, with less than one mTSA per tumor (18 mTSAs/23 tumors), mTSAs are rare in HGSCs and thus represent less attractive targets. Moreover, since classic TSA discovery methods focus strictly on mTSAs resulting from in-frame exonic translation, they would have uncovered only seven of the 111 TSAs reported herein.

TABLE 3A

| | | | | | |
|---|---|---|---|---|---|
| Characteristics of mTSAs identified in the present study | | | | | |
| TSA se-quence | Translation events | Genomic origin | Gene name | MHC class I allele | SEQ ID NO: |
| LASTP WEK | Noncoding | 3'UTR | YWHAB | HLA-A* 03:01 | 1 |
| ILNPE ELEKY | Coding-in | Annotated ORF | PSMA7 | HLA-B* 15:01 | 2 |
| LLNPE EIEKY | Coding-in | Annotated ORF | PSMA7 | HLA-B* 15:01 | 3 |
| RPRPP PPPP | Noncoding | ncRNA | FP671 120.1 | HLA-B* 07:02 | 4 |
| KQLQE QAMQF | Coding-in | Annotated ORF | DCTN2 | HLA-B* 15:01 | 5 |
| RPRTA GPPR | Coding-out | Frameshift | MUC1 | HLA-B* 07:02; HLA-C* 04:01 | 6 |
| RAPPP PKPM | Coding-out | Frameshift | MUC1 | HLA-C* 07:02 | 7 |
| RPASS RPL | Noncoding | 5'UTR | RALY | HLA-B* 07:02 | 8 |
| RPGVK LIL | Coding-in | Annotated ORF | VDAC3 | HLA-B* 07:02 | 9 |
| WGTPP SPPP | Noncoding | 3'UTR | GRK3 | HLA-C* 03:03 | 10 |
| AELRG TASL | Coding-in | Annotated ORF | PALM2-AKAP2/ AKAP2 | HLA-B* 40:01 | 11 |
| SEAKL TGL | Coding-in | Annotated ORF | BGN | HLA-B* 40:01 | 12 |
| SEIPT KKL | Noncoding | 3'UTR | COL3A1 | HLA-B* 40:01 | 13 |
| VLDNK DYFL | Coding-in | Annotated ORF | HSPE1 | HLA-A* 02:01 | 14 |
| RPFSP PPSF | Noncoding | 3'UTR | MRC2 | HLA-C* 04:01 | 15 |
| RNLPL VLIF | Noncoding | Intron | RASA3 | HLA-A* 32:01 | 16 |

TABLE 3A-continued

| | | | | | |
|---|---|---|---|---|---|
| Characteristics of mTSAs identified in the present study | | | | | |
| TSA se-quence | Translation events | Genomic origin | Gene name | MHC class I allele | SEQ ID NO: |
| TLLPR LVFI | Noncoding | Intron | STON2 | HLA-A* 02:01 | 17 |
| RAVIW RLV | Coding-out | Frameshift | COL1A1 | HLA-C* 06:02 | 18 |

Figure 2A:
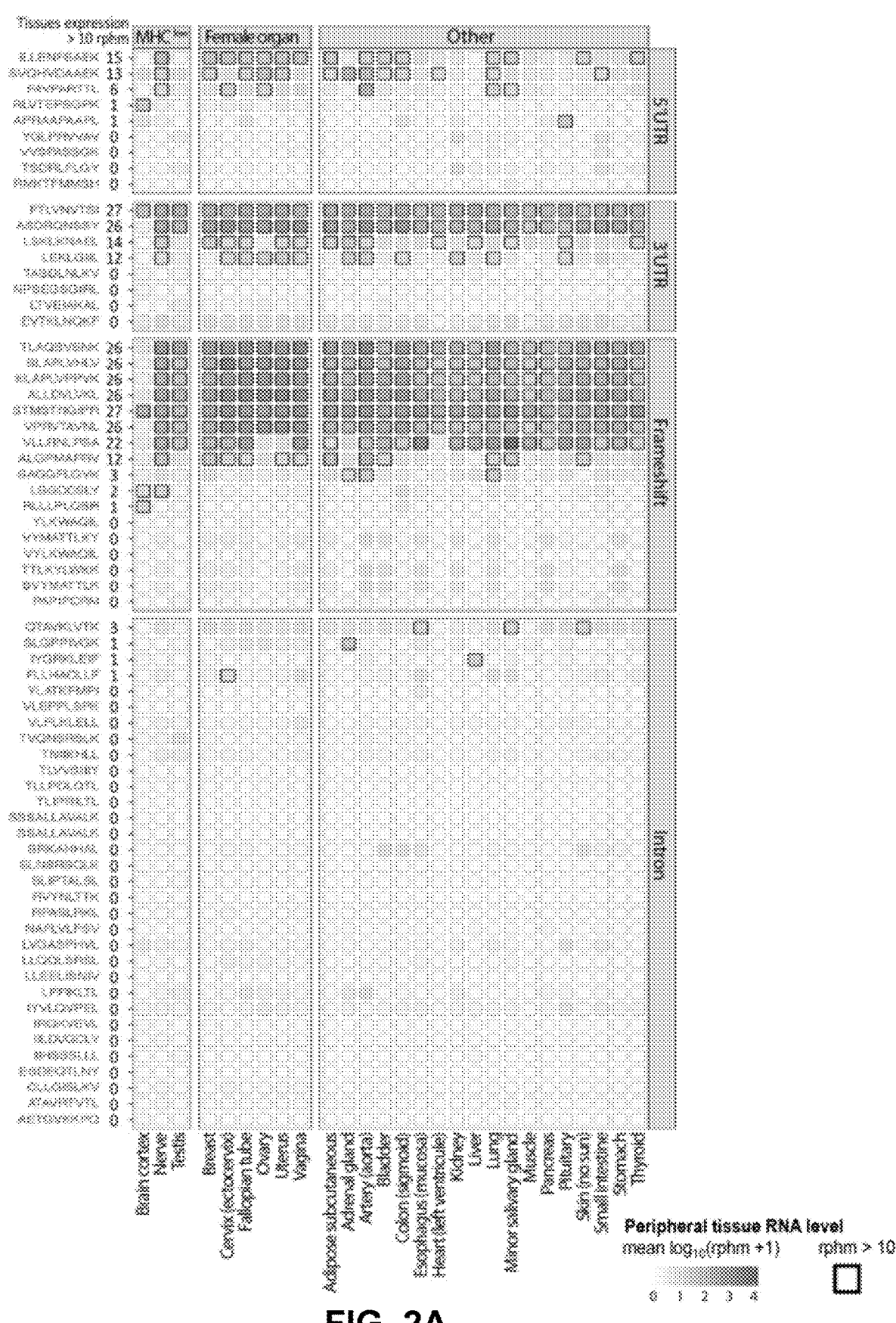
FIGS. 2A-B depict the expression in normal tissues of RNAs coding for aeTSA candidates. Heatmap showing the average RNA expression of aeTSA coding sequences in 27 peripheral tissues, with color intensity corresponding to the expression level of each tissue in mean log-transformed reads per hundred million reads sequenced (rphm). Bold boxes indicate tissues/organs with above threshold RNA expression (mean rphm>10). Numbers beside each peptide sequence show the number of tissues with above threshold expression of the corresponding RNA.
Figure 2B:
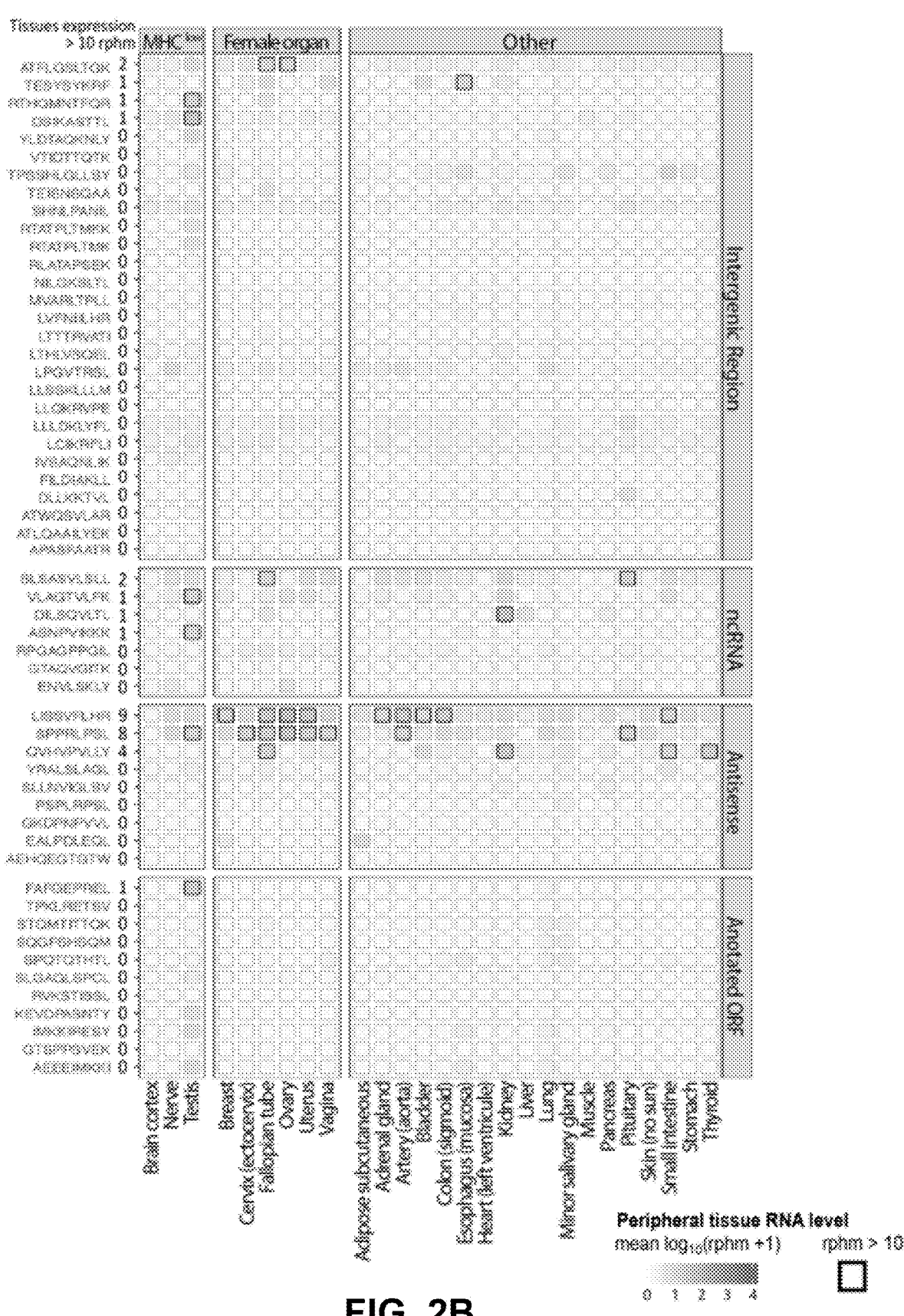
Figure 9:
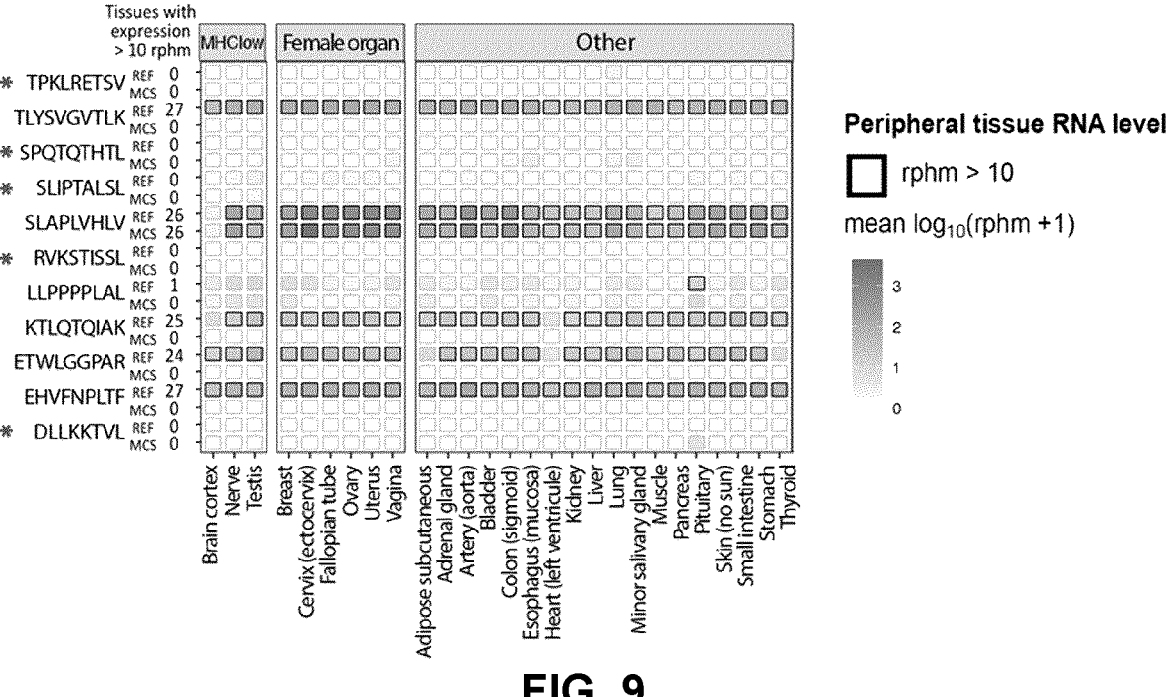
FIG. 9 shows the peripheral expression of coding sequences for TSA candidates containing germline polymorphisms. TSA candidates with single nucleotide variations recorded in dbSNP were considered as aeTSAs when both their coding sequences and corresponding reference sequences have restricted RNA expression in peripheral tissues. Heatmap showing the average RNA expression of aeTSA coding sequences in 27 peripheral tissues, with color intensity corresponds to the expression level of each tissue in mean log-transformed reads per hundred million reads sequenced (rphm). Bold boxes indicate tissues/organs with a mean rphm value higher than 10. The number beside each peptide sequence shows the number of tissues has considerable RNA expression for the given peptides. Red asterisks indicate the peptides kept as aeTSAs.

For the unmutated TSA candidates, stringent criteria were applied to identify those that were genuine aeTSAs, that is, whose expression was cancer-specific. To this end, their RNA expression in 27 peripheral tissues across the human body was analyzed. All candidates whose coding RNA were expressed (rphm>10) in any peripheral tissue other than MHC$^{low}$ tissues (brain, nerve, testis) were excluded from the aeTSA list. When the coding sequence of an aeTSA candidate contained a germline single polymorphism (reported in dbSNP), this candidate was labeled as a valid aeTSA only when the SNP-containing sequence and the reference sequence fulfilled the above criteria (FIG. 9). Overall, 93 aeTSA candidates satisfied these stringent criteria (FIG. 2, Tables 3B and 3C), among which 85 have never been reported to our knowledge (Table 2B). Interestingly, five out of 93 aeTSAs were expressed in the testis, showing that some cancer-germline antigens (CGAs) are aeTSAs but that most aeTSAs are not CGAs. CGAs are coded by canonical exons normally expressed only by germ cells, and their aberrant expression in cancer cells is mainly driven by epigenetic alterations. However, some MGAs are expressed by adult mTECs (16), and CGAs expressed in mTECs (or other somatic tissues) are considered as TAAs and those not expressed by any normal tissue (including mTECs) as genuine aeTSAs.

Each aeTSA was assigned a genomic location. When multiple locations were possible, the one with the highest occurrence of matching RNA reads was selected. Features of all TSAs are reported in Tables 3B and 3C. It is formally possible that the stringent approach may underestimate the total number of aeTSAs resulting from atypical translation (5'UTR, 3'UTR, intergenic, frameshift). Indeed, while the reading frame used to generate MAPs in tumors is known, when their coding RNA is expressed in some normal tissue, it cannot infer which reading frame might be translated. Such aeTSAs candidates were therefore excluded in order to avoid inclusion of false positives in the TSA list.

TABLE 3B

| | | | | | |
|---|---|---|---|---|---|
| Characteristics of novel aeTSAs identified in the present study | | | | | |
| TSA sequence | Translation events[1] | Genomic origin[2] | Gene name | MHC class I allele | SEQ ID NO: |
| RLVTEPSGPK | Noncoding | 5'UTR | LINGO1 | HLA-A*03:01 | 19 |
| RMKTFMMSH | Noncoding | 5'UTR | NDRG2 | HLA-A*03:01 | 20 |
| TSDRLFLGY | Noncoding | 5'UTR | TMEM139 | HLA-A*01:01 | 21 |
| WSPASSGK | Noncoding | 5'UTR | ZNF831 | HLA-A*03:01 | 22 |
| YGLPRWAV | Noncoding | 5'UTR | TMEM139 | HLA-B*08:01 | 23 |
| EVTKLNQKF | Noncoding | 3'UTR | MARCH1 | HLA-A*25:01 | 24 |

TABLE 3B-continued

| TSA sequence | Translation events[1] | Genomic origin[2] | Gene name | MHC class I allele | SEQ ID NO: |
|---|---|---|---|---|---|
| LTVEIAKAL | Noncoding | 3'UTR | ZNF257 | HLA-C*14:02 | 25 |
| NPSEGSGIRL | Noncoding | 3'UTR | KIF26B | HLA-B*07:02 | 26 |
| TASDLNLKV | Noncoding | 3'UTR | CLYBL | HLA-C*05:01 | 27 |
| LSGCCSLY | Coding-out | Frameshift | OPCML | HLA-A*01:01 | 28 |
| PAPIPCPAI | Coding-out | Frameshift | TIAM2 | HLA-C*03:03 | 29 |
| RLLLPLQSR | Coding-out | Frameshift | KIRREL3 | HLA-A*03:01 | 30 |
| SVYMATTLK | Coding-out | Frameshift | MECOM | HLA-A*03:01 | 31 |
| TTLKYLWKK | Coding-out | Frameshift | MECOM | HLA-A*11:01 | 32 |
| VYLKWAQIL | Coding-out | Frameshift | IMPG2 | HLA-A*24:02 | 33 |
| VYMATTLKY | Coding-out | Frameshift | MECOM | HLA-A*29:02 | 34 |
| YLKWAQIL | Coding-out | Frameshift | IMPG2 | HLA-B*08:01 | 35 |
| ATWQSVLAR | Noncoding | intronic | AC093627.1 | HLA-A*03:01 | 36 |
| AETGVKKPQ | Noncoding | Intronic | LINC01234 | HLA-B*44:03 | 37 |
| ATAVRTVTL | Noncoding | Intronic | LDAH | HLA-C*07:01 | 38 |
| CLLGISLKV | Noncoding | Intronic | ABI3BP | HLA-A*02:01 | 39 |
| ESDEQTLNY | Noncoding | Intronic | SHISA9 | HLA-A*01:01 | 40 |
| IILDVGCLY | Noncoding | Intronic | UHRF1BP1L | HLA-A*01:01 | 41 |
| IRQKVEVL | Noncoding | Intronic | PTPRK | HLA-B*08:01 | 42 |
| IYVLQVPEL | Noncoding | Intronic | TMEM126A | HLA-A*24:02 | 43 |
| LFFIKLTL | Noncoding | Intronic | AC112229.4 | HLA-B*08:01 | 44 |
| LLEELISNIV | Noncoding | Intronic | FAM172A | HLA-A*02:01 | 45 |
| LLQQLSRSL | Noncoding | Intronic | RIN2 | HLA-B*08:01 | 46 |
| LVGASPHVL | Noncoding | Intronic | HAGHL | HLA-B*39:01 | 47 |
| NAFLVLFSV | Noncoding | Intronic | KLHL12 | HLA-A*02:01 | 48 |
| RPASLRKL | Noncoding | Intronic | LRRFIP2 | HLA-B*07:02 | 49 |
| RVYNLTTK | Noncoding | Intronic | AC079298.3 | HLA-A*03:01 | 50 |
| SLIPTALSL | Noncoding | Intronic | CCDC92 | HLA-A*02:01 | 51 |
| SLNSRSQLK | Noncoding | Intronic | TCF4 | HLA-A*03:01 | 52 |
| SRKAHHAL | Noncoding | Intronic | PTGS1 | HLA-B*14:01 | 53 |
| SSALLAVALK | Noncoding | Intronic | SPON1 | HLA-A*11:01 | 54 |
| SSSALLAVALK | Noncoding | Intronic | SPON1 | HLA-A*11:01 | 55 |
| TLIPRILTL | Noncoding | Intronic | ATRN | HLA-A*02:01 | 56 |
| TLLPDLQTL | Noncoding | Intronic | RORA | HLA-C*14:02 | 57 |
| TLWSIIIY | Noncoding | Intronic | ADAM32 | HLA-A*29:02 | 58 |
| TNIIKHLL | Noncoding | Intronic | SLC44A2 | HLA-B*08:01 | 59 |
| TVQNSRSLK | Noncoding | Intronic | SYCE1L | HLA-A*03:01 | 60 |
| VLFLKLELL | Noncoding | Intronic | AL645568.1 | HLA-C*07:01 | 61 |
| VLSPPLSPK | Noncoding | Intronic | PRSS50 | HLA-A*03:01 | 62 |

TABLE 3B-continued

Characteristics of novel aeTSAs identified in the present study

| TSA sequence | Translation events[1] | Genomic origin[2] | Gene name | MHC class I allele | SEQ ID NO: |
|---|---|---|---|---|---|
| YLATKFMPI | Noncoding | Intronic | ADGRL2 | HLA-B*08:01 | 63 |
| SHNLPANIL | Noncoding | intronic | THAP4 | HLA-B*39:01 | 64 |
| TEISNSQAA | Noncoding | Intergenic | NA | HLA-B*44:02 | 65 |
| TPSSHLGLLSY | Noncoding | Intergenic | NA | HLA-A*01:01 | 66 |
| VTIDTTQTK | Noncoding | Intergenic | NA | HLA-A*11:01 | 67 |
| APASFAATR | Noncoding | Intergenic | NA | HLA-A*68:01 | 68 |
| ATLQAAILYEK | Noncoding | Intergenic | NA | HLA-A*11:01 | 69 |
| DLLKKTVL | Noncoding | Intergenic | NA | HLA-B*08:01 | 70 |
| DSIKASTTL | Noncoding | Intergenic | NA | HLA-C*03:03 | 71 |
| FILDIAKLL | Noncoding | Intergenic | NA | HLA-C*06:02 | 72 |
| IVSAQNLIK | Noncoding | Intergenic | NA | HLA-A*03:01 | 73 |
| LCIKRFLI | Noncoding | Intergenic | NA | HLA-B*08:01 | 74 |
| LLLDKLYFL | Noncoding | Intergenic | NA | HLA-A*02:01 | 75 |
| LLQKRVPE | Noncoding | Intergenic | NA | HLA-B*08:01 | 76 |
| LLSSKLLLM | Noncoding | Intergenic | NA | HLA-A*02:01 | 77 |
| LPGVTRSL | Noncoding | Intergenic | NA | HLA-B*07:02 | 78 |
| LTHLVSQEL | Noncoding | Intergenic | NA | HLA-C*14:02 | 79 |
| LTTTRVATI | Noncoding | Intergenic | NA | HLA-C*12:03 | 80 |
| LVFNIILHR | Noncoding | Intergenic | NA | HLA-A*11:01 | 81 |
| MVARLTPLL | Noncoding | Intergenic | NA | HLA-A*02:01 | 82 |
| NILGKSLTL | Noncoding | Intergenic | NA | HLA-B*08:01 | 83 |
| RLATAPSEK | Noncoding | Intergenic | NA | HLA-A*03:01 | 84 |
| RTATPLTMK | Noncoding | ncRNA[3] | MKRN4P | HLA-A*03:01 | 85 |
| RTATPLTMKK | Noncoding | ncRNA | MKRN4P | HLA-A*03:01 | 86 |
| RTHQMNTFQR | Noncoding | ncRNA | SLC25A3P1 | HLA-A*11:01 | 87 |
| YLDTAQKNLY | Noncoding | ncRNA | ZNF725P | HLA-A*01:01 | 88 |
| ENVLSKLY | Noncoding | ncRNA | LINC01197 | HLA-B*18:01 | 89 |
| GTAQVGITK | Noncoding | ncRNA | AC005062.1 | HLA-A*11:01 | 90 |
| VLAGTVLFK | Noncoding | ncRNA | HAGLROS | HLA-A*03:01 | 91 |
| RPGAGPPGIL | Noncoding | ncRNA | SNRPA1 | HLA-B*07:02 | 92 |
| IIHSSSLLL | Noncoding | Antisense[4] | NA | HLA-C*07:01 | 93 |
| AEHQEGTGTW | Noncoding | Antisense | NA | HLA-B*44:03 | 94 |
| EALPDLEQL | Noncoding | Antisense | NA | HLA-C*03:03 | 95 |
| GKDPNPWL | Noncoding | Antisense | NA | HLA-B*39:01 | 96 |
| PSPLRPSL | Noncoding | Antisense | NA | HLA-B*07:02 | 97 |
| SLLNVIGLSV | Noncoding | Antisense | NA | HLA-A*02:01 | 98 |
| YRALSLAGL | Noncoding | Antisense | NA | HLA-B*39:01 | 99 |

TABLE 3B-continued

| | | | | | |
|---|---|---|---|---|---|
| | Translation | | | MHC class I | SEQ ID |
| TSA sequence | events[1] | Genomic origin[2] | Gene name | allele | NO: |
| SLGAGLSPCL | Coding-in | Canonical | KIAA1328 | HLA-A*02:01 | 100 |
| SPQTQTHTL | Coding-in | Canonical | MUC4 | HLA-B*07:02 | 101 |
| STQMTITTQK | Coding-in | Canonical | MUC16 | HLA-A*11:01 | 102 |
| TPKLRETSV | Coding-in | Canonical | MUC16 | HLA-B*08:01 | 103 |

[1]The "Translation events" column summarized the relation of TSA-coding sequence to ORFs, with outside of ORFs as "Noncoding", ORF-overlapping but frameshifted as "Coding-out", ORF-matched as "Coding-in".
[2]The "Genomic origin" column further annotate aeTSAs according to the biotypes from Ensembl. For example, "Antisense" means the sequence is on the opposite stand as an annotated gene; "Canonical" refers to canonical/annotated ORF; "ncRNA" is the annotated RNAs without ORFs according to Ensembl.
[3]"ncRNA" refer to the cases when TSA-coding sequences match to the exons of noncoding transcripts.
[4]"Noncoding antisense" means the TSA-coding sequence is antisense of a gene in Ensembl annotation, thus it's a noncoding region.

TABLE 3C

Characteristics of previously reported
aeTSAs identified in the present study

| | | | | | |
|---|---|---|---|---|---|
| TSA sequence | Translation events | Genomic origin | Gene name | MHC class I allele | SEQ ID NO: |
| ASNPVIKKK | Noncoding | ncRNA | NEK2 | HLA-A*11:01 | 104 |
| AEEEIMKKI | Coding-in | Canonical | IGF2BP3 | HLA-B*44:03 | 105 |
| FAFGEPREL | Coding-in | Canonical | MAGEC 1 | HLA-C*12:03 | 106 |
| GTSPPSVEK | Coding-in | Canonical | MUC16 | HLA-A*11:01 | 107 |
| IMKKIRESY | Coding-in | Canonical | IGF2BP3 | HLA-B*15:01 | 108 |
| KEVDPASNTY | Coding-in | Canonical | MAGEA4 | HLA-B*44:03 | 109 |
| RVKSTISSL | Coding-in | Canonical | MUC16 | HLA-B*07:02 | 110 |
| SQGFSHSQM | Coding-in | Canonical | MUC16 | HLA-B*15:01 | 111 |

Figure 3A:
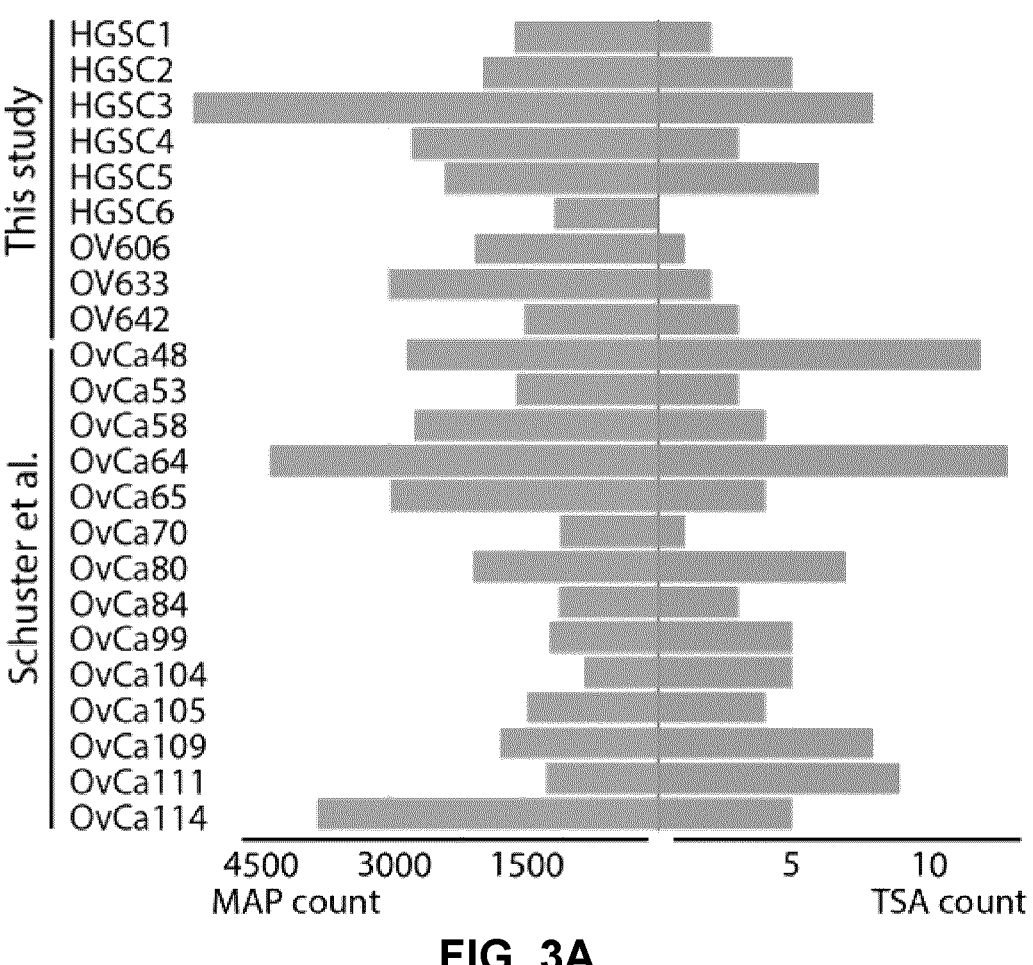
FIGS. 3A-D show that most TSAs derive from unmutated non-exonic sequences.
Figure 3B:
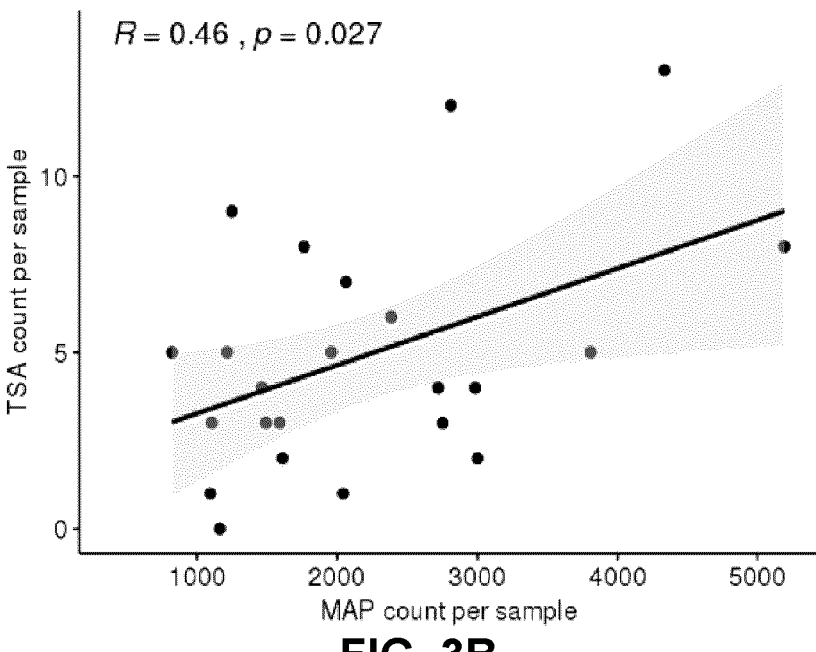

Example 3: Most HGSC TSAs are Unmutated MAPs Resulting from Non-Canonical Translation With an average of 2200 unique MAPs identified per sample, a total of 111 unique TSAs (FIG. 3A) was found. The number of TSAs identified per sample significantly correlated with the number of MAPs (FIG. 3B). Besides, there was a modest correlation between the number of MAPs per HLA allele and tumor sample size (FIG. 10). This is consistent with the notion that tumor sample size is a limiting factor in MS analyses (28). In principle, TSAs that originate from mutated noncoding sequences could be designated as both mTSAs or aeTSAs. Arbitrarily, it was decided to label them as mTSAs. The rationale was that irrespective of their genomic origin (exonic or not) mTSAs are expected to be "private TSAs", that is, not to be shared by a large proportion of tumors. In contrast, unmutated aeTSAs can theoretically be shared by a significant proportion of HGSCs.

Figures 3C, 3D:
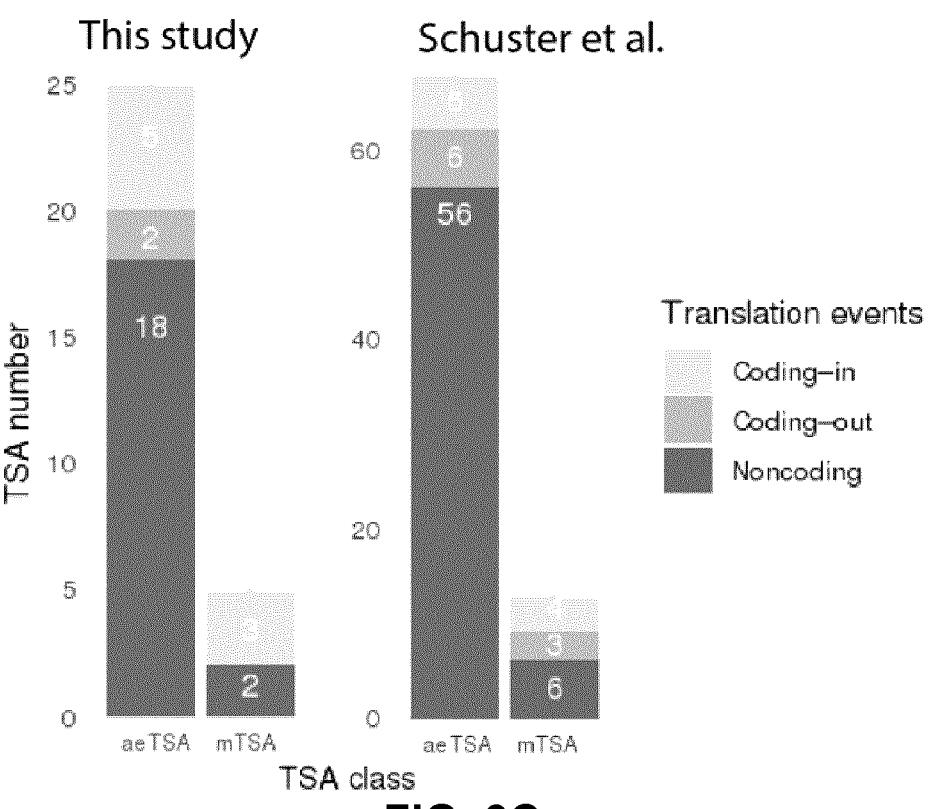

Notably, the features of TSAs identified in samples initially processed in the current study or by Schuster et al. were remarkably similar (FIG. 3C). This suggests that the proteogenomic approach described herein can be applied to RNA-Seq and MS data in general, and is not ostensibly affected by interlaboratory variability. In both cohorts, about 83% of TSAs were unmutated, and the majority of TSAs resulted from noncanonical translation: primarily from noncoding regions, and to a lesser extent from out-of-frame exonic translation (FIG. 3C). Two features of aeTSAs are noteworthy: i) 80% derive from noncoding sequences, in particular intronic (31%) and intergenic (22%) and ii) 90% are novel MAPs (FIG. 3D). Previously reported MAPs derived from in-frame exonic translation except for one that matched to a processed-transcript (biotype annotated by Ensembl database) whose corresponding protein isoform is included in the UniProt database (13, 39-43 and U.S. patent Publication No. 2012/0077696 A1).

Example 4: Expression of aeTSA-Coding Transcripts in Ovarian Cancer Samples

Figure 4A:
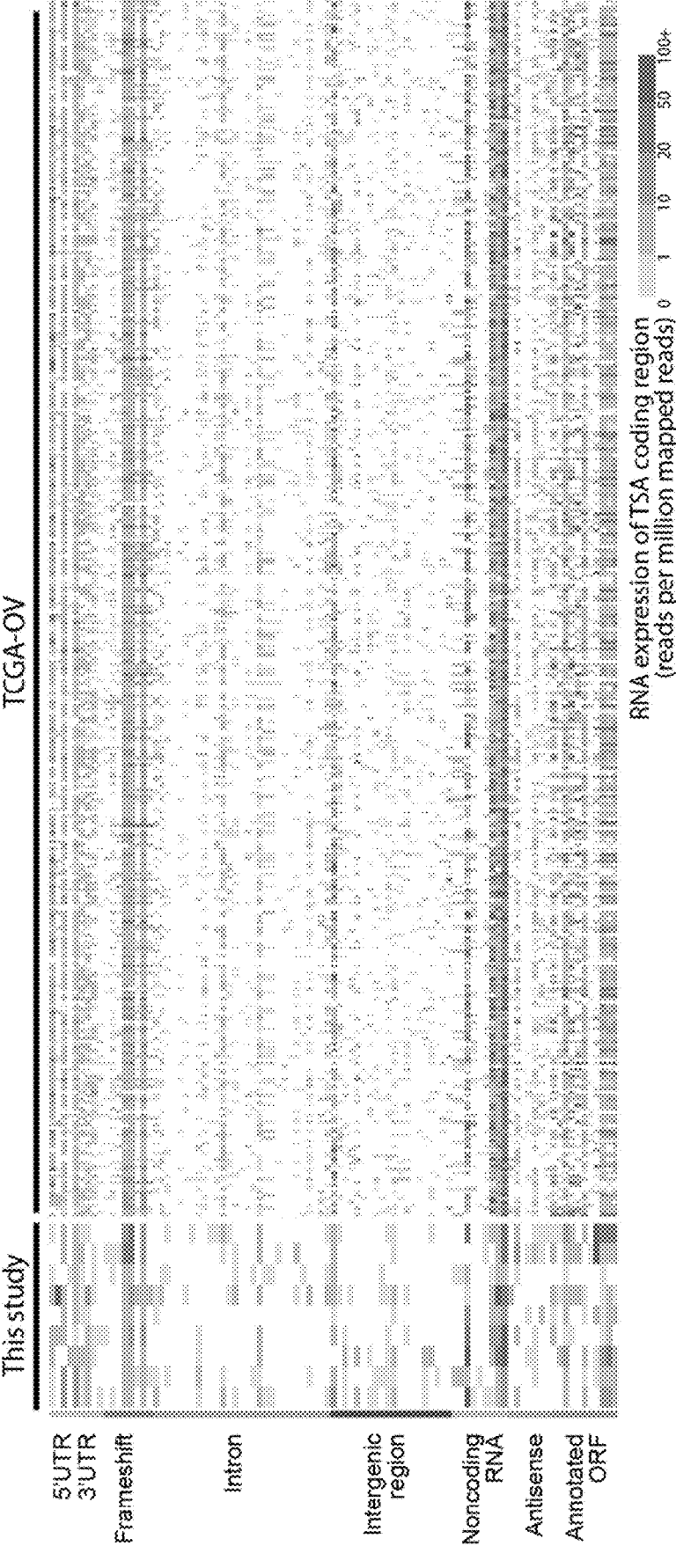
FIG. 4 shows the expression of aeTSA coding regions across ovarian cancer samples. Heatmap shows the RNA expression for the region coding each aeTSA in 9 samples reported in this study (left) and 378 samples from the TCGA-OV cohort, with color intensity showing RNA level in reads mapped in region per million reads.

To determine whether cancer-specific expression of aeTSA-coding transcripts result from random transcriptional noise or from recurrent transcriptional aberrations, the RNA expression of genomic regions coding for the 93 aeTSAs identified in samples from this study and from the TCGA ovarian cancer cohort was analyzed. Regions coding for aeTSAs were expressed in a substantial proportion of ovarian cancers: 72 (77%) were expressed in at least 10% of samples and 16 (17%) were expressed in at least 80% of samples (FIG. 4). These commonly expressed regions have high potential to generate sharing TSAs between patients. It may thus be concluded that expression of this set of 93 aeTSA-coding transcripts in HGSC is not a rare or random event but rather a common feature of HGSCs.

Example 5: Genomic Correlates of aeTSA Expression

Figure 5A:
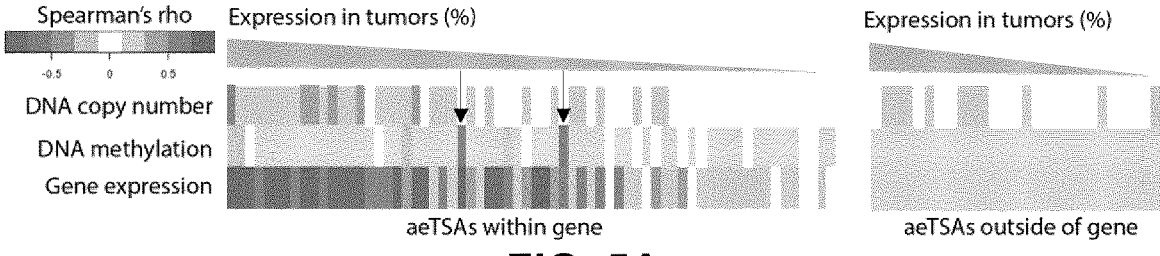
FIGS. 5A-B show that copy number changes correlate with expression of several aeTSAs.

To understand the mechanisms of aeTSA expression, the multi-omic data from the TCGA-OV dataset was used to explore the relationship between aeTSA RNA expression and local genetic or epigenetic aberrations. Correlations were tested between focal DNA copy number changes, DNA methylation level on the gene promoter regions and the RNA expression for each aeTSA when applicable (FIG. 5A).

Figure 5B:
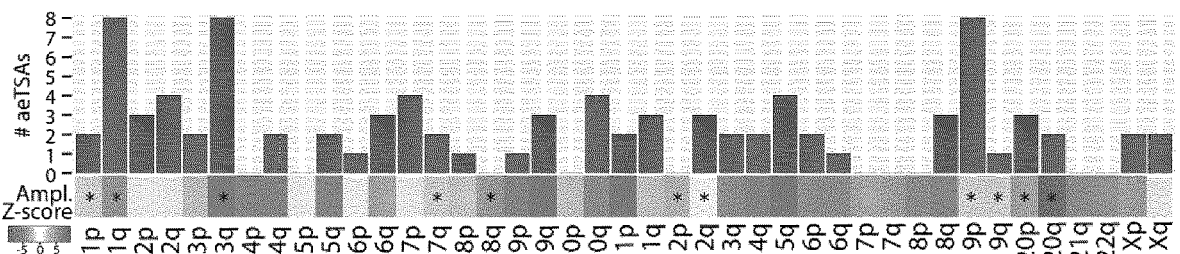

When an aeTSA derived from a genomic region that is part of a gene (exon, intron or UTR), the correlation between expression of the relevant gene and aeTSA expression was also analyzed. In the latter situation, a conspicuous correlation between gene and aeTSA expression (FIG. 5A) was observed. This suggests that for aeTSAs whose coding region is in a gene, regulation of aeTSA expression generally affects the whole gene. Besides, changes in DNA copy number showed a positive correlation with RNA expression level of aeTSAs; this was the case for both within-gene aeTSAs and out-of-gene aeTSAs (antisense and intergenic). This suggest that DNA copy number alterations have a substantial effect on aeTSA expression. Notably, this correlation was particularly strong for the within-gene aeTSAs expressed in a larger proportion of tumors (FIG. 11A). When the chromosomal distribution of aeTSA-coding regions was examined, it was found that several chromosome arms frequently amplified in HGSC yielded many aeTSAs (FIG. 5B). For example, the long arm of chromosome 3, which is commonly amplified in ovarian cancer (44), was the source of eight aeTSAs. As one of the top amplified regions, MECOM located at 3q26.2 (44) generated 3 overlapping exonic out-of-frame aeTSAs (Table 3B). However, amplification of chromosome arms was not always necessary (e.g., 15 q) nor sufficient (e.g., 8 q) to generate aeTSAs (FIG. 5B, FIG. 11B).

Due to the technology used by TCGA for analysis of DNA methylation (HM27 arrays), methylation data were unavailable for the out-of-gene aeTSAs and the promoters of some aeTSA source genes. The analysis of promoter methylation was therefore limited to a subset of 17 aeTSAs. Still, for six aeTSAs, a significant correlation between DNA methylation and aeTSA expression was found (FIG. 5A). The correlation was negative in five cases and positive in one case. This is consistent with the notion that promoter demethylation frequently results in enhanced transcription. Notably, the two genes showing the highest negative correlation were MAGEC1 ($\rho=-0.53$, $P_{adj}=1.6\times10^{-26}$) and MAGEA4 ($\rho=-0.51$, $P_{adj}=6.7\times10^{-25}$) which are represented by dark bars with arrows in FIG. 5A. Genes of the MAGE family are CGAs that are overexpressed in several cancer types, including HGSC (3). Overall, it may be concluded that aeTSA expression is regulated, at least in part, at the transcriptional level by variations in gene copy number and DNA methylation.

Example 6: The Expression of Three aeTSAs Correlates with Improved Survival

Figure 6A:
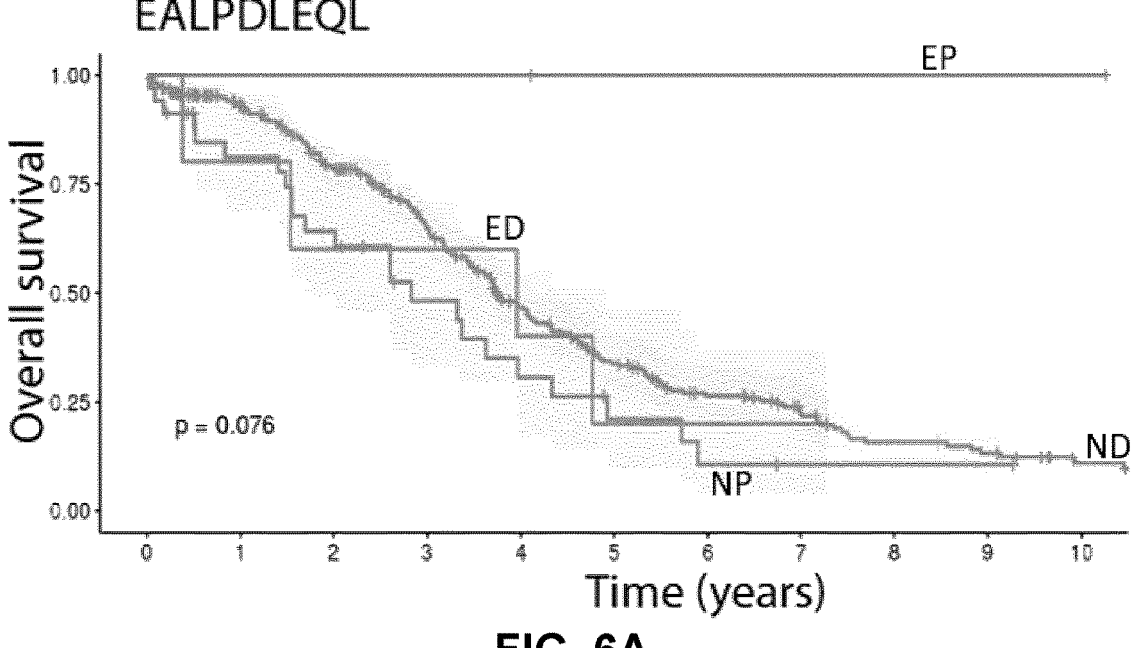
Figure 6B:
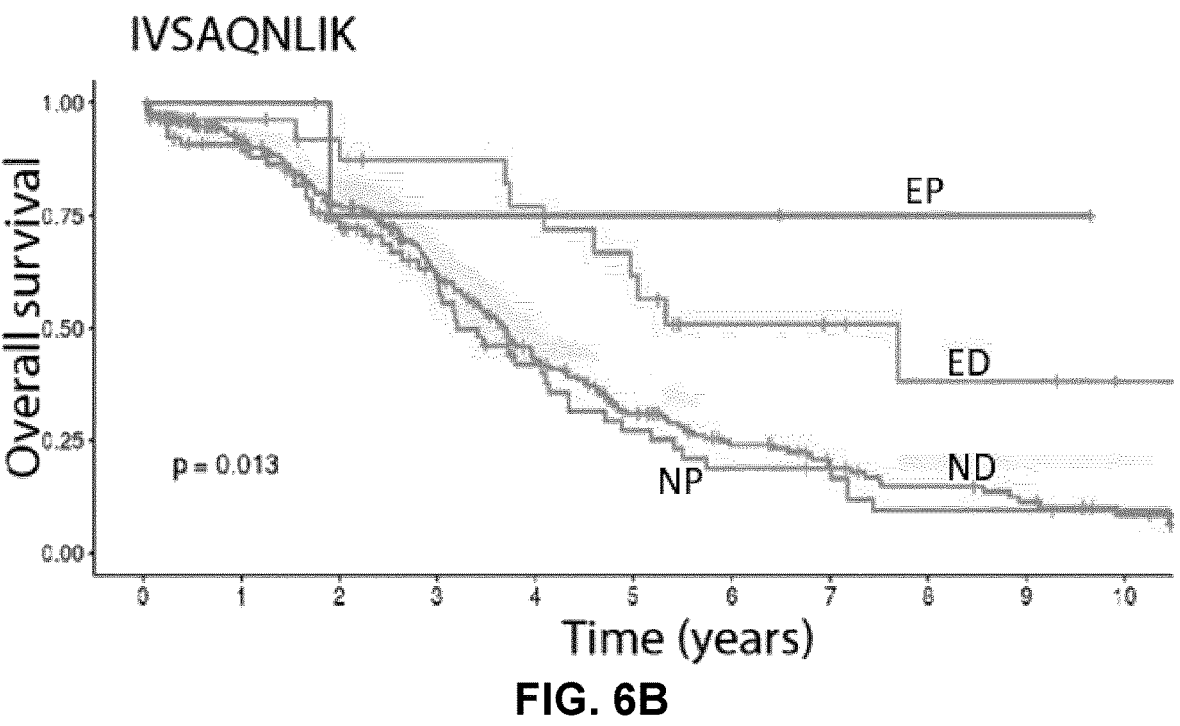
Figure 6C:
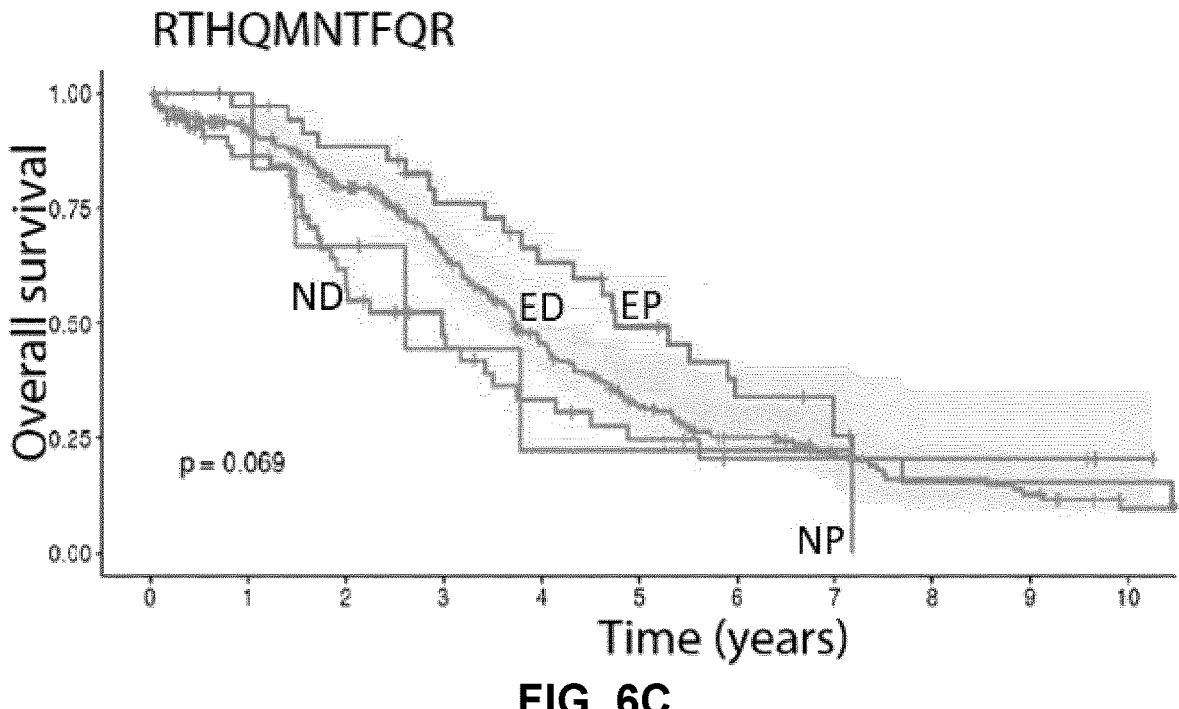

Next, it was assessed whether some aeTSAs might elicit spontaneous protective immune responses. Addressing this question is complicated by the fact that expression of aeTSAs at the peptide level requires, in addition to expression of aeTSA RNA, the presence of the relevant HLA allotype. Patients from the TCGA cohort were therefore subdivided into four subgroups based on the expression (or not) of individual aeTSA RNA and the presence (or not) of the relevant HLA allotype. Presentation of three aeTSAs correlated with a more favorable clinical outcome (FIG. 6A-C). The polymorphism of HLA alleles considerably reduced the size of each group, and therefore the statistical power of this analysis. Accordingly, the log-rank p-value for the three aeTSAs ranged from 0.013 to 0.076 (FIGS. 6A-C). Nonetheless, two observations provide supporting evidence that these correlations are biologically meaningful. First, the "protective effect" of these aeTSAs appeared to be HLA-restricted: in patients expressing aeTSA RNA, survival was superior when they also expressed the relevant HLA allele. Second, expression of the RTHQMNTFQR aeTSA and its relevant HLA allotype showed a positive correlation with tumor infiltration by T cells and cytotoxic T cells (FIG. 60, E); ANOVA, p<0.05).

Example 7: Median Number of aeTSAs Presented by Individual Tumors

Figure 7:
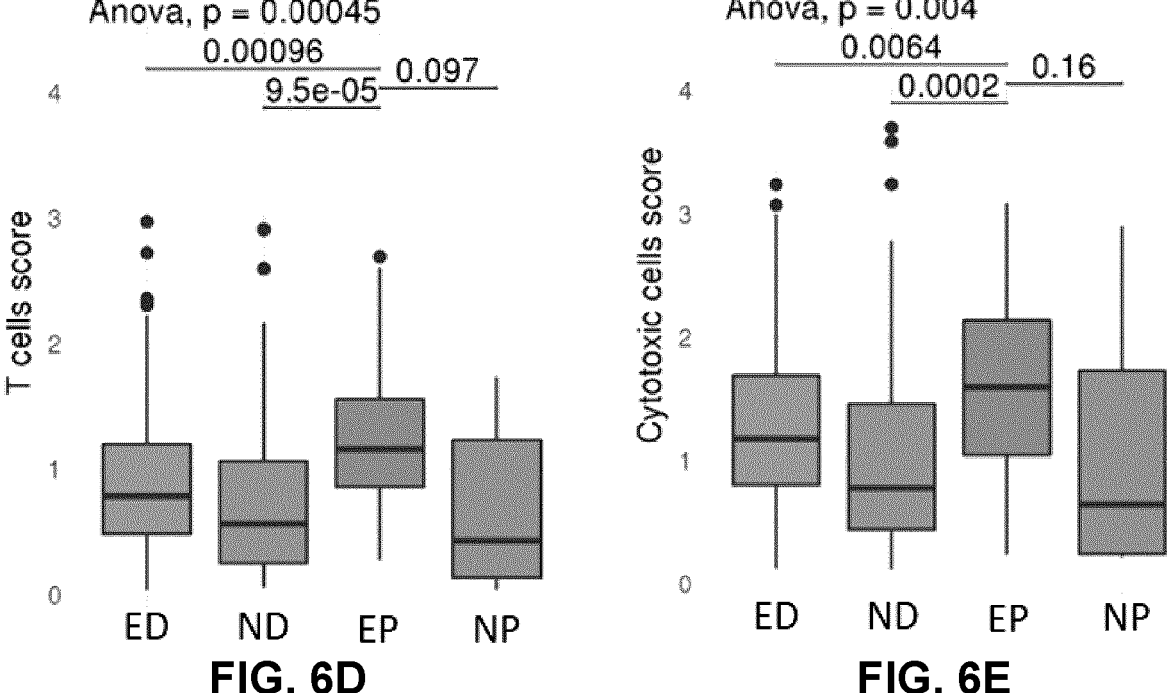
FIG. 7 shows the estimated frequency of aeTSAs presented by individual HGSCs in three different populations. One million simulated patients were generated for each population. An aeTSA was considered to be present in a simulated patient when its RNA was expressed and the relevant HLA allotype was present. Frequency of aeTSA RNA expression was based on TCGA-OV RNA-Seq data (as in FIG. 4). HLA allotype frequencies were obtained from USA National Marrow Donor Program. Red dash lines indicate the median number of aeTSAs per tumor in each population.
Figure 7:
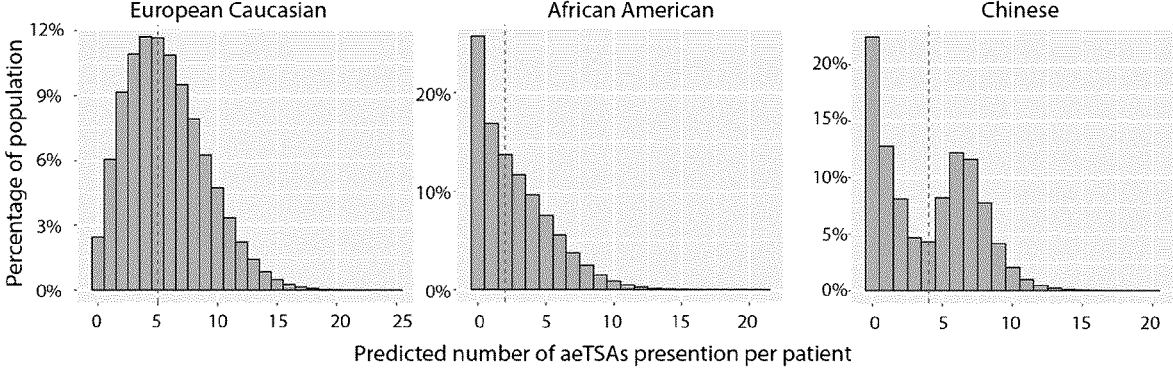

With the list of 93 aeTSAs, it was finally estimated at what extend the study may benefit TSA-targeted immunotherapy. Therefore, the presentation status for 93 aeTSAs in one million patients was randomly simulated. To estimate HLA allele frequencies, the three largest datasets from the USA National Marrow Donor Program: European Americans, African Americans and Chinese (45) were used. Six HLA alleles and aeTSA expression status were randomly generated independently using the allele frequencies in the given population, the expression proportion in TCGA-OV tumors, and the SNP frequencies when applicable. The number of aeTSAs per individual tumor was calculated as the sum of expressed HLA-aeTSA pairs. Based on these simulations, it was determined that at least one aeTSA could be found in 98% European Caucasians, 74% African Americans and 78% Chinese, and the median number of aeTSAs per tumor was 5 in European Caucasians, 2 African Americans and 4 in Chinese (FIG. 7). Differences between these populations resulted from variations in HLA allele frequencies and the fact that the tumor samples were mainly from European Caucasians. It is suspected that these calculations underestimate the number of aeTSAs per tumor, mainly for three reasons. Firstly, the fact that more than 50% of MAPs bind two or more HLA allotypes, often across supertypes or even loci (46), has not been taken into account. Secondly, genomic regions that code for a given MAP frequently generate overlapping MAPs presented by different HLA allotypes (23). Thirdly, for the five aeTSAs that include non-synonymous SNP listed in dbSNP, it was assumed that only the SNP variant generating MAPs in the samples was valid and that the other SNP variant did not generate MAPs. This cautious strategy was adopted because changes in a single amino acid may be sufficient to abrogate MAP presentation (47). It may be concluded that vaccines including the current set of 93 aeTSAs would cover practically all Caucasians with HGSC, and a significant proportion of African Americans and Asians (e.g., Chinese).

Although the present technology has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Jayson G C, Kohn E C, Kitchener H C, Ledermann J A. Ovarian cancer. Lancet 2014; 384:1376-88
2. Bowtell D D, Bohm S, Ahmed A A, Aspuria P J, Bast R C, Jr., Beral V, et al. Rethinking ovarian cancer I I: reducing mortality from high-grade serous ovarian cancer. Nat Rev Cancer 2015; 15:668-79
3. Want M Y, Lugade A A, Battaglia S, Odunsi K. Nature of tumour rejection antigens in ovarian cancer. Immunology 2018; 155:202-10

4. Yang S Y C, Lheureux S, Karakasis K, Burnier J V, Bruce J P, Clouthier D L, et al. Landscape of genomic alterations in high-grade serous ovarian cancer from exceptional long- and short-term survivors. Genome Med 2018; 10:81

5. Zhang A W, McPherson A, Milne K, Kroeger D R, Hamilton P T, Miranda A, et al. Interfaces of Malignant and Immunologic Clonal Dynamics in Ovarian Cancer. Cell 2018; 173:1755-69 e22

6. Hamanishi J, Mandai M, Ikeda T, Minami M, Kawaguchi A, Murayama T, et al. Safety and Antitumor Activity of Anti-PD-1 Antibody, Nivolumab, in Patients With Platinum-Resistant Ovarian Cancer. J Clin Oncol 2015; 33:4015-22

7. Hamanishi J, Mandai M, Konishi I. Immune checkpoint inhibition in ovarian cancer. Int Immunol 2016; 28:339-48

8. Rodriguez-Garcia A, Minutolo N G, Robinson J M, Powell D J. T-cell target antigens across major gynecologic cancers. Gynecol Oncol 2017; 145:426-35

9. Riley R S, June C H, Langer R, Mitchell M J. Delivery technologies for cancer immunotherapy. Nat Rev Drug Discov 2019

10. Ehx G E, Perreault C. Discovery and characterization of actionable tumor antigens. Genome Med 2019; 11:1-3

11. Millar D G, Ohashi P S. Central tolerance: what you see is what you don't get! Nat Immunol 2016; 17:115-6

12. Haen S P, Rammensee H G. The repertoire of human tumor-associated epitopes—identification and selection of antigens and their application in clinical trials. Curr Opin Immunol 2013; 25:277-83

13. Schuster H, Peper J K, Bosmuller H C, Rohle K, Backert L, Bilich T, et al. The immunopeptidomic landscape of ovarian carcinomas. Proc Natl Acad Sci USA 2017; 114:E9942-E51

14. Laumont C M, Daouda T, Laverdure J P, Bonneil E, Caron-Lizotte O, Hardy M P, et al. Global proteogenomic analysis of human MHC class I-associated peptides derived from non-canonical reading frames. Nat Commun 2016; 7:10238

15. Laumont C M, Vincent K, Hesnard L, Audemard E, Bonneil E, Laverdure J P, et al. Non-coding regions are the main source of targetable tumor-specific antigens. Sci Transl Med 2018; 10:aau5516

16. Gotter J, Brors B, Hergenhahn M, Kyewski B. Medullary epithelial cells of the human thymus express a highly diverse selection of tissue-specific genes colocalized in chromosomal clusters. J Exp Med 2004; 199:155-66

17. Bobisse S, Genolet R, Roberti A, Tanyi J L, Racle J, Stevenson B J, et al. Sensitive and frequent identification of high avidity neo-epitope specific CD8 (+) T cells in immunotherapy-naive ovarian cancer. Nat Commun 2018; 9:1092

18. Simoni Y, Becht E, Fehlings M, Loh C Y, Koo S L, Teng K W W, et al. Bystander CD8(+) T cells are abundant and phenotypically distinct in human tumour infiltrates. Nature 2018; 557:575-9

19. Marty R, Kaabinejadian S, Rossell D, Slifker M J, van de Haar J, Engin H B, et al. MHC-1 Genotype Restricts the Oncogenic Mutational Landscape. Cell 2017

20. Capietto A H, Jhunjhunwala S, Delamarre L. Characterizing neoantigens for personalized cancer immunotherapy. Curr Opin Immunol 2017; 46:58-65

21. Bilich T, Nelde A, Bichmann L, Roerden M, Salih H R, Kowalewski D J, et al. The HLA ligandome landscape of chronic myeloid leukemia delineates novel T-cell epitopes for immunotherapy. Blood 2019; 133:550-65

22. Löffler M W, Mohr C, Bichmann L, Freudenmann L K, Walzer M, Schroeder C M, et al. Multi-omics discovery of exome-derived neoantigens in hepatocellular carcinoma. Genome Med 2019; 11:1-16

23. Pearson H, Daouda T, Granados D P, Durette C, Bonneil E, Courcelles M, et al. MHC class I-associated peptides derive from selective regions of the human genome. J Clin Invest 2016; 126:4690-701

24. Szolek A, Schubert B, Mohr C, Sturm M, Feldhahn M, Kohlbacher O. OptiType: precision HLA typing from next-generation sequencing data. Bioinformatics 2014; 30:3310-6

25. Bolger A M, Lohse M, Usadel B. Trimmomatic: a flexible trimmer for Illumina sequence data. Bioinformatics 2014; 30:2114-20

26. Garrison E, Marth G. Haplotype-based variant detection from short-read sequencing. arXiv 2012; 1207.3907 [q-bio.GN]

27. Daouda T, Perreault C, Lemieux S. pyGeno: A Python package for precision medicine and proteogenomics. F1000Res 2016; 5:381

28. Lanoix J, Durette C, Courcelles M, Cossette E, Comtois-Marotte S, Hardy M P, et al. Comparison of the MHC I immunopeptidome repertoir of B-cell lymphoblasts using two isolation methods. Proteomics 2018; 18:e1700251

29. Andreatta M, Nielsen M. Gapped sequence alignment using artificial neural networks: application to the MHC class I system. Bioinformatics 2016; 32:511-7

30. Gaidatzis D, Lerch A, Hahne F, Stadler M B. QuasR: quantification and annotation of short reads in R. Bioinformatics 2015; 31:1130-2

31. Colaprico A, Silva T C, Olsen C, Garofano L, Cava C, Garolini D, et al. TCGAbiolinks: an R/Bioconductor package for integrative analysis of TCGA data. Nucleic Acids Res 2016; 44:e71

32. Danaher P, Warren S, Dennis L, D'Amico L, White A, Disis M L, et al. Gene expression markers of Tumor Infiltrating Leukocytes. J Immunother Cancer 2017; 5:18

33. Perez-Riverol Y, Csordas A, Bai J, Bernal-Llinares M, Hewapathirana S, Kundu D J, et al. The PRIDE database and related tools and resources in 2019: improving support for quantification data. Nucleic Acids Res 2019; 47:D442-d50

34. Shao W, Pedrioli P G A, Wolski W, Scurtescu C, Schmid E, Vizcaino J A, et al. The SysteMHC Atlas project. Nucleic Acids Res 2018; 46:D1237-D47

35. Gfeller D, Bassani-Sternberg M. Predicting Antigen Presentation-What Could We Learn From a Million Peptides? Front Immunol 2018; 9:1716

36. Villani A C, Sarkizova S, Hacohen N. Systems Immunology: Learning the Rules of the Immune System. Annu Rev Immunol 2018; 36:813-42

37. Caron E, Kowalewski D J, Chiek Koh C, Sturm T, Schuster H, Aebersold R. Analysis of Major Histocompatibility Complex (MHC) Immunopeptidomes Using Mass Spectrometry. Mol Cell Proteomics 2015; 14:3105-17

38. Sansom S N, Shikama-Dorn N, Zhanybekova S, Nusspaumer G, Macaulay I C, Deadman M E, et al. Population and single-cell genomics reveal the Aire dependency, relief from Polycomb silencing, and distribution of self-antigen expression in thymic epithelia. Genome Res 2014; 24:1918-31

39. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics 2015; 14:658-73

40. Bassani-Sternberg M, Braunlein E, Klar R, Engleitner T, Sinitcyn P, Audehm S, et al. Direct identification of clinically relevant neoepitopes presented on native human melanoma tissue by mass spectrometry. Nat Commun 2016; 7:13404

41. Rizvi N A, Hellmann M D, Snyder A, Kvistborg P, Makarov V, Havel J J, et al. Cancer immunology. Mutational landscape determines sensitivity to PD-1 blockade in non-small cell lung cancer. Science 2015; 348:124-8

42. Gloger A, Ritz D, Fugmann T, Neri D. Mass spectrometric analysis of the HLA class I peptidome of melanoma cell lines as a promising tool for the identification of putative tumor-associated HLA epitopes. Cancer Immunol Immunother 2016; 65:1377-93

43. UniProt Consortium: a worldwide hub of protein knowledge. Nucleic Acids Res 2019; 47:D506-D15

44. Cancer Genome Atlas Research Network. Integrated genomic analyses of ovarian carcinoma. Nature 2011; 474:609-15

45. Maiers M, Gragert L, Klitz W. High-resolution HLA alleles and haplotypes in the United States population. Hum Immunol 2007; 68:779-88

46. Rao X, Hoof I, Costa A I, van Baarle D, Kesmir C. HLA class I allele promiscuity revisited. Immunogenetics 2011; 63:691-701

47. Granados D P, Sriranganadane D, Daouda T, Zieger A, Laumont C M, Caron-Lizotte O, et al. Impact of genomic polymorphisms on the repertoire of human MHC class I-associated peptides. Nat Commun 2014; 5:3600

48. Delaney J R, Patel C B, Willis K M, Haghighiabyaneh M, Axelrod J, Tancioni I, et al. Haploinsufficiency networks identify targetable patterns of allelic deficiency in low mutation ovarian cancer. Nat Commun 2017; 8:14423

49. Kahles A, Lehmann K V, Toussaint N C, Huser M, Stark S G, Sachsenberg T, et al. Comprehensive Analysis of Alternative Splicing Across Tumors from 8,705 Patients. Cancer Cell 2018; 34:211-24 e6

50. Ali M, Foldvari Z, Giannakopoulou E, Boschen M L, Stronen E, Yang W, et al. Induction of neoantigen-reactive T cells from healthy donors. Nat Protoc 2019

51. Croft N P, Smith S A, Pickering J, Sidney J, Peters B, Faridi P, et al. Most viral peptides displayed by class I MHC on infected cells are immunogenic. Proc Natl Acad Sci USA 2019; 116:3112-7.

What is claimed is:

1. A method of stimulating a T cell response against ovarian cancer in a subject comprising administering to the subject an effective amount of
   (a) one or more tumor antigen peptides of 15 amino acids or less comprising one or more of the amino acid sequences set forth in SEQ ID NOs: 1-103; or
   (b) one or more nucleic acids encoding the one or more tumor antigen peptides defined in (a).

2. The method of claim 1, wherein said ovarian cancer is a serous carcinoma.

3. The method of claim 2, wherein said serous carcinoma is high-grade serous carcinoma (HGSC).

4. The method of claim 1, further comprising administering at least one additional antitumor agent or therapy to the subject.

5. The method of claim 4, wherein said at least one additional antitumor agent or therapy is a chemotherapeutic agent, immunotherapy, an immune checkpoint inhibitor, radiotherapy or surgery.

6. The method of claim 1, wherein the one or more tumor antigen peptides or nucleic acids, are formulated in a pharmaceutical composition that further comprises at least one pharmaceutically acceptable excipient or carrier.

7. The method of claim 6, wherein the at least one pharmaceutically acceptable excipient or carrier comprises a lipid vehicle.

8. The method of claim 6, wherein the at least one pharmaceutically acceptable excipient or carrier comprises a vaccine adjuvant.

9. The method of claim 1, wherein the one or more tumor antigen peptides comprise the amino acid sequence set forth in SEQ ID NO: 36, SEQ ID NO: 88, SEQ ID NO: 102 and/or SEQ ID NO: 103.

10. The method of claim 1, wherein the method comprises administering to the subject an effective amount of one or more nucleic acids encoding the one or more tumor antigen peptides defined in (a).

11. The method of claim 10, wherein the one or more nucleic acids are mRNA molecules.

12. The method of claim 9, wherein the method comprises administering to the subject an effective amount of one or more nucleic acids encoding the one or more tumor antigen peptides comprising the amino acid sequence set forth in SEQ ID NO: 36, SEQ ID NO: 88, SEQ ID NO: 102 and/or SEQ ID NO: 103.

13. The method of claim 12, wherein the one or more nucleic acids are mRNA molecules.

14. The method of claim 11, wherein the one or more mRNA molecules are admixed with a lipid vehicle.

15. The method of claim 13, wherein the one or more mRNA molecules are admixed with a lipid vehicle.

16. The method of claim 1, wherein the method further comprises administering to the subject an effective amount of
   (i) one or more tumor antigen peptides of 15 amino acids or less comprising one or more of the amino acid sequences set forth in SEQ ID NOs: 104-111; or
   (ii) one or more nucleic acids encoding the one or more tumor antigen peptides defined in (i).

17. The method of claim 16, wherein the method comprises administering to the subject an effective amount of one or more nucleic acids encoding the one or more tumor antigen peptides defined in (i).

18. The method of claim 17, wherein the one or more mRNA molecules are admixed with a lipid vehicle.

19. The method of claim 18, wherein the one or more mRNA molecules are admixed with a lipid vehicle.

* * * * *